United States Patent
Zemlok et al.

(10) Patent No.: US 10,498,269 B2
(45) Date of Patent: Dec. 3, 2019

(54) POWERED SURGICAL STAPLING DEVICE

(71) Applicant: Covidien LP, Mansfield, MA (US)

(72) Inventors: Michael A. Zemlok, Prospect, CT (US); Richard Lech, Hamden, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 305 days.

(21) Appl. No.: 15/594,986

(22) Filed: May 15, 2017

(65) Prior Publication Data

US 2017/0245854 A1    Aug. 31, 2017

Related U.S. Application Data

(63) Continuation-in-part of application No. 14/598,586, filed on Jan. 16, 2015, which is a continuation-in-part
(Continued)

(51) Int. Cl.
*A61B 17/068* (2006.01)
*H02P 7/29* (2016.01)
*A61B 17/00* (2006.01)

(52) U.S. Cl.
CPC ...... *H02P 7/29* (2013.01); *A61B 2017/00022* (2013.01); *A61B 2017/00057* (2013.01); *A61B 2017/00106* (2013.01); *A61B 2017/00115* (2013.01); *A61B 2017/00199* (2013.01); *A61B 2017/00473* (2013.01); *A61B 2017/00734* (2013.01)

(58) Field of Classification Search
CPC ........ H02P 7/29; A61B 17/072; A61B 17/068

USPC .................................. 227/175.1, 175.3, 4, 7
See application file for complete search history.

(56) References Cited

U.S. PATENT DOCUMENTS 2,777,340 A    1/1957  Hettwer et al.
2,957,353 A   10/1960  Babacz
(Continued)

FOREIGN PATENT DOCUMENTS

AU   2008229795 A1   4/2009
CA      2451558 A1   1/2003
(Continued)

OTHER PUBLICATIONS

European Examination Report dated Jun. 21, 2018 issued in corresponding EP Appln. No. 16151576.2.
(Continued)

*Primary Examiner* — Gloria R Weeks

(57) ABSTRACT

A surgical stapler includes a handle assembly, an end effector, a firing rod disposed in mechanical cooperation with the end effector, a drive motor coupled to the firing rod, a sensor, and a controller. The end effector includes a first and second jaw member moveable relative to one another. The first jaw member includes a surgical fastener and the second jaw member includes an anvil. The drive motor is configured to advance the firing rod to cause the first and second jaw members to clamp tissue and to eject a surgical fastener. The surgical stapler includes a sensor that is configured measure a clamping force exerted on tissue by the first and second jaw members. The controller control a speed of the drive motor based on the measured clamping force.

20 Claims, 38 Drawing Sheets

Related U.S. Application Data of application No. 13/788,293, filed on Mar. 7, 2013, now abandoned, which is a continuation-in-part of application No. 12/189,834, filed on Aug. 12, 2008, now abandoned.

(60) Provisional application No. 60/997,854, filed on Oct. 5, 2007.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,595 A | 5/1997 | Sklar et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,769,791 A | 6/1998 | Benaron et al. |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,871,493 A | 2/1999 | Sjostrom et al. |
| 5,908,427 A | 6/1999 | McKean et al. |
| 5,954,259 A | 9/1999 | Viola et al. |
| 5,964,774 A | 10/1999 | McKean et al. |
| 5,972,023 A | 10/1999 | Tanner et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |

(56) References Cited

U.S. PATENT DOCUMENTS

| | | |
|---|---|---|
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,497,866 B2 | 3/2009 | Perez |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,118,206 B2 * | 2/2012 | Zand ............... A61B 5/0031 227/175.1 |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0273135 A1 | 12/2006 | Beetel |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |

(56) References Cited

U.S. PATENT DOCUMENTS

| | | |
|---|---|---|
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0108048 A1 | 4/2009 | Zemlok et al. |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0270355 A1 | 10/2010 | Whitman et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155781 A1 | 6/2011 | Swensgard et al. |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0066000 A1* | 3/2015 | An .................. A61B 5/1455 606/1 |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2017/0007254 A1 | 1/2017 | Jaworek et al. |

FOREIGN PATENT DOCUMENTS

| | | |
|---|---|---|
| CN | 1961839 A | 5/2007 |
| CN | 101856251 A | 10/2010 |
| CN | 102188270 A | 9/2011 |
| CN | 102247182 A | 11/2011 |
| DE | 102008053842 A1 | 5/2010 |
| EP | 0634144 A1 | 1/1995 |
| EP | 0648476 A2 | 4/1995 |
| EP | 0679367 A2 | 11/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |

(56) References Cited

FOREIGN PATENT DOCUMENTS

| | | |
|---|---|---|
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| EP | 3064153 A2 | 9/2016 |
| EP | 3231372 A2 | 10/2017 |
| ES | 2333509 A1 | 2/2010 |
| FR | 2861574 A1 | 5/2005 |
| JP | 08-038488 | 2/1996 |
| JP | 2005-125075 A | 5/2005 |
| JP | 2011189128 | 9/2011 |
| KR | 20120022521 A | 3/2012 |
| WO | 99/15086 A1 | 4/1999 |
| WO | 2000/072760 A1 | 12/2000 |
| WO | 2000/072765 A1 | 12/2000 |
| WO | 0162164 A2 | 8/2001 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003/090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/103797 A2 | 8/2008 |
| WO | 2008-112147 A1 | 9/2008 |
| WO | 2008/131362 A2 | 10/2008 |
| WO | 2008/133956 A2 | 11/2008 |
| WO | 2009-005850 A1 | 1/2009 |
| WO | 2009/039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009/149234 A1 | 12/2009 |
| WO | 2011/108840 A2 | 9/2011 |
| WO | 2012/040984 A1 | 4/2012 |
| WO | 2013134411 A1 | 9/2013 |
| WO | 2013148054 A1 | 10/2013 |
| WO | 2014194317 A1 | 12/2014 |

OTHER PUBLICATIONS

European Examination Report issued in Appl. No. EP 17161135.3 dated Apr. 13, 2018 (5 pages).
Extended European Search Report issued in Appl. No. EP 17186525.6 dated Feb. 1, 2018 (7 pages).
Canadian Office Action dated Sep. 11, 2017 in Appl. No. CA 2,935,353 (4 pages).
Australian Examination Report dated Oct. 22, 2018 issued in corresponding AU Appln. No. 2017213554.
European Search Report dated Oct. 25, 2018 issued in corresponding EP Appln. No. 18172032.7.
Canadian Office Action dated May 7, 2015 issued in Canadian Application No. 2,640,399.
Japanese Official Action and English language translation dated Jun. 2, 2015 from Appl. No. JP 2014-148482.
Australian Examination Report from Appl. No. AU 2014210681 dated Aug. 13, 2015.
European Examination Report from Appl. No. EP 14 182 013.4-1654 dated Aug. 14, 2015.
European Search Report dated Aug. 3, 2015, issued in European Application No. 14199775.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action and English language translation issued in Appl. No. CN 201410083679.5 dated Feb. 23, 2017.
Australian Examination Report from Appl. No. AU 2016200924 dated Mar. 2, 2017.
Australian Examination Report issued in Appl. No. AU 2014200501 dated May 2, 2017.
Extended European Search Report issued in Appl. No. EP 17157550.9 dated Jun. 22, 2017.
Extended European Search Report issued in Appl. No. EP 17161135.3 dated Jun. 12, 2017.
European Examination Report issued in Appl. No. EP 16151576.2 dated Jun. 23, 2017.
Examination Report for Australian Application No. 2017213554 dated Jan. 14, 2019.
Japanese Notice of Final Rejection issued in Appl. No. JP 2014-041537 dated May 10, 2018, together with English language translation (8 pages).
Japanese Office Action and English language translation issued in Appl. No. JP 2014-041537 dated Oct. 26, 2017 (7 pages).
Examination Report for Australian application No. 2017265019 dated Aug. 8, 2018 (3 pages).

(56) References Cited

OTHER PUBLICATIONS

Chinese Office Action dated Jul. 25, 2019 issued in corresponding CN Appln. No. 2016100314582.
Australian Examination Report dated Jun. 17, 2019 issued in corresponding AU Appln. No. 2019202294.
Australian Examination Report dated Jul. 25, 2019 issued in corresponding AU Appln. No. 2016200084.
Japanese Office Action dated Aug. 23, 2019 issued in corresponding JP Appln. No. 2016-005868.

* cited by examiner

POWERED SURGICAL STAPLING DEVICE

CROSS-REFERENCE TO RELATED APPLICATIONS

This application is a continuation-in-part of U.S. patent application Ser. No. 14/598,586, which was filed on Jan. 16, 2015, which is a continuation-in-part of U.S. patent application Ser. No. 13/788,293, which was filed on Mar. 7, 2013, which is a continuation-in-part of U.S. patent application Ser. No. 12/189,834, which was filed on Aug. 12, 2008, now abandoned, which claims the benefit of, and priority to, U.S. Provisional Patent Application Ser. No. 60/997,854, which was filed on Oct. 5, 2007. The entire contents of each of the foregoing applications are hereby incorporated by reference herein.

BACKGROUND

1. Technical Field

The present disclosure relates to a surgical stapler for implanting mechanical surgical fasteners into the tissue of a patient, and, in particular, to a surgical stapler which is powered by a motor for firing surgical fasteners into tissue and a feedback controller for controlling the stapler in response to one or more sensed feedback signals.

2. Background of Related Art

Current known devices can typically require 10-60 pounds of manual hand force to clamp tissue and deploy and form surgical fasteners in tissue which, over repeated use, can cause a surgeon's hand to become fatigued. Gas powered pneumatic staplers which implant surgical fasteners into tissue are known in the art. Certain of these instruments utilize a pressurized gas supply which connects to a trigger mechanism. The trigger mechanism, when depressed, simply releases pressurized gas to implant a fastener into tissue.

Motor-powered surgical staplers are also known in the art. These include powered surgical staplers having motors which activate staple firing mechanisms. However, these motor powered devices only provide for limited user control of the stapling process. The user can only toggle a single switch and/or button to actuate the motor and apply corresponding torque to the stapler's firing mechanisms. In certain other devices, a controller is used to control the stapler.

There is a continual need for new and improved powered surgical staplers which include various sensors. The sensors provide relevant feedback to feedback controllers which automatically adjust various parameters of the powered stapler in response to sensed feedback signals representative of stapler operation.

SUMMARY

According to one aspect of the present disclosure, a surgical stapler includes a handle assembly, an end effector coupled to the handle assembly, a firing rod disposed in mechanical cooperation with the end effector, a drive motor coupled to the firing rod, a sensor, and a controller operatively coupled to the drive motor. The end effector includes a first jaw member including a surgical fastener and a second jaw member including an anvil portion. The first and second jaw members are moveable relative to one another between an open position and a clamped position. The drive motor is configured to advance the firing rod to cause the first and second jaw members to clamp tissue and to eject a surgical fastener. The sensor is configured to measure a clamping force exerted on tissue by the first and second jaw members.

In another aspect, the sensor is configured to measure a firing force exerted on the surgical fastener. The controller is configured to control a speed of the drive motor based on the measured clamping force.

According to further aspects of the present disclosure, the controller is further configured to set the speed of the drive motor to a first firing speed in response to the measured clamping force being between a first threshold clamping force and a second threshold clamping force. In aspects, the first threshold clamping force may be about 0 pound-force (lbf) and the second threshold clamping force may be about 33 lbf, in embodiments the first threshold clamping force may be about 33 lbf and the second threshold clamping force may be about 72 lbf, and in other embodiments the first threshold clamping force may be about about 72 lbf and the second threshold clamping force may be about 145 lbf.

In one aspect of the present disclosure, the controller is further configured to stop the drive motor in response to the measured clamping force being greater than a first threshold clamping force. In aspects, the first threshold clamping force is about 145 lbf.

According to yet further aspects of the present disclosure, the controller is further configured to set the speed of the drive motor to a second firing speed in response to the measured firing force being between a first firing force threshold and a second firing force threshold. In aspects, the first firing force threshold is about 0 lbf and the second firing force threshold is about 65 lbf, in embodiments the first firing force threshold is about 65 lbf and the second firing force threshold is about 80 lbf, and in other embodiments the first firing force threshold is about 80 lbf and the second firing force threshold is about 145 lbf.

In one aspect of the present disclosure, if the firing force is greater than a first firing force threshold, the controller stops the drive motor. In aspects, the first firing force threshold is about 145 lbf.

According to yet further aspects of the present disclosure, the sensor is a strain gauge sensor disposed on at least one of the first jaw member, the second jaw member, or the firing rod. The strain gauge sensor is configured to measure the clamping force by monitoring a speed of the drive motor, a torque being applied by the drive motor, distance between the first and second jaw members, monitoring the temperature of one or more components of the surgical stapler, or a load on the firing rod.

According to a further aspect of the present disclosure, a method for controlling the firing speed of a surgical stapler is disclosed. The method comprises positioning tissue between a first jaw member and a second jaw member of an end effector, the first and second jaw members being moveable relative to one another and the first jaw member including a staple cartridge. The method further comprises measuring a maximum clamp force of the first and second jaw members on the tissue, setting a first firing speed of a staple from the staple cartridge based on the measured maximum clamp force, initiating the firing of the staple from the staple cartridge, measuring a firing force exerted on the staple, and adjusting the first firing speed of the surgical stapler to a second firing speed based on the measured firing force.

In some aspects of the present disclosure, the method includes stopping the firing of the staple from the staple cartridge if the measured firing force is greater than a first firing force threshold. In aspects, the first firing force threshold is about 145 lbf.

In some aspects of the present disclosure, the maximum clamp force is measured by a sensor configured to measure the clamping force by monitoring a speed of the drive motor, a torque being applied by the drive motor, a distance between the first and second jaw members, or a load on the firing rod.

Further, to the extent consistent, any of the aspects described herein may be used in conjunction with any or all of the other aspects described herein.

BRIEF DESCRIPTION OF THE DRAWINGS

Various embodiments of the subject instrument are described herein with reference to the drawings wherein.

DETAILED DESCRIPTION

Figure 1:
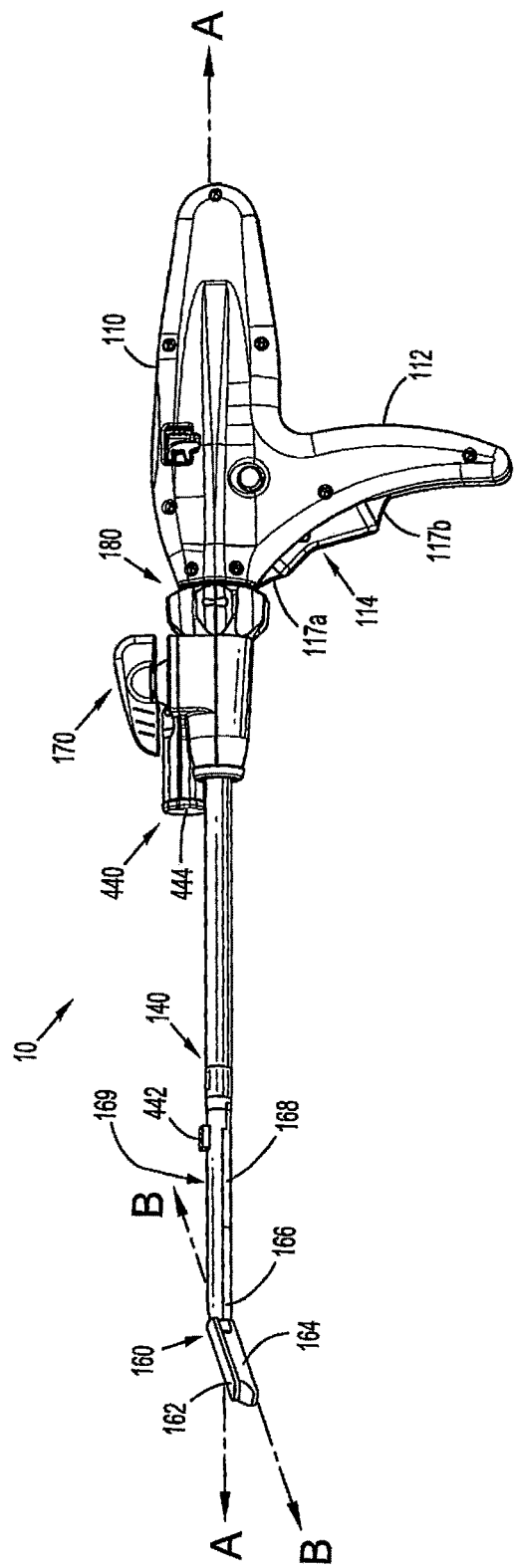
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 10. Referring initially to FIG. 1, powered surgical instrument 10 includes a housing 110, an endoscopic portion 140 defining a first longitudinal axis A-A extending therethrough, and an end effector 160, defining a second longitudinal axis B-B extending therethrough. Endoscopic portion 140 extends distally from housing 110 and the end effector 160 is disposed adjacent a distal portion of endoscopic portion 140. In an embodiment, the components of the housing 110 are sealed against infiltration of particulate and/or fluid contamination and help prevent damage of the component by the sterilization process.

According to an embodiment of the present disclosure, end effector 160 includes a first jaw member having one or more surgical fasteners (e.g., cartridge assembly 164) and a second opposing jaw member including an anvil portion for deploying and forming the surgical fasteners (e.g., an anvil assembly 162). In certain embodiments, the staples are housed in cartridge assembly 164 to apply linear rows of staples to body tissue either in simultaneous or sequential manner. Either one or both of the anvil assembly 162 and the cartridge assembly 164 are movable in relation to one another between an open position in which the anvil assembly 162 is spaced from cartridge assembly 164 and an approximated or clamped position in which the anvil assembly 162 is in juxtaposed alignment with cartridge assembly 164.

It is further envisioned that end effector 160 is attached to a mounting portion 166, which is pivotably attached to a body portion 168. Body portion 168 may be integral with endoscopic portion 140 of powered surgical instrument 10, or may be removably attached to the instrument 10 to provide a replaceable, disposable loading unit (DLU) or single use loading unit (SULU) (e.g., loading unit 169). In certain embodiments, the reusable portion may be configured for sterilization and re-use in a subsequent surgical procedure.

The loading unit 169 may be connectable to endoscopic portion 140 through a bayonet connection. It is envisioned that the loading unit 169 has an articulation link connected to mounting portion 166 of the loading unit 169 and the articulation link is connected to a linkage rod so that the end effector 160 is articulated as the linkage rod is translated in the distal-proximal direction along first longitudinal axis A-A. Other means of connecting end effector 160 to endoscopic portion 140 to allow articulation may be used, such as a flexible tube or a tube comprising a plurality of pivotable members.

The loading unit 169 may incorporate or be configured to incorporate various end effectors, such as vessel sealing devices, linear stapling devices, circular stapling devices, cutters, etc. Such end effectors may be coupled to endoscopic portion 140 of powered surgical instrument 10. The loading unit 169 may include a linear stapling end effector that does not articulate. An intermediate flexible shaft may be included between handle portion 112 and loading unit. It is envisioned that the incorporation of a flexible shaft may facilitate access to and/or within certain areas of the body.

Figure 2:
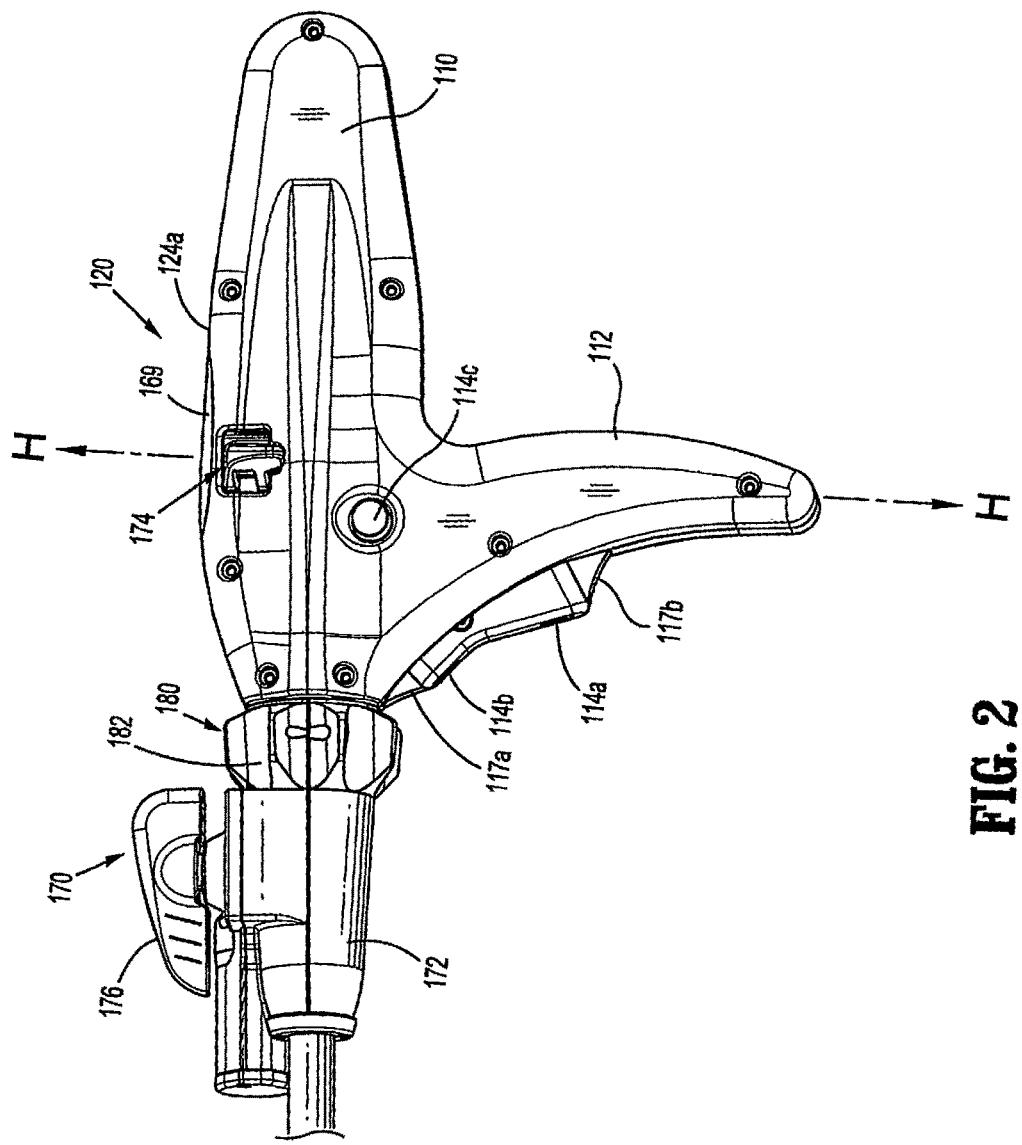
FIG. 2 is a partial enlarged perspective view of the powered surgical instrument according to the embodiment of the present disclosure of FIG. 1.

With reference to FIG. 2, an enlarged view of the housing 110 is illustrated according to an embodiment of the present disclosure. In the illustrated embodiment, housing 110 includes a handle portion 112 having a main drive switch 114 disposed thereon. The switch 114 may include first and second switches 114a and 114b formed together as a toggle switch. The handle portion 112, which defines a handle axis H-H, is configured to be grasped by fingers of a user. The handle portion 112 has an ergonomic shape providing ample palm grip leverage which helps prevent the handle portion 112 from being squeezed out of the user's hand during operation. Each switch 114a and 114b is shown as being disposed at a suitable location on handle portion 112 to facilitate its depression by a user's finger or fingers.

Figure 4:
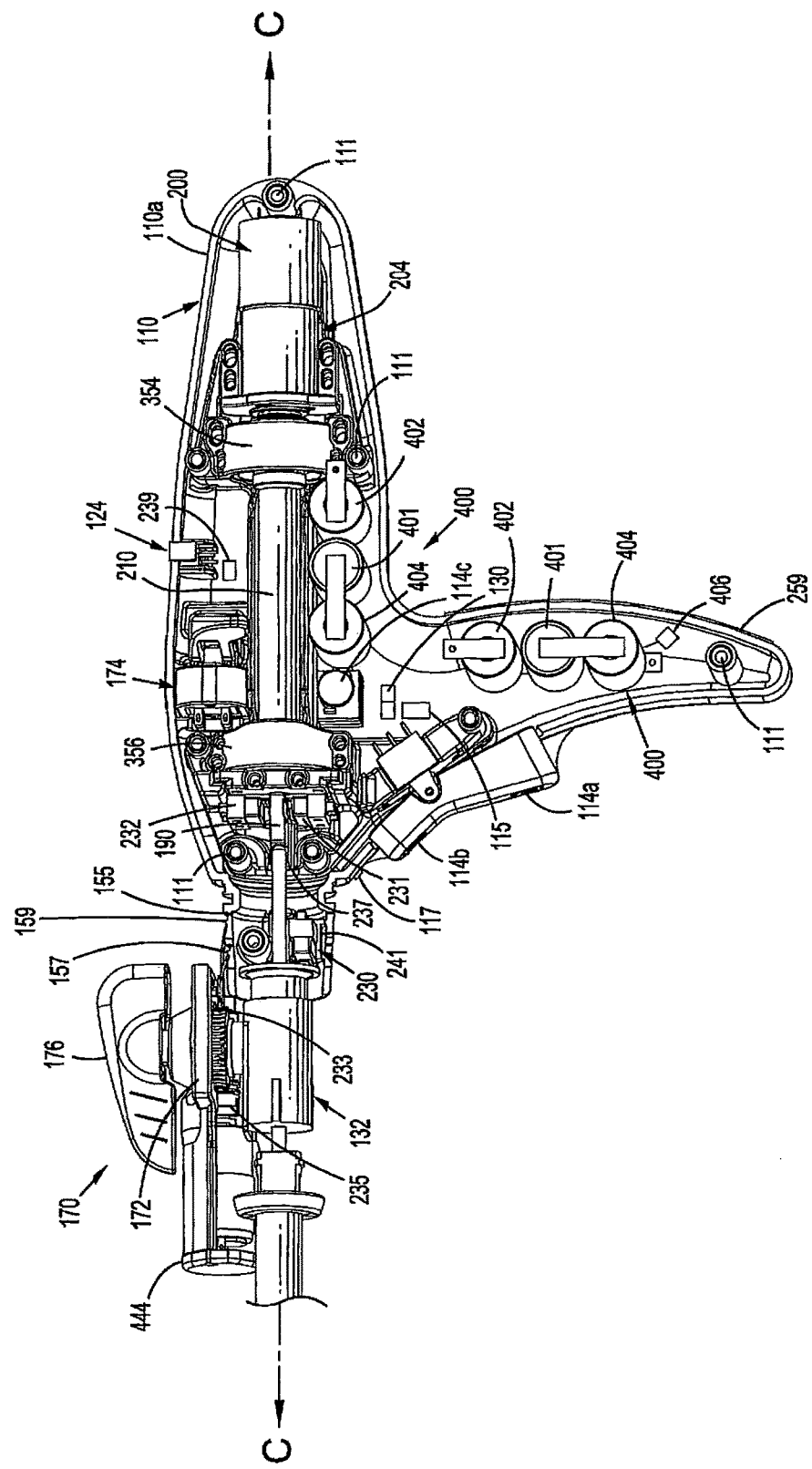
FIG. 4 is a partial perspective sectional view of internal components of the powered surgical instrument of FIG. 1 in accordance with an embodiment of the present disclosure.

Additionally, and with reference to FIGS. 1 and 2, switches 114a, 114b may be used for starting and/or stopping movement of drive motor 200 (FIG. 4). In one embodiment, the switch 114a is configured to activate the drive motor 200 in a first direction to advance firing rod 220 (FIG. 6) in a distal direction thereby clamping the anvil and the cartridge assemblies 162 and 164. Conversely, the switch 114b may be configured to retract the firing rod 220 to open the anvil and cartridge assemblies 162 and 164 by activating the drive motor 200 in a reverse direction. The retraction mode initiates a mechanical lock out, preventing further progression of stapling and cutting by the loading unit 169. The toggle has a first position for activating switch 114a, a second position for activating switch 114b, and a neutral position between the first and second positions. The details of operation of the drive components of the instrument 10 are discussed in more detail below.

The housing 110, in particular the handle portion 112, includes switch shields 117a and 117b. The switch shields 117a and 117b may have a rib-like shape surrounding the bottom portion of the switch 114a and the top portion of the switch 114b, respectively. The switch shields 117a and 117b prevent accidental activation of the switch 114. Further, the switches 114a and 114b have high tactile feedback requiring increased pressure for activation.

In one embodiment, the switches 114a and 114b are configured as multi-speed (e.g., two or more), incremental or variable speed switches which control the speed of the drive motor 200 and the firing rod 220 in a non-linear manner. For example, switches 114a, 114b can be pressure-sensitive. This type of control interface allows for gradual increase in the rate of speed of the drive components from a slower and more precise mode to a faster operation. To prevent accidental activation of retraction, the switch 114b may be disconnected electronically until a fail safe switch is pressed. In addition a third switch 114c may also be used for this purpose. Additionally or alternatively, the fail safe can be overcome by pressing and holding the switch 114b for a predetermined period of time from about 100 ms to about 2 seconds. The firing rod 220 then automatically retracts to its initial position unless the switch 114b is activated (e.g., pressed and released) during the retraction mode to stop the retraction. Subsequent pressing of the switch 114b after the release thereof resumes the retraction. Alternatively, the retraction of the firing rod 220 can continue to full retraction even if the switch 114b is released, in other embodiments.

The switches 114a and 114b are coupled to a non-linear speed control circuit 115 which can be implemented as a voltage regulation circuit, a variable resistance circuit, or a microelectronic pulse width modulation circuit. The switches 114a and 144b may interface with the control circuit 115 by displacing or actuating variable control devices, such as rheostatic devices, multiple position switch circuit, linear and/or rotary variable displacement transducers, linear and/or rotary potentiometers, optical encoders, ferromagnetic sensors, and/or Hall Effect sensors. This allows the switches 114a and 114b to operate the drive motor 200 in multiple speed modes, such as gradually increasing the speed of the drive motor 200 either incrementally or gradually depending on the type of the control circuit 115 being used, based on the depression of the switches 114a and 114b.

In a particular embodiment, the switch 114c may also be included (FIGS. 1, 2 and 4), wherein depression thereof may mechanically and/or electrically change the mode of operation from clamping to firing. The switch 114c is recessed within the housing 110 and has high tactile feedback to prevent false actuations. Providing of a separate control switch to initialize the firing mode allows for the jaws of the end effector to be repeatedly opened and closed, so that the instrument 10 is used as a grasper until the switch 114c is pressed, thus activating the stapling and/or cutting. The switch 114 may include one or more microelectronic membrane switches, for example. Such a microelectronic membrane switch includes a relatively low actuation force, small package size, ergonomic size and shape, low profile, the ability to include molded letters on the switch, symbols, depictions and/or indications, and a low material cost. Additionally, switches 114 (such as microelectronic membrane switches) may be sealed to help facilitate sterilization of the instrument 10, as well as helping to prevent particle and/or fluid contamination.

Figure 14:
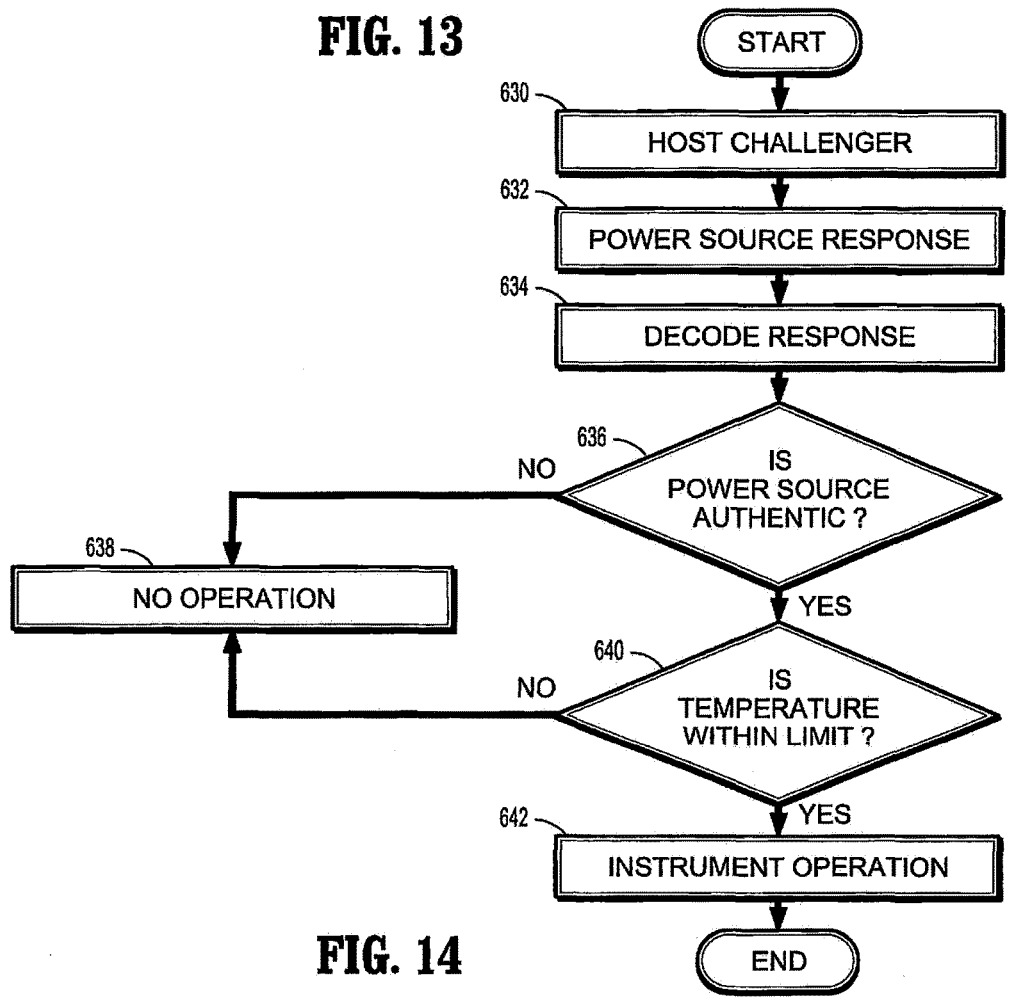
FIG. 14 is a flow chart diagram illustrating a method for authenticating the power source of the powered surgical instrument of FIG. 1.

As an alternative to, or in addition to switches 114, other input devices may include voice input technology, which may include hardware and/or software incorporated in a control system 501 (FIG. 14), or a separate digital module connected thereto. The voice input technology may include voice recognition, voice activation, voice rectification, and/or embedded speech. The user may be able to control the operation of the instrument in whole or in part through voice commands, thus freeing one or both of the user's hands for operating other instruments. Voice or other audible output may also be used to provide the user with feedback.

Figure 3:
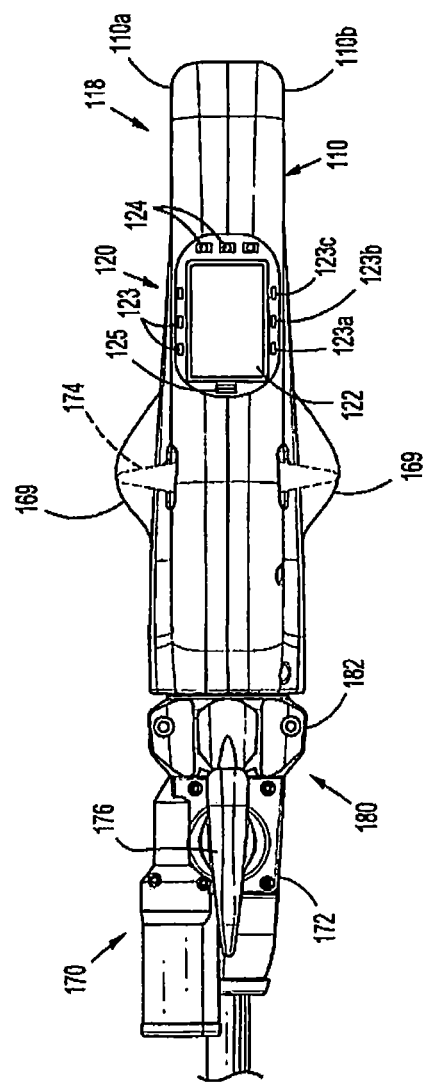
FIG. 3 is a partial enlarged plan view of the powered surgical instrument according to the embodiment of the present disclosure of FIG. 1.

Referring to FIG. 3, a proximal area 118 of housing 110 having a user interface 120 is shown. The user interface 120 includes a screen 122 and a plurality of switches 124. The user interface 120 may display various types of operational parameters of the instrument 10 such as "mode" (e.g., rotation, articulation or actuation), which may be communicated to user interface via a sensor, "status" (e.g., angle of articulation, speed of rotation, or type of actuation) and "feedback," such as whether staples have been fired based on the information reported by the sensors disposed in the instrument 10.

The screen 122 may be an LCD screen, a plasma screen, electroluminescent screen and the like. In one embodiment the screen 122 may be a touch screen, obviating the need for the switches 124. The touch screen may incorporate resistive, surface wave, capacitive, infrared, strain gauge, optical, dispersive signal or acoustic pulse recognition touch screen technologies. The touch screen may be used to allow the user to provide input while viewing operational feedback. This approach may enable facilitation of sealing screen components to help sterilize the instrument 10, as well as preventing particle and/or fluid contamination. In certain embodiments, screen is pivotably or rotatably mounted to the instrument 10 for flexibility in viewing screen during use or preparation (e.g., via a hinge or ball-and-socket mount).

The switches 124 may be used for starting and/or stopping movement of the instrument 10 as well as selecting the pivot direction, speed and/or torque. It is also envisioned that at least one switch 124 can be used for selecting an emergency mode that overrides various settings. The switches 124 may also be used for selecting various options on the screen 122, such as responding to prompts while navigating user interface menus and selecting various settings, allowing a user input different tissue types, and various sizes and lengths of staple cartridges.

The switches 124 may be formed from a micro-electronic tactile or non-tactile membrane, a polyester membrane, elastomer, plastic or metal keys of various shapes and sizes. Additionally, switches may be positioned at different heights from one another and/or may include raised indicia or other textural features (e.g., concavity or convexity) to allow a user to depress an appropriate switch without the need to look at user interface 120.

In addition to the screen 122, the user interface 120 may include one or more visual outputs 123 which may include one or more colored visible lights or light emitting diodes ("LED") to relay feedback to the user. The visual outputs 123 may include corresponding indicators of various shapes, sizes and/or colors having numbers and/or text which identify the visual outputs 123. The visual outputs 123 are disposed on top of the housing 110 such that the outputs 123 are raised and protrude in relation to the housing 110 providing for better visibility thereof.

The multiple lights display in a certain combination to illustrate a specific operational mode to the user. In one embodiment, the visual outputs 123 include a first light (e.g., yellow) 123a, a second light (e.g., green) 123b and a third light (e.g., red) 123c. The lights are operated in a particular combination associated with a particular operational mode as listed in Table 1 below.

TABLE 1

| Light Combination | | Operational Mode |
|---|---|---|
| Light | Status | No loading unit 169 or staple cartridge is loaded. |
| First Light | Off | |
| Second Light | Off | |
| Third Light | Off | |
| Light | Status | The loading unit 169 and/or staple cartridge are loaded and power is activated, allowing the end effector 160 to clamp as a grasper and articulate. |
| First Light | On | |
| Second Light | Off | |
| Third Light | Off | |
| Light | Status | A used loading unit 169 or staple cartridge is loaded. |
| First Light | Flashing | |
| Second Light | Off | |
| Third Light | Off | |
| Light | Status | Instrument 10 is deactivated and prevented from firing staples or cutting. |
| First Light | N/A | |
| Second Light | Off | |
| Third Light | N/A | |
| Light | Status | A new loading unit 169 is loaded, the end effector 160 is fully clamped and the instrument 10 is in firing staple and cutting |
| First Light | On | |
| Second Light | On | |

TABLE 1-continued

| Light Combination | | Operational Mode |
|---|---|---|
| Third Light | Off | modes. |
| Light | Status | Due to high stapling forces a pulse |
| First Light | On | mode is in effect, providing for a time |
| Second Light | Flashing | delay during which tissue is compressed. |
| Third Light | Off | |
| Light | Status | No system errors detected. |
| First Light | N/A | |
| Second Light | N/A | |
| Third Light | Off | |
| Light | Status | Tissue thickness and/or firing load is too |
| First Light | On | high, this warning can be overridden. |
| Second Light | On | |
| Third Light | On | |
| Light | Status | Functional system error is detected, |
| First Light | N/A | instrument 10 should be replaced. |
| Second Light | N/A | |
| Third Light | Flashing | |

In another embodiment, the visual output 123 may include a single multi-colored LED which displays a particular color associated with the operational modes as discussed above with respect to the first, second and third lights in Table 1.

The user interface 120 also includes audio outputs 125 (e.g., tones, bells, buzzers, integrated speaker, etc.) to communicate various status changes to the user such as lower battery, empty cartridge, etc. The audible feedback can be used in conjunction with or in lieu of the visual outputs 123. The audible feedback may be provided in the forms of clicks, snaps, beeps, rings and/or buzzers in single or multiple pulse sequences. In one embodiment, a simulated mechanical sound may be prerecorded which replicates the click and/or snap sounds generated by mechanical lockouts and mechanisms of conventional non-powered instruments. This eliminates the need to generate such mechanical sounds through the actual components of the instrument 10 and also avoids the use of beeps and other electronic sounds which are usually associated with other operating room equipment, thereby preventing confusion from extraneous audible feedback.

The instrument 10 may also provide for haptic or vibratory feedback through a haptic mechanism (not explicitly shown) within the housing 110. The haptic feedback may be used in conjunction with the auditory and visual feedback or in lieu thereof to avoid confusion with the operating room equipment which relies on audio and visual feedback. The haptic mechanism may be an asynchronous motor that vibrates in a pulsating manner. In one embodiment, the vibrations are at a frequency of about 30 Hz or above providing a displacement having an amplitude of 1.5 mm or lower to limit the vibratory effects from reaching the loading unit 169.

It is also envisioned that user interface 120 includes different colors and/or intensities of text on screen and/or on switches for further differentiation between the displayed items. The visual, auditory or haptic feedback can be increased or decreased in intensity. For example, the intensity of the feedback may be used to indicate that the forces on the instrument are becoming excessive.

FIGS. 2-4 illustrate an articulation mechanism 170, including an articulation housing 172, a powered articulation switch 174, an articulation motor 132, and a manual articulation knob 176. Translation of the powered articulation switch 174 or pivoting of the manual articulation knob 176 activates the articulation motor 132 which then actuates an articulation gear 233 of the articulation mechanism 170 as shown in FIG. 4. Actuation of articulation mechanism 170 causes the end effector 160 to move from its first position, where longitudinal axis B-B is substantially aligned with longitudinal axis A-A, towards a position in which longitudinal axis B-B is disposed at an angle to longitudinal axis A-A. Preferably, a plurality of articulated positions is achieved. The powered articulation switch 174 may also incorporate similar non-linear speed controls as the clamping mechanism as controlled by the switches 114a and 114b.

Further, the housing 110 includes switch shields 169 having a wing-like shape and extending from the top surface of the housing 110 over the switch 174. The switch shields 169 prevent accidental activation of the switch 174 and require the user to reach below the shield 169 in order to activate the articulation mechanism 170.

Figure 26:
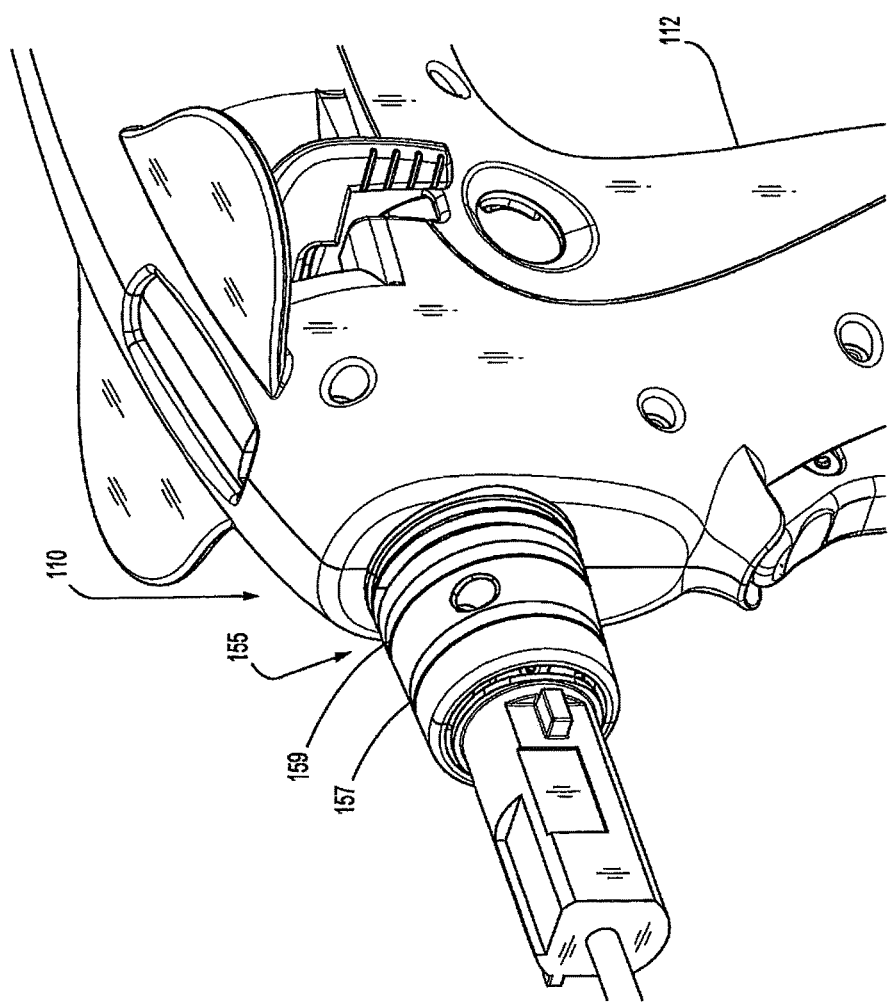
FIG. 26 is a partial perspective view of a nose assembly of the powered surgical instrument in accordance with an embodiment of the present disclosure.

Additionally, articulation housing 172 and powered articulation switch 174 are mounted to a rotating housing assembly 180. Rotation of a rotation knob 182 about first longitudinal axis A-A causes housing assembly 180 as well as articulation housing 172 and powered articulation switch 174 to rotate about first longitudinal axis A-A, and thus causes corresponding rotation of distal portion 224 of firing rod 220 and end effector 160 about first longitudinal axis A-A. The articulation mechanism 170 is electro-mechanically coupled to first and second conductive rings 157 and 159 which are disposed on the housing nose assembly 155 as shown in FIGS. 4 and 26. The conductive rings 157 and 159 may be soldered and/or crimped onto the nose assembly 155 and are in electrical contact with the power source 400 thereby providing electrical power to the articulation mechanism 170. The nose assembly 155 may be modular and may be attached to the housing 110 during assembly to allow for easier soldering and/or crimping of the rings. The articulation mechanism 170 includes one or more brush and/or spring loaded contacts in contact with the conductive rings 157 and 159 such that as the housing assembly 180 is rotated along with the articulation housing 172 the articulation mechanism 170 is in continuous contact with the conductive rings 157 and 159 thereby receiving electrical power from the power source 400.

Further details of articulation housing 172, powered articulation switch 174, manual articulation knob 176 and providing articulation to end effector 160 are described in detail in commonly-owned U.S. Patent Application Publication No. 2008/0223903A1 filed Mar. 15, 2007, the contents of which are hereby incorporated by reference in their entirety. It is envisioned that any combinations of limit switches, proximity sensors (e.g., optical and/or ferromagnetic), linear variable displacement transducers and/or shaft encoders which may be disposed within housing 110, may be utilized to control and/or record an articulation angle of end effector 160 and/or position of the firing rod 220.

FIGS. 4-8 illustrate various internal components of the instrument 10, including a drive motor 200, a drive tube 210 and a firing rod 220 having a proximal portion 222 and a distal portion 224. The drive tube 210 is rotatable about drive tube axis C-C extending therethrough. Drive motor 200 is disposed in mechanical cooperation with drive tube 210 and is configured to rotate the drive tube 210 about drive gear axis C-C. In one embodiment, the drive motor 200 may be an electrical motor or a gear motor, which may include gearing incorporated within its housing.

The housing 110 may be formed from two halves 110a and 110b as illustrated in FIG. 3. The two housing portion halves 110a and 110b may be attached to each other using screws at boss locators 111 which align the housing portions 110a and 110b. In addition, the housing 110 may be formed from plastic and may include rubber support members applied to the internal surface of the housing 110 via a two-shot molding process. The rubber support members may isolate the vibration of the drive components (e.g., drive motor 200) form the rest of the instrument 10.

The housing halves 110a and 110b may be attached to each via a thin section of plastic (e.g., a living hinge) that interconnects the halves 110a and 110b allowing the housing 110 to be opened by breaking away the halves 110a and 110b.

In one embodiment, the drive components (e.g., including a drive motor 200, a drive tube 210, a firing rod 220, etc.) may be mounted on a support plate allowing the drive components to be removed from the housing 110 after the instrument 10 has been used. The support plate mounting in conjunction with the hinged housing halves 110a and 110b provide for reusability and recyclability of specific internal components while limiting contamination thereof.

Figure 5:
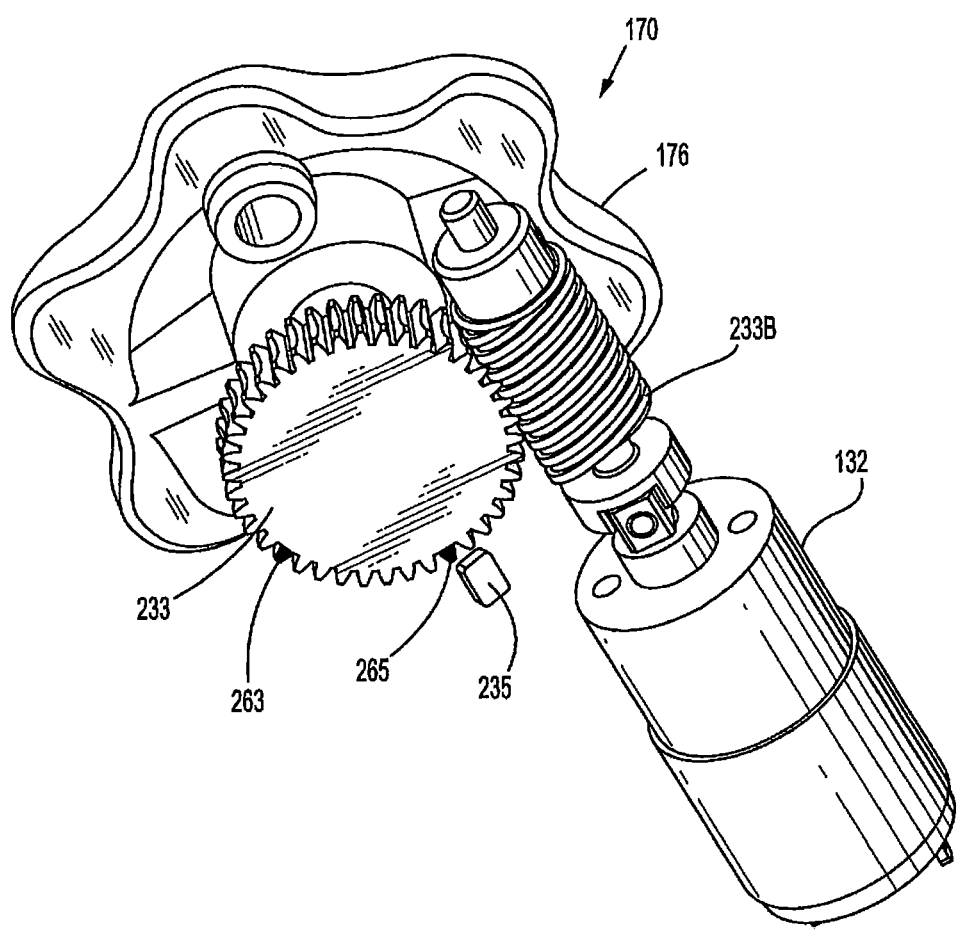
FIG. 5 is a perspective view of an articulation mechanism with parts separated of the powered surgical instrument of FIG. 1 in accordance with an embodiment of the present disclosure.
Figure 6:
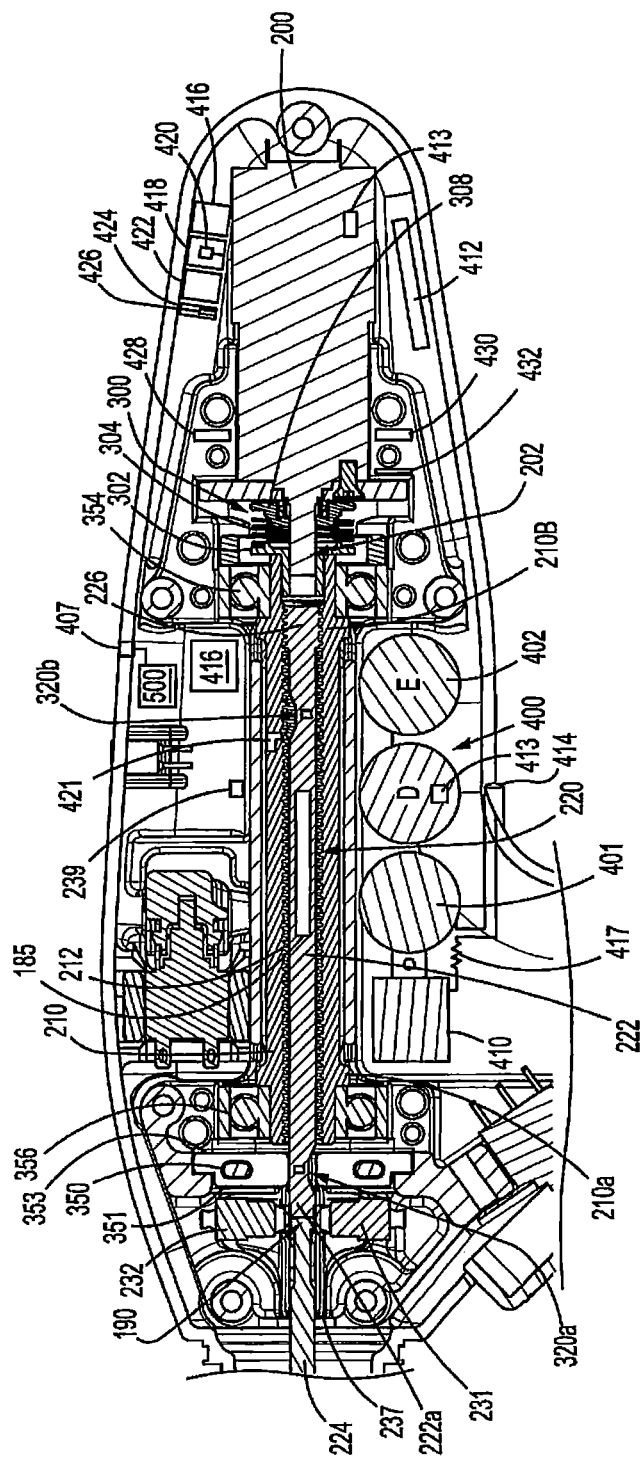
FIG. 6 is a partial cross-sectional view showing internal components of the powered surgical instrument according to the embodiment of the present disclosure of FIG. 1 disposed in a first position.

With reference to FIGS. 4-6, a firing rod coupling 190 is illustrated. Firing rod coupling 190 provides a link between the proximal portion 222 and the distal portion 224 of the firing rod 220. Specifically, the firing rod coupling 190 enables rotation of the distal portion 224 of the firing rod 220 with respect to proximal portion 222 of firing rod 220. Thus, firing rod coupling 190 enables proximal portion 222 of firing rod 220 to remain non-rotatable, as discussed below with reference to an alignment plate 350, while allowing rotation of distal portion 224 of firing rod 220 (e.g., upon rotation of rotation knob 182).

Figure 7:
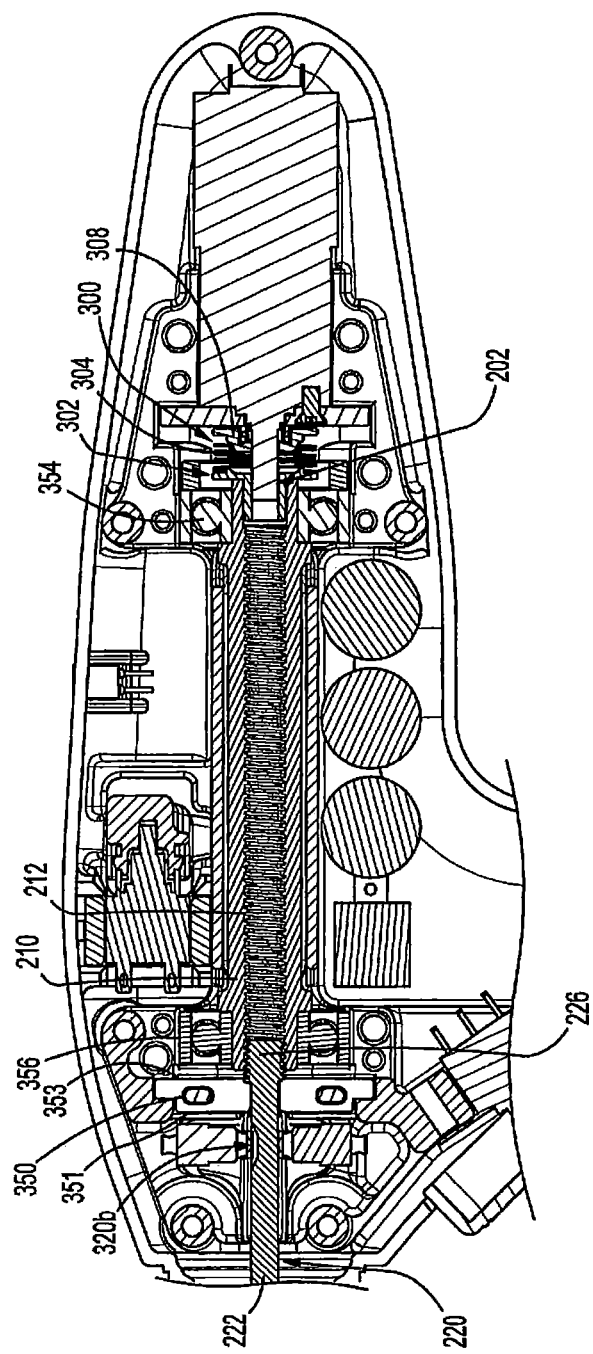
FIG. 7 is a partial cross-sectional view showing internal components of the powered surgical instrument according to the embodiment of the present disclosure of FIG. 1 disposed in a second position.

With reference to FIGS. 5 and 6, the proximal portion 222 of firing rod 220 includes a threaded portion 226, which extends through an internally-threaded portion 212 of drive tube 210. This relationship between firing rod 220 and drive tube 210 causes firing rod 220 to move distally and/or proximally, in the directions of arrows D and E, along threaded portion 212 of drive tube 210 upon rotation of drive tube 210 in response to the rotation of the drive motor 200. As the drive tube 210 rotates in a first direction (e.g., clockwise), firing rod 220 moves proximally as illustrated in FIG. 6, and the firing rod 220 is disposed at its proximal-most position. As the drive tube 210 rotates in a second direction (e.g., counter-clockwise), firing rod 220 moves distally as illustrated in FIG. 7, and the firing rod 220 is disposed at its distal-most position.

The firing rod 220 is distally and proximally translatable within particular limits. Specifically, a first end 222a of proximal portion 222 of firing rod 220 acts as a mechanical stop in combination with an alignment plate 350. That is, upon retraction when firing rod 220 is translated proximally, first end 222a contacts a distal surface 351 of alignment plate 350, thus preventing continued proximal translation of firing rod 220 as shown in FIG. 5. Additionally, threaded portion 226 of the proximal portion 222 acts as a mechanical stop in combination with alignment plate 350. That is, when firing rod 220 is translated distally, the threaded portion 226 contacts a proximal surface 353 of the alignment plate 350, thus preventing further distal translation of firing rod 220 as shown in FIG. 6. The alignment plate 350 includes an aperture therethrough, which has a non-round cross-section. The non-round cross-section of the aperture prevents rotation of proximal portion 222 of firing rod 220, thus limiting proximal portion 222 of firing rod 220 to axial translation therethrough. Further, a proximal bearing 354 and a distal bearing 356 are disposed at least partially around drive tube 210 for facilitation of rotation of drive tube 210, while helping align drive tube 210 within housing 110.

Figure 9:
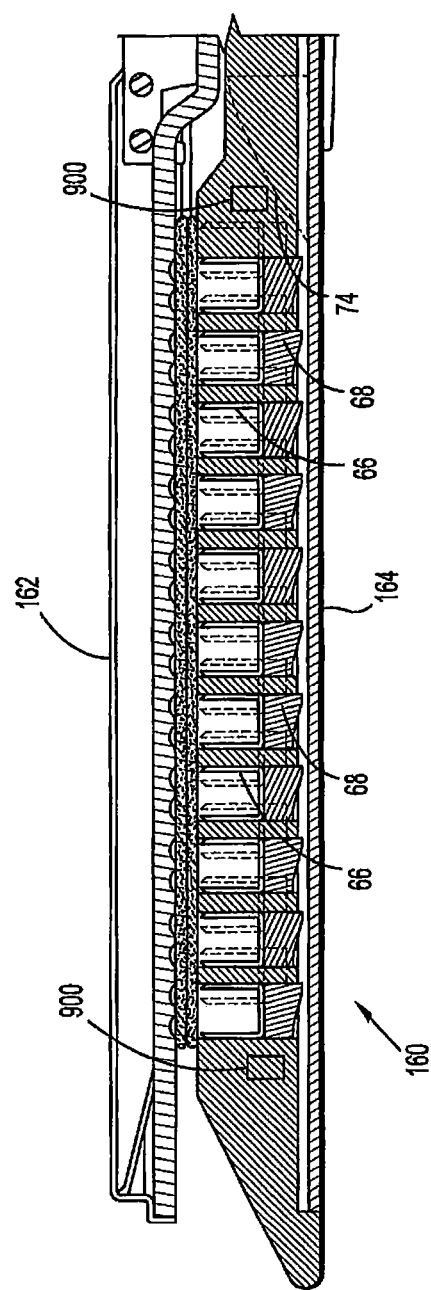
FIG. 9 is a side cross-sectional view of an end effector of the powered surgical instrument of FIG. 1 in accordance with an embodiment of the present disclosure.

Rotation of drive tube 210 in a first direction (e.g., counter-clockwise) corresponds with distal translation of the firing rod 220 which actuates jaw members 162, 164 of the end effector 160 to grasp or clamp tissue held therebetween. Additional distal translation of firing rod 220 ejects surgical fasteners from the end effector 160 to fasten tissue by actuating cam bars and/or an actuation sled 74 (FIG. 9). Further, the firing rod 220 may also be configured to actuate a knife (not explicitly shown) to sever tissue. Proximal translation of firing rod 220 corresponding with rotation of the drive tube 210 in a second direction (e.g., clockwise) actuates jaw members 162, 164 and/or knife to retract or return to corresponding pre-fired positions. Further details of firing and otherwise actuating end effector 160 are described in detail in commonly-owned U.S. Pat. No. 6,953,139 to Milliman et al. ("the '139 Milliman Patent"), the disclosure of which is hereby incorporated by reference herein.

Figure 8:
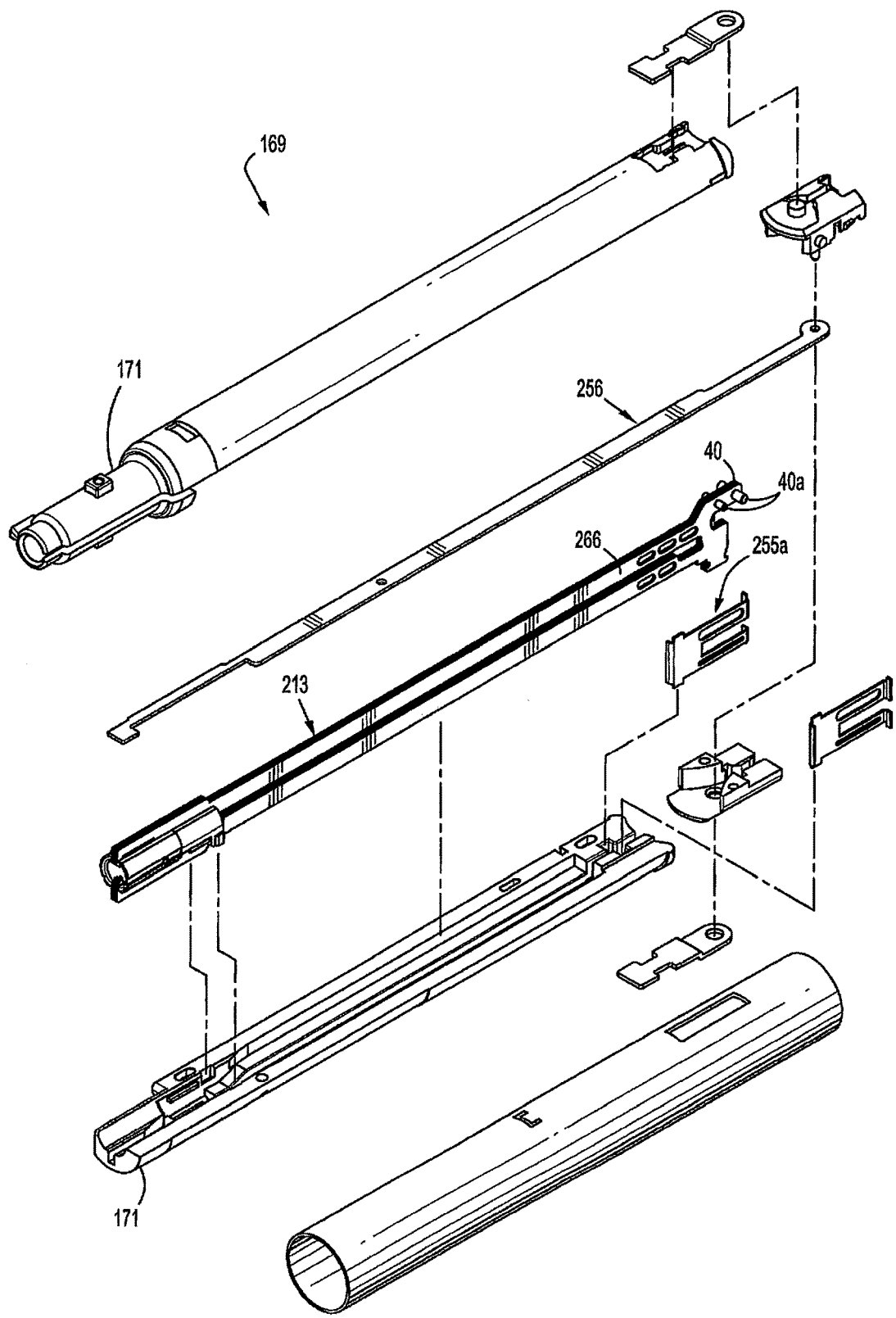
FIG. 8 is a perspective view of the mounting assembly and the proximal body portion of a loading unit with parts separated of the powered surgical instrument of FIG. 1 in accordance with an embodiment of the present disclosure.

FIG. 8 shows an exploded view of the loading unit 169. The end effector 160 may be actuated by an axial drive assembly 213 having a drive beam or drive beam 266. The distal end of the drive beam 213 may include a knife blade. In addition, the drive beam 213 includes a retention flange 40 having a pair of cam members 40a which engage the anvil and the cartridge assembly 162 and 164 during advancement of the drive beam 213 longitudinally. The drive beam 213 advances an actuation sled 74 longitudinally through the staple cartridge 164. The sled 74 has cam wedges for engaging pushers 68 disposed in slots of the cartridge assembly 164, as the sled 74 is advanced. Staples 66 disposed in the slots are driven through tissue and against the anvil assembly 162 by the pushers 68.

With reference to FIG. 8, a drive motor shaft 202 is shown extending from a planetary gear 204 that is attached to drive motor 200. Drive motor shaft 202 is in mechanical cooperation with clutch 300. Drive motor shaft 202 is rotated by the drive motor 200, thus resulting in rotation of clutch 300. Clutch 300 includes a clutch plate 302 and a spring 304 and is shown having wedged portions 306 disposed on clutch plate 302, which are configured to mate with an interface (e.g., wedges 214) disposed on a proximal face 216 of drive tube 210.

Spring 304 is illustrated between planetary gear 204 and drive tube 210. Specifically, and in accordance with the embodiment illustrated in FIG. 8, spring 304 is illustrated between clutch face 302 and a clutch washer 308. Additionally, drive motor 200 and planetary gear 204 are mounted on a motor mount 310. As illustrated in FIG. 8, motor mount 310 is adjustable proximally and distally with respect to housing 110 via slots 312 disposed in motor mount 310 and protrusions 314 disposed on housing 110.

In an embodiment of the disclosure, the clutch 300 is implemented as a slip unidirectional clutch to limit torque and high inertia loads on the drive components. Wedged portions 306 of clutch 300 are configured and arranged to slip with respect to wedges 214 of proximal face 216 of drive tube 210 unless a threshold force is applied to clutch plate 302 via clutch spring 304. Further, when spring 304 applies the threshold force needed for wedged portions 306 and wedges 214 to engage without slipping, drive tube 210 will rotate upon rotation of drive motor 200. It is envisioned that wedged portions 306 and/or wedges 214 are configured to slip in one and/or both directions (i.e., clockwise and/or counter-clockwise) with respect to one another until a threshold force is attained.

Figure 11:
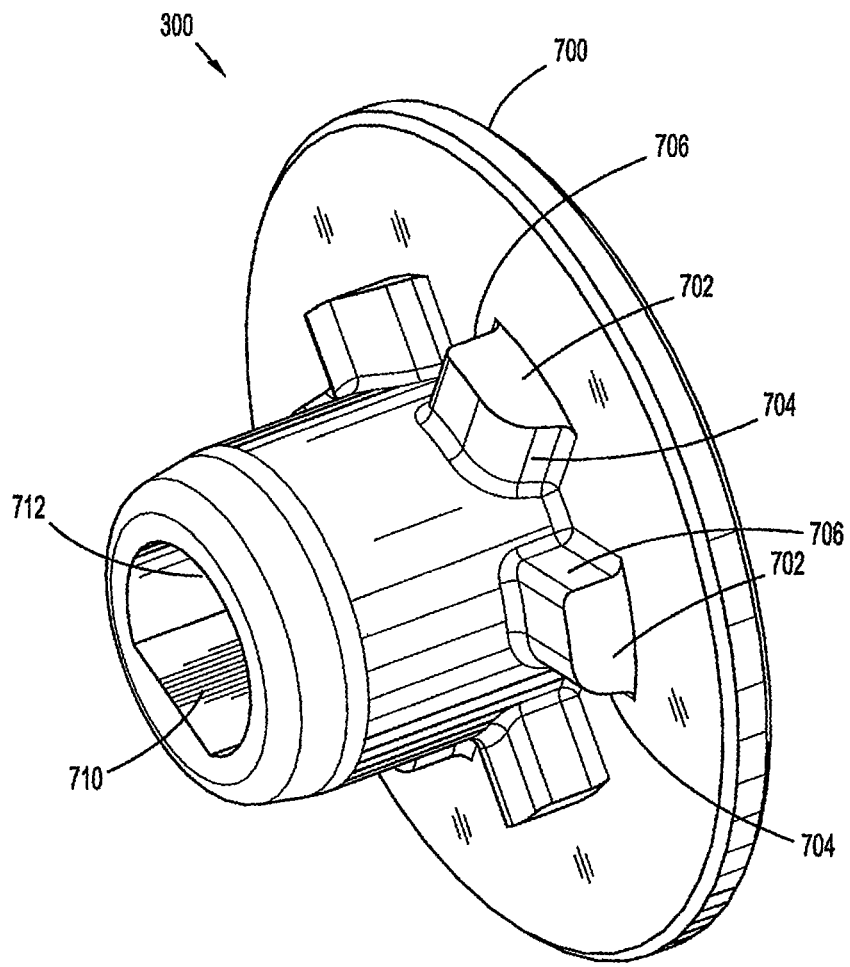
FIG. 11 is a perspective view of a unidirectional clutch plate of the powered surgical instrument of FIG. 1 in accordance with an embodiment of the present disclosure.
Figure 12:
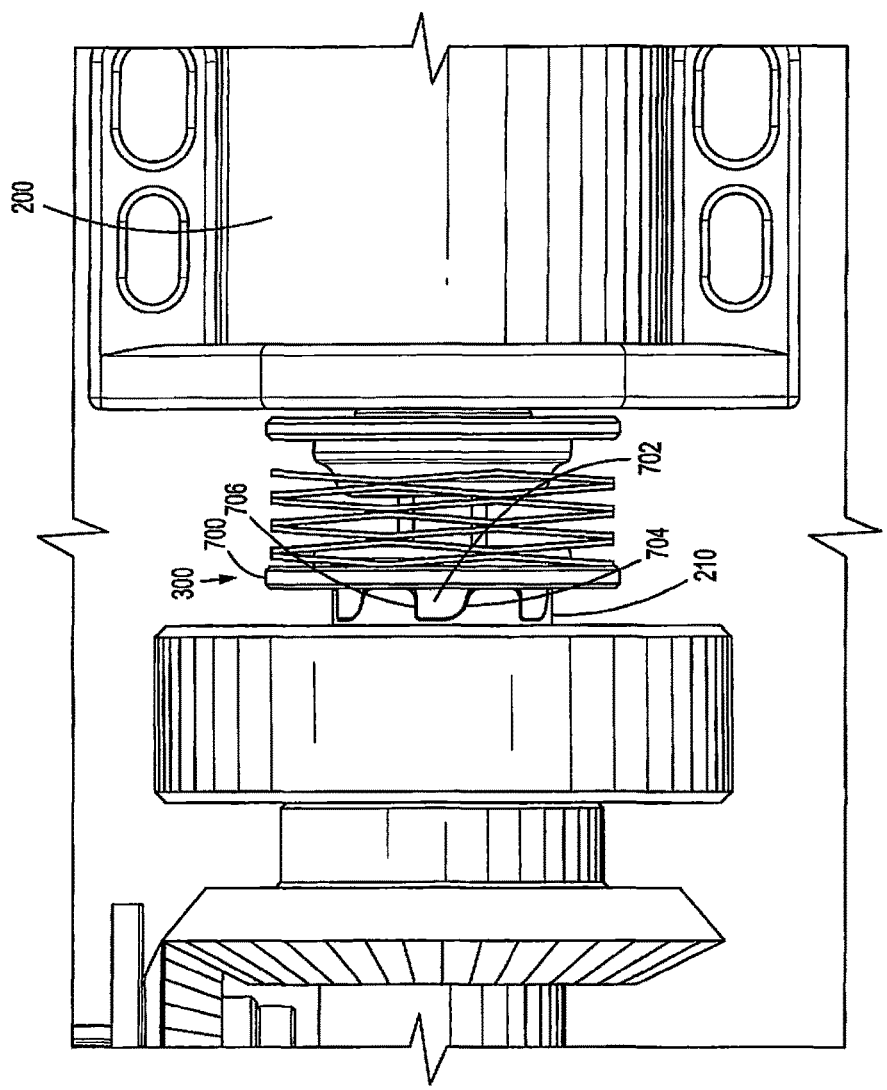
FIG. 12 is a partial enlarged side view showing internal components of the powered surgical instrument according to the embodiment of the present disclosure of FIG. 1.
Figure 13:
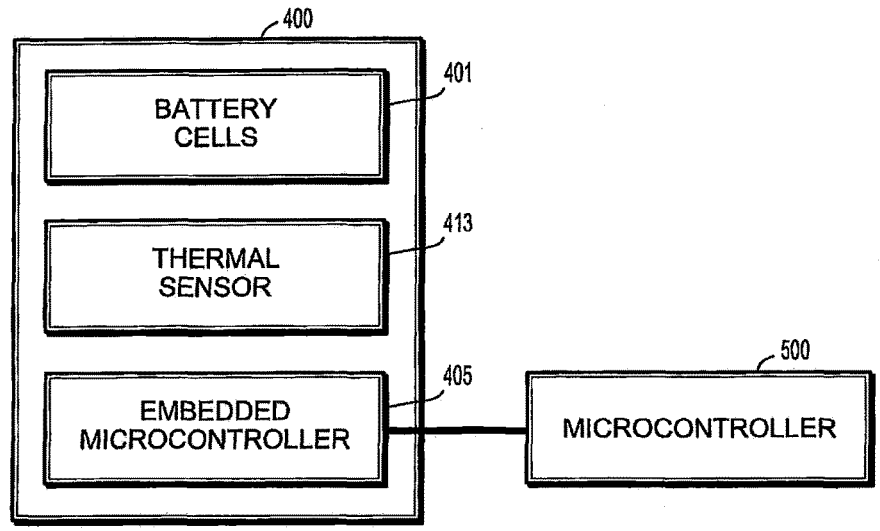
FIG. 13 is a schematic diagram of a power source of the powered surgical instrument according to the embodiment of the present disclosure of FIG. 1.

As illustrated in FIGS. 11 and 12, the clutch 300 is shown with a unidirectional clutch plate 700. The clutch plate 700 includes a plurality of wedged portions 702 having a slip face 704 and a grip face 706. The slip face 704 has a curved edge which engages the wedges 214 of the drive tube 210 up to a predetermined load. The grip face 706 has a flat edge which fully engages the drive tube 210 and prevents slippage. When the clutch plate 700 is rotated in a first direction (e.g., clockwise) the grip face 706 of the wedged portions 702 engage the wedges 214 without slipping, providing for full torque from the drive motor 200. When the clutch plate 700 is rotated in a reverse direction (e.g., counterclockwise) the slip face 704 of the wedged portions 702 engage the wedges 214 and limit the torque being transferred to the drive tube 210. Thus, if the load being applied to the slip face 704 is over the limit, the clutch 300 slips and the drive tube 210 is not rotated. This prevents high load damage to the end effector 160 or tissue which can occur due to the momentum and dynamic friction of the drive components. More specifically, the drive mechanism of the instrument 10 can drive the drive rod 220 in a forward direction with less torque than in reverse. Use of a unidirectional clutch eliminates this problem. In addition, an electronic clutch may also be used to increase the motor potential during retraction (e.g., driving the drive rod 220 in reverse) as discussed in more detail below.

It is further envisioned that drive motor shaft 202 includes a D-shaped cross-section 708, which includes a substantially flat portion 710 and a rounded portion 712. Thus, while drive motor shaft 202 is translatable with respect to clutch plate 302, drive motor shaft 202 will not "slip" with respect to clutch plate 302 upon rotation of drive motor shaft 202. That is, rotation of drive motor shaft 202 will result in a slip-less rotation of clutch plate 302.

The loading unit, in certain embodiments according to the present disclosure, includes an axial drive assembly that cooperates with firing rod 220 to approximate anvil assembly 162 and cartridge assembly 164 of end effector 160, and fire staples 66 from the staple cartridge. The axial drive assembly may include a beam that travels distally through the staple cartridge and may be retracted after the staples 66 have been fired, as discussed above and as disclosed in certain embodiments of the '139 Milliman Patent.

With reference to FIG. 4, the instrument 10 includes a power source 400 which may be a rechargeable battery (e.g., lead-based, nickel-based, lithium-ion based, etc.). It is also envisioned that the power source 400 includes at least one disposable battery. The disposable battery may be between about 9 volts and about 30 volts.

The power source 400 includes one or more battery cells 401 depending on the current load needs of the instrument 10. Further, the power source 400 includes one or more ultracapacitors 402 which act as supplemental power storage due to their much higher energy density than conventional capacitors. Ultracapacitors 402 can be used in conjunction with the cells 401 during high energy draw. The ultracapacitors 402 can be used for a burst of power when energy is desired/required more quickly than can be provided solely by the cells 401 (e.g., when clamping thick tissue, rapid firing, clamping, etc.), as cells 401 are typically slow-drain devices from which current cannot be quickly drawn. This configuration can reduce the current load on the cells thereby reducing the number of cells 401. It is envisioned that cells 401 can be connected to the ultracapacitors 402 to charge the capacitors.

The power source 400 may be removable along with the drive motor 200 to provide for recycling of these components and reuse of the instrument 10. In another embodiment, the power source 400 may be an external battery pack which is worn on a belt and/or harness by the user and wired to the instrument 10 during use.

The power source 400 is enclosed within an insulating shield 404 which may be formed from an absorbent, flame resistant and retardant material. The shield 404 prevents heat generated by the power source 400 from heating other components of the instrument 10. In addition, the shield 404 may also be configured to absorb any chemicals or fluids which may leak from the cells 402 during heavy use and/or damage.

The power source 400 is coupled to a power adapter 406 which is configured to connect to an external power source (e.g., DC transformer). The external power source may be used to recharge the power source 400 or provide for additional power requirements. The power adapter 406 may also be configured to interface with electrosurgical generators which can then supply power to the instrument 10. In this configuration, the instrument 10 also includes an AC-to-DC power source which converts RF energy from the electrosurgical generators and powers the instrument 10.

In another embodiment the power source 400 is recharged using an inductive charging interface. The power source 400 is coupled to an inductive coil (not explicitly shown) disposed within the proximal portion of the housing 110. Upon being placed within an electromagnetic field, the inductive coil converts the energy into electrical current that is then used to charge the power source 400. The electromagnetic field may be produced by a base station (not explicitly shown) which is configured to interface with the proximal portion of the housing 110, such that the inductive coil is enveloped by the electromagnetic field. This configuration eliminates the need for external contacts and allows for the proximal portion of the housing 110 to seal the power source 400 and the inductive coil within a water-proof environment which prevents exposure to fluids and contamination.

With reference to FIG. 5, the instrument 10 also includes one or more safety circuits such as a discharge circuit 410 and a motor and battery operating module 412. For clarity, wires and other circuit elements interconnecting various electronic components of the instrument 10 are not shown, but such electromechanical connections wires are contemplated by the present disclosure. Certain components of the instrument 10 communicate wirelessly.

The discharge circuit 410 is coupled to a switch 414 and a resistive load 417 which are in turn coupled to the power source 400. The switch 414 may be a user activated or an automatic (e.g., timer, counter) switch which is activated when the power source 400 needs to be fully discharged for a safe and low temperature disposal (e.g., at the end of surgical procedure). Once the switch 414 is activated, the load 417 is electrically connected to the power source 400 such that the potential of the power source 400 is directed to the load 417. The automatic switch may be a timer or a counter which is automatically activated after a predetermined operational time period or number of uses to discharge the power source 400. The load 417 has a predetermined resistance sufficient to fully and safely discharge all of the cells 401.

The motor and battery operating module 412 is coupled to one or more thermal sensors 413 which determine the temperature within the drive motor 200 and the power source 400 to ensure safe operation of the instrument 10. The sensors may be an ammeter for determining the current draw within the power source 400, a thermistor, a thermopile, a thermocouple, a thermal infrared sensor and the like. Monitoring temperature of these components allows for a determination of the load being placed thereon. The increase in the current flowing through these components causes an increase in temperature therein. The temperature and/or current draw data may then be used to control the power consumption in an efficient manner or assure safe levels of operation.

In order to ensure safe and reliable operation of the instrument 10, it is desirable to ensure that the power source 400 is authentic and/or valid (e.g., conforms to strict quality and safety standards) and operating within a predetermined temperature range. Authentication that the power source 400 is valid minimizes risk of injury to the patient and/or the user due to poor quality.

With reference to FIG. 9, the power source 400 is shown having one or more battery cells 401, a temperature sensor 403 and an embedded microcontroller 405 coupled thereto. The microcontroller 405 is coupled through wired and/or wireless communication protocols to microcontroller 500 (FIG. 14) of the instrument 10 to authenticate the power source 400. In one embodiment, the temperature sensor 403 can be coupled directly to the microcontroller 500 instead of being coupled to the embedded microcontroller 405. The temperature sensor 403 may be a thermistor, a thermopile, a thermocouple, a thermal infrared sensor, a resistance temperature detector, linear active thermistor, temperature-responsive color changing strips, bimetallic contact switches, and the like. The temperature sensor 403 reports the measured temperature to the microcontroller 405 and/or microcontroller 500.

Figure 10:
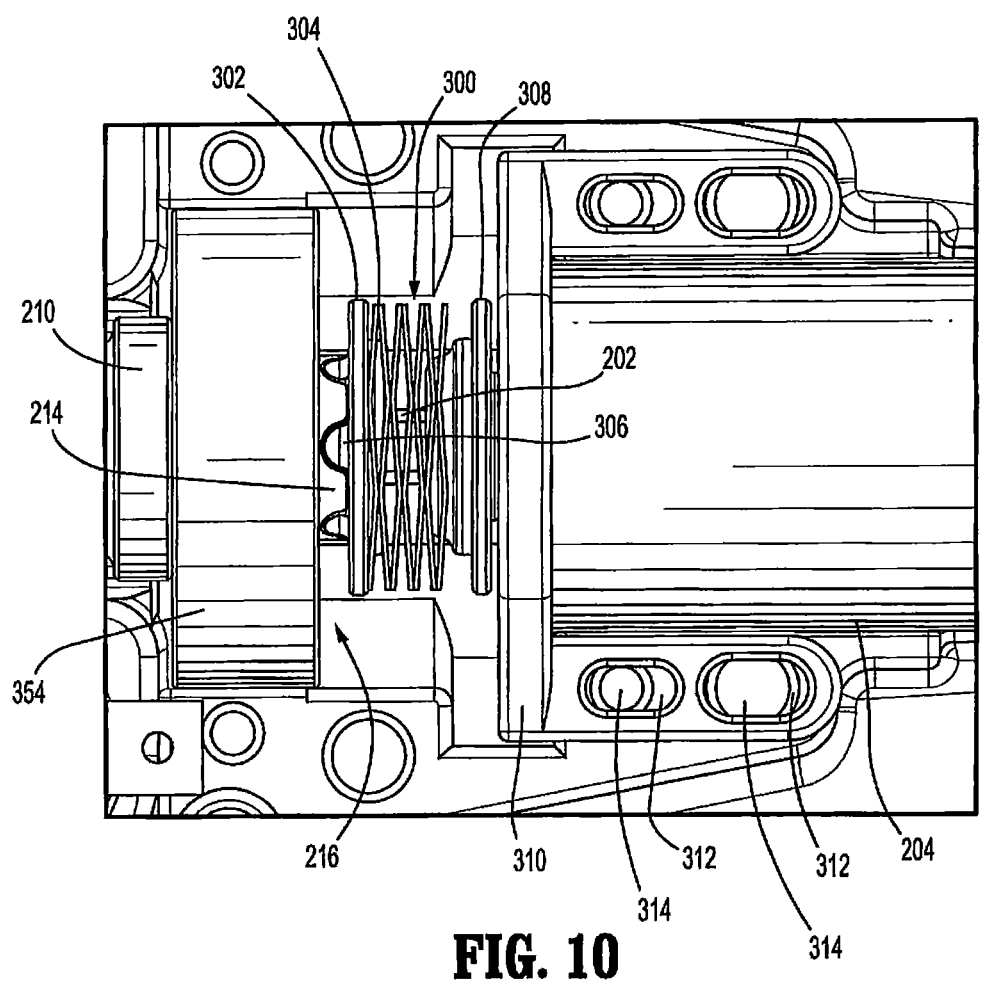
FIG. 10 is a partial enlarged side view showing internal components of the powered surgical instrument according to the embodiment of the present disclosure of FIG. 1.

The embedded microcontroller 405 executes a so-called challenge-response authentication algorithm with the microcontroller 500 which is illustrated in FIG. 10. In step 630, the power source 400 is connected to the instrument 10 and the instrument 10 is switched on. The microcontroller 500 sends a challenge request to the embedded microcontroller 405. In step 632, the microcontroller 405 interprets the challenge request and generates a response as a reply to the request. The response may include an identifier, such as a unique serial number stored in a radio frequency identification tag or in memory of the microcontroller 405, or a unique electrical measurable value of the power source 400 (e.g., resistance, capacitance, inductance, etc.). In addition, the response includes the temperature measured by the temperature sensor 403.

In step 634, the microcontroller 500 decodes the response to obtain the identifier and the measured temperature. In step 636, the microcontroller 500 determines if the power source 400 is authentic based on the identifier, by comparing the identifier against a pre-approved list of authentic identifiers. If the identifier is not valid, the instrument 10 is not going to operate and displays a "failure to authenticate battery" message via the user interface 120. If the identifier is valid, the process proceeds to step 640 where the measured temperature is analyzed to determine if the measurement is within a predetermined operating range. If the temperature is outside the limit, the instrument 10 also displays the failure message. Thus, if the temperature is within the predetermined limit and the identifier is valid, in step 642, the instrument commences operation, which may include providing a "battery authenticated" message to the user.

Referring back to FIGS. 4 and 5 a plurality of sensors for providing feedback information relating to the function of the instrument 10 are illustrated. Any combination of sensors may be disposed within the instrument 10 to determine its operating stage, such as, staple cartridge load detection as well as status thereof, articulation, clamping, rotation, stapling, cutting and retracting, and the like. The sensors can be actuated by proximity, displacement or contact of various internal components of the instrument 10 (e.g., firing rod 220, drive motor 200, etc.).

In the illustrated embodiments, the sensors can be rheostats (e.g., variable resistance devices), current monitors, conductive sensors, capacitive sensors, inductive sensors, thermal-based sensors, limit actuated switches, multiple position switch circuits, pressure transducers, linear and/or rotary variable displacement transducers, linear and/or rotary potentiometers, optical encoders, ferromagnetic sensors, Hall Effect sensors, and/or proximity switches. The sensors measure rotation, velocity, acceleration, deceleration, linear and/or angular displacement, detection of mechanical limits (e.g., stops), etc. This is attained by implementing multiple indicators arranged in either linear or rotational arrays on the mechanical drive components of the instrument 10. The sensors then transmit the measurements to the microcontroller 500 which determines the operating status of the instrument 10. In addition, the microcontroller 500 also adjusts the motor speed or torque of the instrument 10 based on the measured feedback.

In embodiments where the clutch 300 is implemented as a slip clutch as shown in FIG. 11, linear displacement sensors (e.g., linear displacement sensor 237) are positioned distally of the clutch 300 to provide accurate measurements. In this configuration, slippage of the clutch 300 does not affect the position, velocity and acceleration measurements recorded by the sensors.

With reference to FIG. 4, a load switch 230 is disposed within the articulation housing 172. The switch 230 is connected in series with the switch 114, preventing activation of the instrument 10 unless the loading unit 169 is properly loaded into the instrument 10. If the loading unit 169 is not loaded into the instrument 10, the main power switch (e.g., switch 114) is open, thereby preventing use of any electronic or electric components of the instrument 10. This also prevents any possible current draw from the power source 400 allowing the power source 400 to maintain a maximum potential over its specified shelf life.

Thus, the switch 230 acts as a so-called "lock-out" switch which prevents false activation of the instrument 10 since the switch is inaccessible to external manipulation and can only be activated by the insertion of the loading unit 169. The switch 230 is activated by displacement of a plunger or sensor tube as the loading unit 169 is inserted into the endoscopic portion 140. Once the switch 230 is activated, the power from the power source 400 is supplied to the electronic components (e.g., sensors, microcontroller 500, etc.) of the instrument 10 providing the user with access to the user interface 120 and other inputs/outputs. This also activates the visual outputs 123 to light up according to the light combination indicative of a properly loaded loading unit 169 wherein all the lights are off as described in Table 1.

Figure 18:
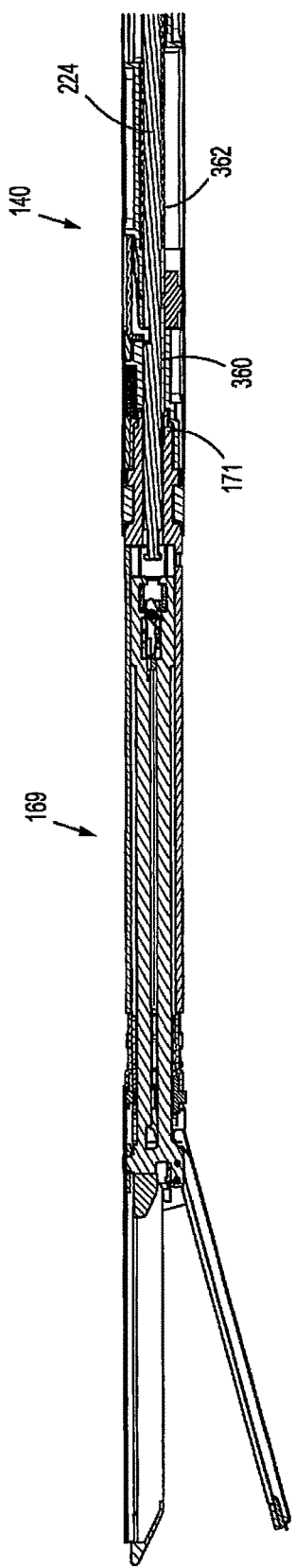
FIG. 18 is a side cross-sectional view of the end effector of the powered surgical instrument of FIG. 1 in accordance with an embodiment of the present disclosure.
Figure 19:
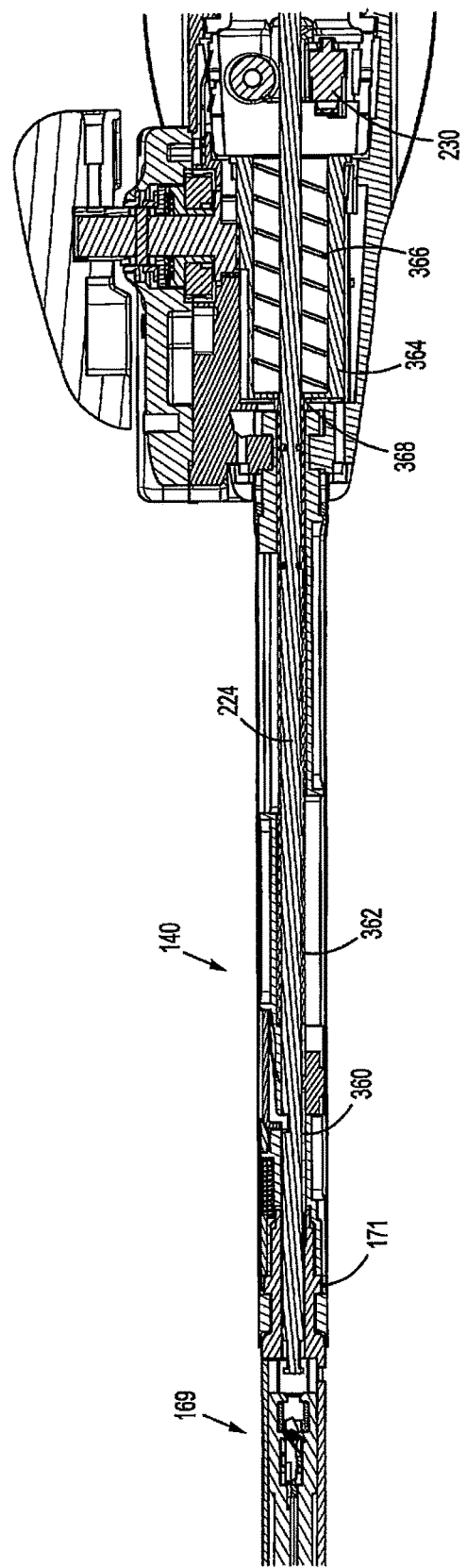
FIG. 19 is a side cross-sectional view of the powered surgical instrument of FIG. 1 in accordance with an embodiment of the present disclosure.

More specifically, as shown in FIGS. 18 and 19, the endoscopic portion 140 includes a sensor plate 360 therein which is in mechanical contact with a sensor tube also disposed within the endoscopic portion 140 and around the distal portion 224 of firing rod 220. The distal portion 224 of the firing rod 220 passes through an opening 368 at a distal end of a sensor cap 364. The sensor cap 364 includes a spring and abuts the switch 230. This allows the sensor cap 364 to be biased against the sensor tube 362 which rests on the distal end of the sensor cap 364 without passing through the opening 368. Biasing of the sensor tube 362 then pushes out the sensor plate 360 accordingly.

When the loading unit 169 is loaded into the endoscopic portion 140, the proximal portion 171 abuts the sensor plate 360 and displaces the plate 360 in a proximal direction. The sensor plate 360 then pushes the sensor tube 362 in the proximal direction which then applies pressure on the sensor cap 364 thereby compressing the spring 366 and activating the switch 230 denoting that the loading unit 169 has been properly inserted.

Once the loading unit 169 is inserted into the endoscopic portion, the switch 230 also determines whether the loading unit 169 is loaded correctly based on the position thereof. If the loading unit 169 is improperly loaded, the switch 114 is not activated and an error code is relayed to the user via the user interface 120 (e.g., all the lights are off as described in Table 1). If the loading unit 169 has already been fired, any mechanical lockouts have been previously activated or the staple cartridge has been used, the instrument 10 relays the error via the user interface 120, e.g., the first light 123a is flashing.

In one embodiment, a second lock-out switch 259 (FIG. 4) coupled to the main switch 114 may be implemented in the instrument 10 as a bioimpedance, capacitance or pressure sensor disposed on the top surface of the handle portion 112 configured to be activated when the user grasps the instrument 10. Thus, unless the instrument 10 is grasped properly, the operation of the switch 114 is disabled.

With reference to FIG. 6, the instrument 10 includes a position calculator 416 for determining and outputting current linear position of the firing rod 220. The position calculator 416 is electrically connected to a linear displacement sensor 237 and a rotation speed detecting apparatus 418 is coupled to the drive motor 200. The apparatus 418 includes an encoder 420 coupled to the motor for producing two or more encoder pulse signals in response to the rotation of the drive motor 200. The encoder 420 transmits the pulse signals to the apparatus 418 which then determines the rotational speed of the drive motor 200. The position calculator 416 thereafter determines the linear speed and position of the firing rod based on the rotational speed of the drive motor 200 since the rotation speed is directly proportional to the linear speed of the firing rod 220. The position calculator 416 and the speed calculator 422 are coupled to the microcontroller 500 which controls the drive motor 200 in response to the sensed feedback form the calculators 416 and 422. This configuration is discussed in more detail below with respect to FIG. 14.

The instrument 10 includes first and second indicators 320a, 320b disposed on the firing rod 220, which determine the speed of firing rod 220 and the location of firing rod 220 with respect to drive tube 210 and/or housing 110. For instance, a limit switch may be activated (e.g., shaft start position sensor 239 and clamp position sensor 232) by sensing first and second indicators 320a and/or 320b (e.g., bumps, grooves, indentations, etc.) passing thereby to determine position of firing rod 220, speed of firing rod 220 and mode of the instrument 10 (e.g., clamping, grasping, firing, sealing, cutting, retracting). Further, the feedback received from first and second indicators 320a, 320b may be used to determine when firing rod 220 should stop its axial movement (e.g., when drive motor 200 should cease) depending on the size of the particular loading unit attached thereto.

More specifically, as the firing rod 220 is moved in the distal direction from its resting (e.g., initial) position, the first actuation of the position sensor 231 is activated by the first indicator 320a which denotes that operation of the instrument 10 has commenced. As the operation continues, the firing rod 220 is moved further distally to initiate clamping, which moves first indicator 320a to interface with clamp position sensor 232. Further advancement of the firing rod 220 moves the second indicator 320b to interface with the position sensor 232 which indicates that the instrument 10 has been fired.

As discussed above, the position calculator 416 is coupled to a linear displacement sensor 237 disposed adjacent to the firing rod 220. In one embodiment, the linear displacement sensor 237 may be a magnetic sensor. The firing rod 220 may be magnetized or may include magnetic material therein. The magnetic sensor may be a ferromagnetic sensor or a Hall Effect sensor which is configured to detect changes in a magnetic field. As the firing rod 220 is translated linearly due to the rotation of the drive motor 200, the change in the magnetic field in response to the translation motion is registered by the magnetic sensor. The magnetic sensor transmits data relating to the changes in the magnetic field to the position calculator 416 which then determines the position of the firing rod 220 as a function of the magnetic field data.

In one embodiment, a select portion of the firing rod 220 may be magnetized, such as the threads of the internally-threaded portion 212 or other notches (e.g., indicators 320a and/or 320b) disposed on the firing rod 220 may include or be made from a magnetic material. This allows for correlation of the cyclical variations in the magnetic field with each discrete translation of the threads as the magnetized portions of the firing rod 220 are linearly translated. The position calculator 416 thereafter determines the distance and the position of the firing rod 220 by summing the number of cyclical changes in the magnetic field and multiplies the sum by a predetermined distance between the threads and/or notches.

In one embodiment, the linear displacement sensor 237 may be a potentiometer or a rheostat. The firing rod 220 includes a contact (e.g., wiper terminal) disposed in electromechanical contact with the linear displacement sensor 237. The contact slides along the surface of the linear displacement sensor 237 as the firing rod 220 is moved in the distal direction by the drive motor 200. As the contact slides across the potentiometer and/or the rheostat, the voltage of the potentiometer and the resistance of the rheostat vary accordingly. Thus, the variation in voltage and resistance is transmitted to the position calculator 416 which then extrapolates the distance traveled by the firing rod 220 and/or the firing rod coupling 190 and the position thereof.

In one embodiment, the position calculator 416 is coupled to one or more switches 421 which are actuated by the threads of the internally-threaded portion 212 or the indicators 320a and/or 320b as the firing rod 220 and the firing rod coupling 190 are moved in the distal direction. The position calculator 416 counts the number of threads which activated the switch 421 and then multiplies the number by a predetermined distance between the threads or the indicators 320a and/or 320b.

The instrument 10 also includes a speed calculator 422 which determines the current speed of a linearly moving firing rod 220 and/or the torque being provided by the drive motor 200. The speed calculator 422 is connected to the linear displacement sensor 237 which allows the speed calculator 422 to determine the speed of the firing rod 220 based on the rate of change of the displacement thereof.

The speed calculator 422 is coupled to the rotation speed detecting apparatus 424 which includes the encoder 426. The encoder 426 transmits the pulses correlating to the rotation of the drive motor 200 which the speed calculator 422 then uses to calculate the linear speed of the firing rod

220. In another embodiment, the speed calculator 422 is coupled to a rotational sensor 239 which detects the rotation of the drive tube 210, thus, measuring the rate of rotation of the drive tube 210 which allows for determination of the linear velocity of the firing rod 220.

The speed calculator 422 is also coupled to a voltage sensor 428 which measures the back electromotive force ("EMF") induced in the drive motor 200. The back EMF voltage of the drive motor 200 is directly proportional to the rotational speed of the drive motor 200 which, as discussed above, is used to determine the linear speed of the firing rod 220.

Monitoring of the speed of the drive motor 200 can also be accomplished by measuring the voltage across the terminals thereof under constant current conditions. An increase in a load of the drive motor 200 yields a decrease in the voltage applied at the motor terminals, which is directly related to the decrease in the speed of the motor. Thus, measuring the voltage across the drive motor 200 provides for determining the load being placed thereon. In addition, by monitoring the change of the voltage over time (dV/dt), the microprocessor 500 can detect a quick drop in voltage which correlates to a large change in the load or an increase in temperature of the drive motor 200 and/or the power source 400.

In a further embodiment, the speed calculator 422 is coupled to a current sensor 430 (e.g., an ammeter). The current sensor 430 is in electrical communication with a shunt resistor 432 which is coupled to the drive motor 200. The current sensor 430 measures the current being drawn by the drive motor 200 by measuring the voltage drop across the resistor 432. Since the current used to power the drive motor 200 is proportional to the rotational speed of the drive motor 200 and, hence, the linear speed of the firing rod 220, the speed calculator 422 determines the speed of the firing rod 220 based on the current draw of the drive motor 200.

The speed calculator 422 may also be coupled to a second voltage sensor (not explicitly shown) for determining the voltage within the power source 400 thereby calculating the power draw directly from the source. In addition, the change in current over time (dI/dt) can be monitored to detect quick spikes in the measurements which correspond to a large increase in applied torque by the drive motor 200. Thus, the current sensor 430 is used to determine the speed and the load of the drive motor 200.

In addition, the velocity of the firing rod 220 as measured by the speed calculator 422 may be then compared to the current draw of the drive motor 200 to determine whether the drive motor 200 is operating properly. Namely, if the current draw is not commensurate (e.g., large) with the velocity (e.g., low) of the firing rod 220 then the motor 200 is malfunctioning (e.g., locked, stalled, etc.). If a stall situation is detected, or the current draw exceeds predetermined limits, the position calculator 416 then determines whether the firing rod 220 is at a mechanical stop. If this is the case, then the microcontroller 500 can shut down the drive motor 200 or enters a pulse and/or pause mode (e.g., discontinuous supply of power to the drive motor 200) to unlock the instrument 10 and retract the firing rod 220.

In one embodiment, the speed calculator 422 compares the rotation speed of the drive tube 210 as detected by the rotation sensor 239 and that of the drive motor 200 based on the measurements from and the rotation speed detecting apparatus 424. This comparison allows the speed calculator 422 to determine whether there is a clutch activation problem (e.g., slippage) if there is a discrepancy between the rotation of the clutch 300 and that of the drive tube 210. If slippage is detected, the position calculator 416 then determines whether the firing rod 220 is at a mechanical stop. If this is the case, then the microcontroller 500 can shut down the instrument 10 or enter a pulse and/or pause mode (e.g., discontinuous supply of power to the drive motor 200), or retract the firing rod 220.

In addition to linear and/or rotational displacement of the firing rod 220 and other drive components, the instrument 10 also includes sensors adapted to detect articulation of the end effector 160. With reference to FIG. 4, the instrument 10 includes a rotation sensor 241 adapted to indicate the start position, the rotational direction and the angular displacement of the rotating housing assembly 180 at the start of the procedure as detected by the shaft start position sensor 231. The rotation sensor 241 operates by counting the number of indicators disposed on the inner surface of the rotation knob 182 as the rotation knob 182 is rotated. The count is then transmitted to the microcontroller 500 which then determines the rotational position of the endoscopic portion 142. This can be communicated wirelessly or through an electrical connection on the endoscopic portion and wires to the microcontroller 500.

The instrument 10 also includes an articulation sensor 235 which determines articulation of the end effector 160. The articulation sensor 235 counts the number of teeth 263 disposed on the articulation gear 233 by which the articulation knob 176 has been rotated from its 0° position, namely the center position of the articulation knob 176 and, hence, of the end effector 160 as shown in FIG. C. The 0° position and can be designated by a central unique indicator 265 also disposed on the articulation gear 233 which corresponds with the first position of the end effector 160, where longitudinal axis B-B is substantially aligned with longitudinal axis A-A. The count is then transmitted to the microcontroller 500 which then determines the articulation position of the end effector 160 and reports the articulation angle via the interface 120.

In addition, the articulation angle can be used for the so-called "auto stop" mode. During this operational mode, the instrument 10 automatically stops the articulation of the end effector 160 when the end effector 160 is at its central first position. Namely, as the end effector 160 is articulated from a position in which longitudinal axis B-B is disposed at an angle to longitudinal axis A-A towards the first position, the articulation is stopped when the longitudinal axis B-B is substantially aligned with longitudinal axis A-A. This position is detected by the articulation sensor 235 based on the central indicator. This mode allows the endoscopic portion 140 to be extracted without the user having to manually align the end effector 160.

With reference to FIG. 1, the present disclosure provides a loading unit identification system 440 which allows the instrument 10 to identify the loading unit 169 and to determine operational status thereof. The identification system 440 provides information to the instrument 10 on staple size, cartridge length, type of the loading unit 169, status of cartridge, proper engagement, and the like. This information allows the instrument to adjust clamping forces, speed of clamping, and firing and end of stroke for various length staple cartridges.

Figure 16:
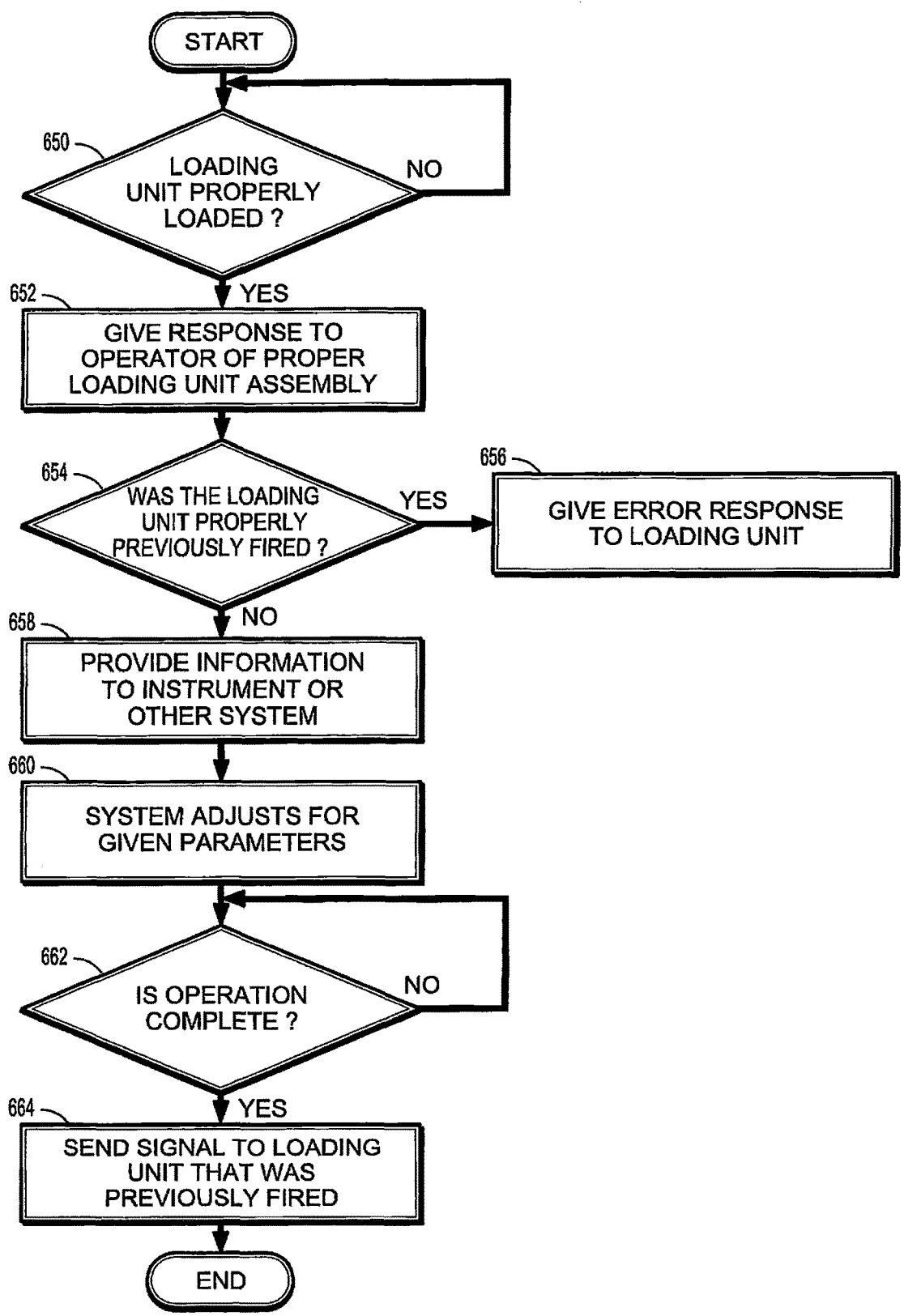
FIG. 16 is a flow chart diagram illustrating a method for authenticating the loading unit of the powered surgical instrument according to the embodiment of the present disclosure of FIG. 1.
Figure 17:
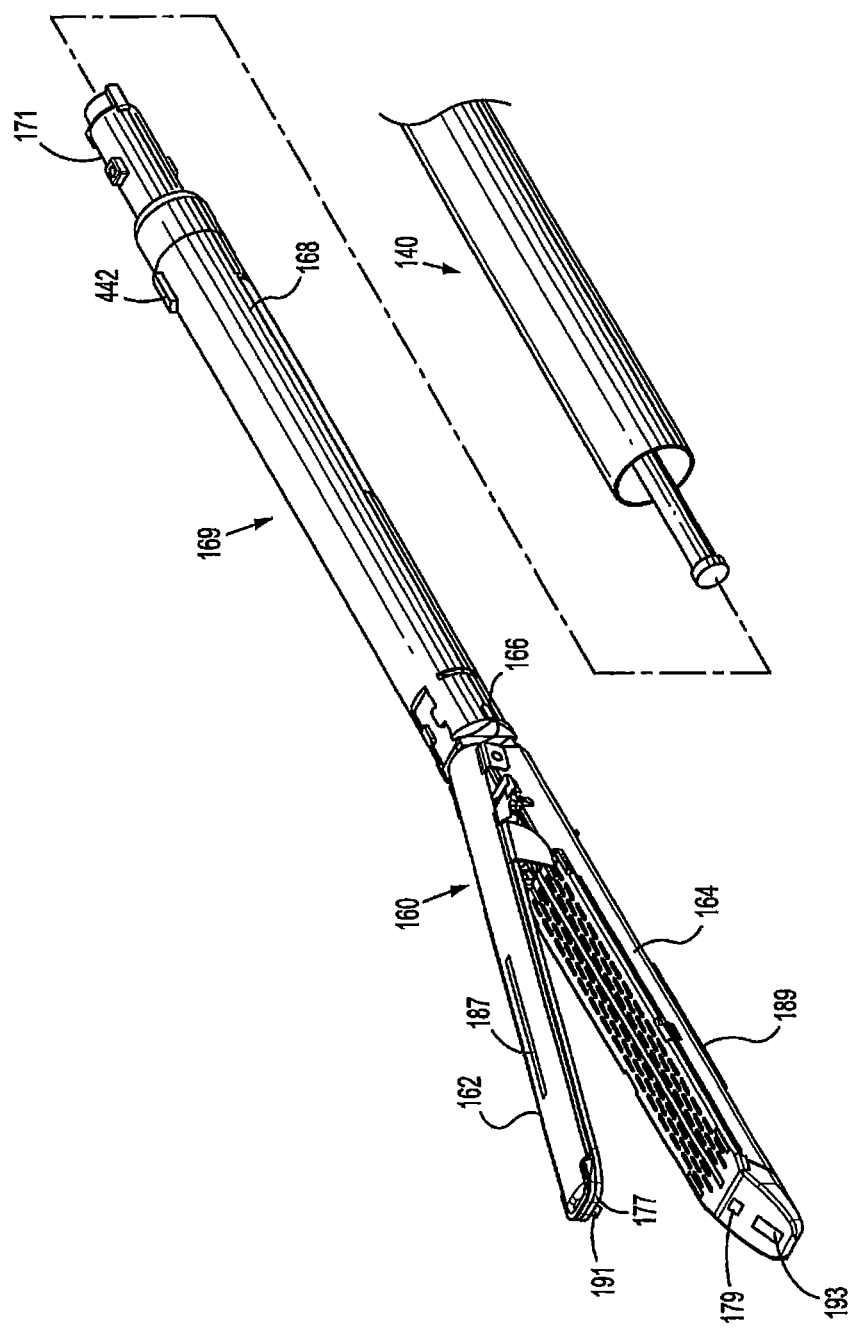
FIG. 17 is a perspective view of the loading unit of the powered surgical instrument according to the embodiment of the present disclosure of FIG. 1.

The loading unit identification system 440 may also be adapted to determine and communicate to the instrument 10 (e.g., a control system 501 shown in FIG. 14) various information, including the speed, power, torque, clamping, travel length, and/or strength limitations for operating the particular end effector 160. The control system 501 may also determine the operational mode and adjust the voltage, clutch spring loading, and/or stop points for travel of the components. More specifically, the identification system may include a component (e.g., a microchip, emitter or transmitter) disposed in the end effector 160 that communicates (e.g., wirelessly, via infrared signals, etc.) with the control system 501, or a receiver therein. It is also envisioned that a signal may be sent via firing rod 220, such that firing rod 220 functions as a conduit for communications between the control system 501 and end effector 160. In another embodiment, the signals can be sent through an intermediate interface, such as a feedback controller 603 (FIGS. 15-17).

By way of example, the sensors discussed above may be used to determine if the staples 66 have been fired from the staple cartridge, whether they have been fully fired, whether and the extent to which the beam has been retracted proximally through the staple cartridge, and other information regarding the operation of the loading unit. In certain embodiments of the present disclosure, the loading unit incorporates components for identifying the type of loading unit, and/or staple cartridge loaded on the instrument 10, including infra red, cellular, or radio frequency identification chips. The type of loading unit and/or staple cartridge may be received by an associated receiver within the control system 501, or an external device in the operating room for providing feedback, control and/or inventory analysis.

Information can be transmitted to the instrument 10 via a variety of communication protocols (e.g., wired or wireless) between the loading unit 169 and the instrument 10. The information can be stored within the loading unit 169 in a microcontroller, microprocessor, non-volatile memory, radio frequency identification tags, and/or identifiers of various types such as optical, color, displacement, magnetic, electrical, binary and/or gray coding (e.g., conductance, resistance, capacitance, impedance).

In one embodiment, the loading unit 169 and the instrument 10 include corresponding wireless transceivers, an identifier 442, and an interrogator 444. The identifier 442 includes memory or may be coupled to a microcontroller for storing various identification and status information regarding the loading unit 169. Once the loading unit 169 is coupled to the instrument 10, the instrument 10 interrogates the identifier 442 via the interrogator 444 for an identifying code. In response to the interrogatory, the identifier 442 replies with the identifying code corresponding to the loading unit 169. During operation, once identification has occurred, the identifier 442 is configured to provide the instrument 10 with updates as to the status of the loading unit 169 (e.g., mechanical and/or electrical malfunction, position, articulation, etc.).

The identifier 442 and the interrogator 444 are configured to communicate with each other using one or more of the following communication protocols such as Bluetooth®, ANT3®, KNX®, ZWave®, X10® Wireless USB®, IrDA®, Nanonet®, Tiny OS®, ZigBee®, 802.11 IEEE, and/or other radio, infrared, UHF, VHF communications and the like. In one embodiment, the transceiver 400 may be a radio frequency identification (RFID) tag, either active or passive, depending on the interrogator capabilities of the transceiver 402.

Figure 15A:
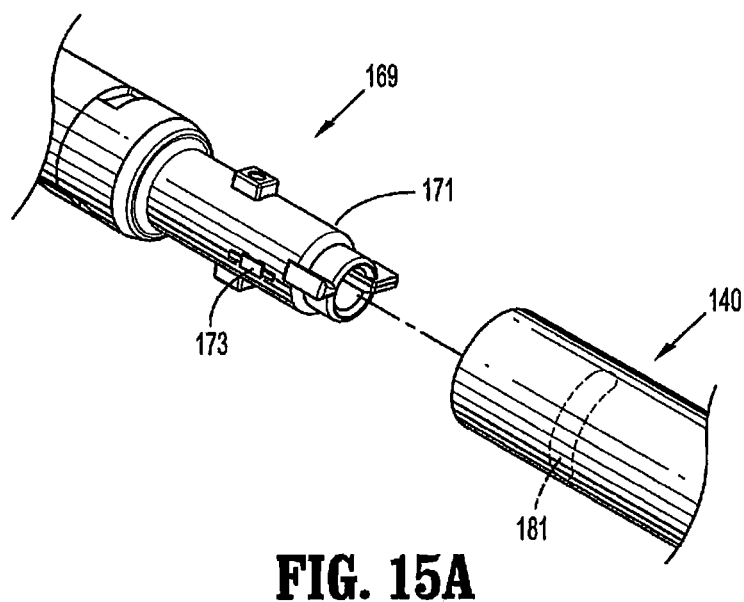
FIGS. 15A-B are partial perspective rear views of a loading unit of the powered surgical instrument according to the embodiment of the present disclosure of FIG. 1.

FIGS. 15A and B illustrate additional embodiments of the loading unit 169 having various types of identification devices. With reference to FIG. 15A, a proximal end 171 of the loading unit 169 having an electrical identifier 173 is shown. The identifier 173 may include one or more resistors, capacitors, and/or inductors and is coupled with a corresponding electrical contact 181 disposed on the distal end of the endoscopic portion 140. The contact may include slip rings, brushes and/or fixed contacts disposed in the endoscopic portion. The identifier 173 may be disposed on any location of the loading unit 168 and may be formed on a flexible or fixed circuit or may be traced directly on the surface of the loading unit 169.

When the loading unit 169 is coupled with the endoscopic portion 140, the contact applies a small current through the electrical identifier 173. The interrogator contact also includes a corresponding electrical sensor which measures the resistance, impedance, capacitance, and/or impedance of the identifier 173. The identifier 173 has a unique electrical property (e.g., resistance, capacitance, inductance, etc.) which corresponds to the identifying code of the loading unit 169, thus, when the electrical property thereof is determined, the instrument 10 determines the identity of the loading unit 169 based on the measured property.

In one embodiment, the identifier 173 may be a magnetic identifier such as gray coded magnets and/or ferrous nodes incorporating predetermined unique magnetic patterns identifying the loading unit 169 by the identifying code. The magnetic identifier is read via a magnetic sensor (e.g., ferromagnetic sensor, Hall Effect sensor, etc.) disposed at the distal end of the endoscopic portion 140. The magnetic sensor transmits the magnetic data to the instrument 10 which then determines the identity of the loading unit 169.

Figure 15B:
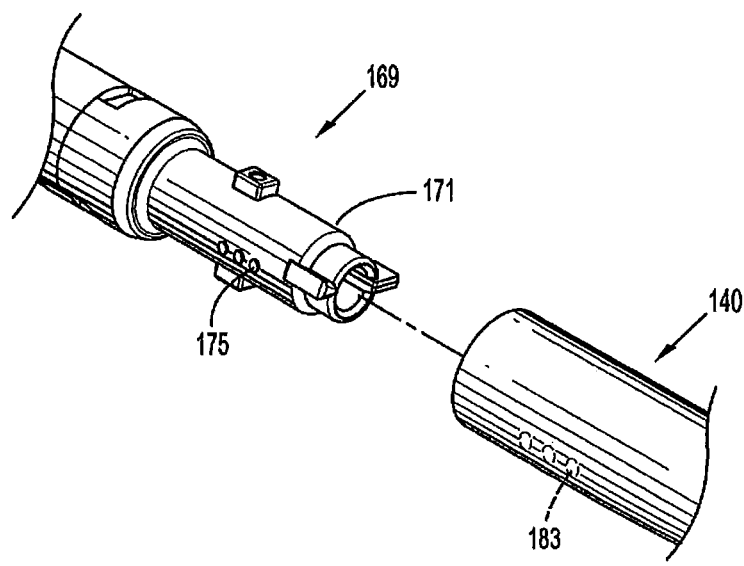

FIG. 15B illustrates the proximal end 171 of the loading unit 169 having one or more protrusions 175. The protrusions 175 can be of any shape, such as divots, bumps, strips, etc., of various dimensions. The protrusions 175 interface with corresponding displacement sensors 183 disposed within the proximal segment of the endoscopic portion 140. The sensors are displaced when the protrusions 175 are inserted into the endoscopic portion. The amount of the displacement is analyzed by the sensors and converted into identification data, allowing the instrument 10 to determine staple size, cartridge length, type of the loading unit 169, proper engagement, and the like. The displacement sensors can be switches, contacts, magnetic sensors, optical sensors, variable resistors, or linear and rotary variable displacement transducers which can be spring loaded. The switches are configured to transmit binary code to the instrument 10 based on their activation status. More specifically, some protrusions 175 extend a distance sufficient to selectively activate some of the switches, thereby generating a unique code based on the combination of the protrusions 175.

In another embodiment, the protrusion 175 can be color coded. The displacement sensors 183 include a color sensor configured to determine the color of the protrusion 175 to measure one or more properties of the loading unit 169 based on the color and transmits the information to the instrument 10.

FIG. 16 shows a method for identifying the loading unit 169 and providing status information concerning the loading unit 169 to the instrument 10. In step 650 it is determined whether the loading unit 169 is properly loaded into the instrument 10. This may be determined by detecting whether contact has been made with the identifier 173 and/or protrusions 175. If the loading unit 169 is properly loaded, in step 652, the loading unit 169 communicates to the instrument 10 a ready status (e.g., turning on the first light of the visual outputs 123).

In 654, the instrument 10 verifies whether the loading unit 169 has been previously fired. The identifier 442 stores a value indicative of the previously fired status. If the loading unit 169 was fired, in step 656, the instrument 10 provides an error response (e.g., flashing the first light of the visual outputs 123). If the loading unit 169 has not been fired, in step 658 the loading unit 169 provides identification and status information (e.g., first light is turned on) to the instrument 10 via the identification system 440. The determination whether the loading unit 169 has been fired is made based on the saved "previously fired" signal saved in the memory of the identifier 442 as discussed in more detail below with respect to step 664. In step 660, the instrument 10 adjusts its operating parameters in response to the information received from the loading unit 169.

The user performs a surgical procedure via the instrument 10 in step 662. Once the procedure is complete and the loading unit 169 has been fired, the instrument 10 transmits a "previously fired" signal to the loading unit 169. In step 664, the loading unit 169 saves the "previously fired" signal in the memory of the identifier 442 for future interrogations by the instrument 10 as discussed with respect to step 654.

With reference to FIG. 17, the loading unit 169 includes one or more tissue sensors disposed within the end effector 160 for detecting the type of object being grasped, such recognizing non-tissue objects and the tissue type of the object. The sensors are also configured to determine amount of blood flow being passed between the jaw members of the end effector 160. More specifically, a first tissue sensor 177 is disposed at a distal portion of the anvil assembly 162 and a second tissue sensor 179 is disposed at a distal portion of the cartridge assembly 164. The sensors 177 and 179 are coupled to the identifier 442 allowing for transmission of sensor data to the microcontroller 500 of the instrument 10.

The sensors 177 and 179 are adapted to generate a field and/or waves in one or more arrays or frequencies therebetween. The sensors 177 and 179 may be acoustic, ultrasonic, ferromagnetic, Hall Effect sensors, laser, infrared, radio frequency, or piezoelectric devices. The sensors 177 and 179 are calibrated for ignoring commonly occurring material, such as air, bodily fluids and various types of human tissue and for detecting certain types of foreign matter. The foreign matter may be bone, tendons, cartilage, nerves, major arteries and non-tissue matter, such as ceramic, metal, plastic, etc.

The sensors 177 and 179 detect the foreign matter passing between the anvil and cartridge assemblies 162 and 164 based on the absorption, reflection and/or filtering of the field signals generated by the sensors. If the material reduces or reflects a signal, such that the material is outside the calibration range and is, therefore, foreign, the sensors 177 and 179 transmit the interference information to the microcontroller 500 which then determines the type of the material being grasped by the end effector 160. The determination may be made by comparing the interference signals with a look up table listing various types of materials and their associated interference ranges. The microcontroller 500 then alerts the user of the foreign material being grasped as well as the identity thereof. This allows the user to prevent clamping, cutting or stapling through areas containing foreign matter.

Figure 20:
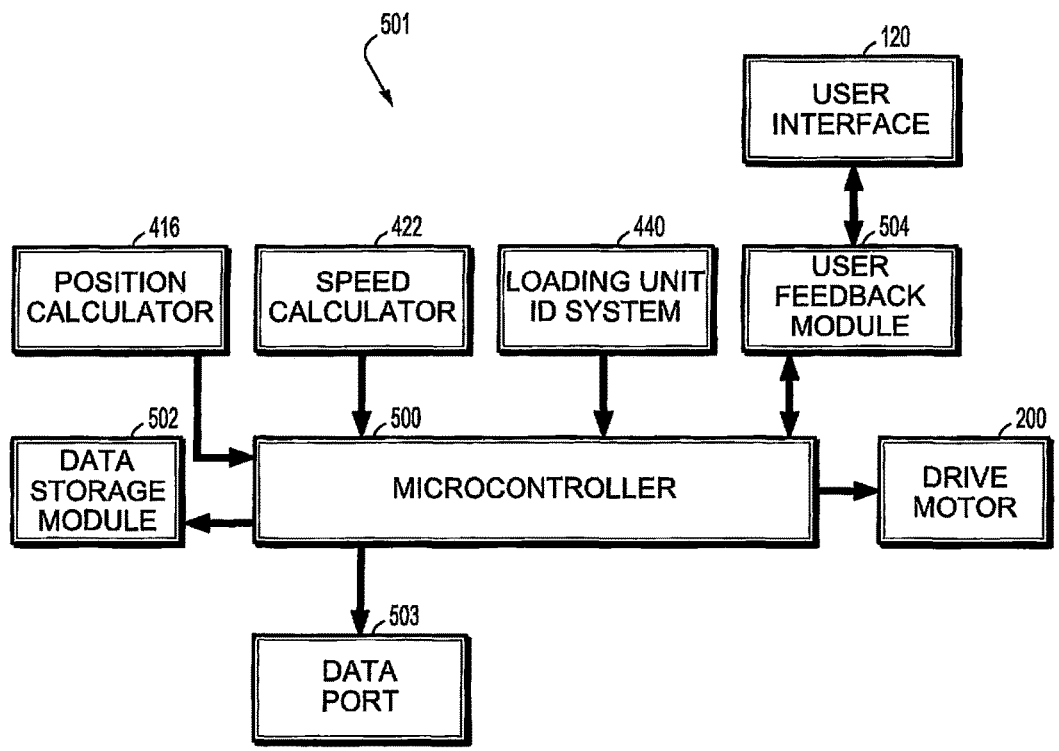
FIG. 20 is a schematic diagram of a control system of the powered surgical instrument according to the embodiment of the present disclosure of FIG. 1.

FIG. 20 illustrates a control system 501 including the microcontroller 500 which is coupled to the position and speed calculators 416 and 422, the loading unit identification system 440, the user interface 120, the drive motor 200, and a data storage module 502. In addition the microcontroller 500 may be directly coupled to various sensors (e.g., first and second tissue sensors 177 and 179, the load switch 230, shaft start position sensor 231, clamp position sensor 232, articulation sensor 235, linear displacement sensor 237, rotational sensor 239, firing rod rotation sensor 241, motor and battery operating module 412, rotation speed detecting apparatus 418, switches 421, voltage sensor 428, current sensor 430, the interrogator 444, etc.).

The microcontroller 500 includes internal memory which stores one or more software applications (e.g., firmware) for controlling the operation and functionality of the instrument 10. The microcontroller 500 processes input data from the user interface 120 and adjusts the operation of the instrument 10 in response to the inputs. The adjustments to the instrument 10 may including powering the instrument 10 on or off, speed control by means of voltage regulation or voltage pulse width modulation, torque limitation by reducing duty cycle or pulsing the voltage on and off to limit average current delivery during a predetermined period of time.

The microcontroller 500 is coupled to the user interface 120 via a user feedback module 504 which is configured to inform the user of operational parameters of the instrument 10. The user feedback module 504 instructs the user interface 120 to output operational data on the screen 122. In particular, the outputs from the sensors are transmitted to the microcontroller 500 which then sends feedback to the user instructing the user to select a specific mode, speed or function for the instrument 10 in response thereto.

The loading unit identification system 440 instructs the microcontroller 500 which end effector is on the loading unit. In an embodiment, the control system 501 is capable of storing information relating to the force applied to firing rod 220 and/or end effector 160, such that when the loading unit 169 is identified, the microcontroller 500 automatically selects the operating parameters for the instrument 10. This allows for control of the force being applied to the firing rod 220 so that firing rod 220 can drive the particular end effector 160 that is on the loading unit in use at the time.

The microcontroller 500 also analyzes the calculations from the position and speed calculators 416 and 422 and other sensors to determine the actual position and/or speed of the firing rod 220 and operating status of components of the instrument 10. The analysis may include interpretation of the sensed feedback signal from the calculators 416 and 422 to control the movement of the firing rod 220 and other components of the instrument 10 in response to the sensed signal. The microcontroller 500 is configured to limit the travel of the firing rod 220 once the firing rod 220 has moved beyond a predetermined point as reported by the position calculator 416. Additional parameters which may be used by the microcontroller 500 to control the instrument 10 include motor and/or battery temperature, number of cycles remaining and used, remaining battery life, tissue thickness, current status of the end effector, transmission and reception, external device connection status, etc.

In one embodiment, the instrument 10 includes various sensors configured to measure current (e.g., ammeter), voltage (e.g., voltmeter), proximity (e.g., optical sensors), temperature (e.g., thermocouples, thermistors, etc.), and/or force (e.g., strain gauges, load cells, etc.) to determine for loading conditions on the loading unit 169. During operation of the instrument 10 it is desirable to know the forces being exerted by the instrument 10 on the target tissue during the approximation process and during the firing process. Detection of abnormal loads (e.g., outside a predetermined load range) indicates a problem with the instrument 10 and/or clamped tissue which is communicated to the user.

Monitoring of load conditions may be performed by one or more of the following methods: monitoring speed of the drive motor 200, monitoring torque being applied by the motor, proximity of jaw members 162 and 164, monitoring temperature of components of the instrument 10, and/or measuring the load on the firing rod 220 via a strain sensor 185 (FIG. 6) and/or other load bearing components of the instrument 10. Speed and torque monitoring is discussed above with respect to FIG. 5 and the speed calculator 422.

In an embodiment, the drive motor 200 is coupled to a motor driver circuit (not shown) which controls the operation of the drive motor 200 including the flow of electrical energy from the power source 400 to the drive motor 200. The motor driver circuit includes a plurality of sensors configured to measure an operational state of the drive motor 200 and the power source 400. The sensors may include voltage sensors, current sensors, temperature sensors, telemetry sensors, optical sensors, or combinations thereof. The sensors may measure voltage, current, and/or other electrical properties of the electrical energy supplied by the power source 400. The sensors may also measure rotational speed as revolutions per minute (RPM), torque, temperature, current draw, and/or other properties of the drive motor 200. The sensors can be indicative of load conditions on the end effector 160 and/or the instrument 10. In particular, the sensors can be correlated with the force required to fire or drive the staples 66 through tissue. RPM may be determined by measuring the rotation of the drive motor 200. Position of various drive shafts may be determined by using various linear sensors disposed in or in proximity to the shafts or extrapolated from the RPM measurements. In embodiments, torque may be calculated based on the regulated current draw of the drive motor 200 at a constant RPM.

Measuring the distance between the jaw members 162 and 164 can also be indicative of load conditions on the end effector 160 and/or the instrument 10. When large amounts of force are imparted on the jaw members 162 and 164, the jaw members are deflected outwards. The jaw members 162 and 164 are parallel to each other during normal operation, however, during deformation, the jaw members are at an angle relative to each other. Thus, measuring the angle between the jaw members 162 and 164 allows for a determination of the deformation of the jaw members due to the load being exerted thereon. The jaw members may include strain gauges 187 and 189 as shown in FIG. 17 to directly measure the load being exerted thereon. Alternatively, one or more proximity sensors 191 and 193 can be disposed at the distal tips of the jaw members 162 and 164 to measure the angle therebetween. These measurements are then transmitted to the microcontroller 500 which analyzes the angle and/or strain measurements and alerts the user of the stress on the end effector 160.

In another embodiment, the firing rod 220 or other load-bearing components include one or more strain gauges and/or load sensors disposed thereon. Under high strain conditions, the pressure exerted on the instrument 10 and/or the end effector 160 is translated to the firing rod 220 causing the firing rod 220 to deflect, leading to increased strain thereon. The strain gauges then report the stress measurements to the microcontroller 500. In another embodiment, a position, strain or force sensor may be disposed on the clutch plate 302.

During the approximation process, as the end effector 160 is clamped about tissue, the sensors disposed in the instrument 10 and/or the end effector 160 indicate to the microprocessor 500 that the end effector 160 is deployed about abnormal tissue (e.g., low or high load conditions). Low load conditions are indicative of a small amount of tissue being grasped by the end effector 160. High load conditions denote that too much tissue and/or a foreign object (e.g., tube, staple line, clips, etc.) is being grasped. In addition, a high load condition may denote that abnormal tissue (e.g., bowel) for cutting is being grasped. The microprocessor 500 thereafter indicates to the user via the user interface 120 that a more appropriate loading unit 169 and/or instrument 10 should be chosen. In addition, the microprocessor 500 may indicate to the user via the user interface 120 that abnormal tissue is being grasped by the end effector 160.

During the firing process, the sensors can alert the user of a variety of errors. Sensors may communicate to the microcontroller 500 that a staple cartridge or a portion of the instrument 10 is faulty. In addition, the sensors can detect sudden spikes in the force exerted on the knife, which is indicative of encountering a foreign body. Monitoring of force spikes could also be used to detect the end of the firing stroke, such as when the firing rod 220 encounters the end of the stapling cartridge and runs into a hard stop. This hard stop creates a force spike which is relatively larger than those observed during normal operation of the instrument 10 and could be used to indicate to the microcontroller that the firing rod 220 has reached the end of loading unit 169. Measuring of the force spikes can be combined with positional feedback measurements (e.g., from an encoder, linear variable displacement transducer, linear potentiometer, etc.) as discussed with respect to position and speed calculators 416 and 422. This allows for use of various types of staple cartridges (e.g., multiple lengths) with the instrument 10 without modifying the end effector 160.

When force spikes are encountered, the instrument 10 notifies the user of the condition and takes preventative measures by entering a so-called "pulse" or an electronic clutching mode, which is discussed in more detail below. During this mode the drive motor 200 is controlled to run only in short bursts to allow for the pressure between the grasped tissue and the end effector 160 to equalize. The electronic clutching limits the torque exerted by the drive motor 200 and prevents situations where high amounts of current are drawn from the power source 400. This, in turn, prevents damage to electronic and mechanical components due to overheating which accompanies overloading and high current draw situations.

The microcontroller 500 controls the drive motor 200 through a motor driver via a pulse width modulated control signal. The motor driver is configured to adjust the speed of the drive motor 200 either in clockwise or counter-clockwise direction. The motor driver is also configured to switch between a plurality of operational modes which include an electronic motor braking mode, a constant speed mode, an electronic clutching mode, and/or a controlled current activation mode. In electronic braking mode, two terminals of the drive motor 200 are shorted and the generated back EMF counteracts the rotation of the drive motor 200 allowing for faster stopping and greater positional precision in adjusting the linear position of the firing rod 220.

In the constant speed mode, the speed calculator 422 in conjunction with the microcontroller 500 and/or the motor driver adjust the rotational speed of the drive motor 200 to ensure constant linear speed of the firing rod 220. The electronic clutching mode involves repeat engagement and/or disengagement of the clutch 300 from the drive motor 200 in response to sensed feedback signals from the position and speed calculators 416 and 422. In controlled current activation mode, the current is either ramped up or down to prevent damaging current and torque spiked when transitioning between static to dynamic mode to provide for so-called "soft start" and "soft stop."

The data storage module 502 records the data from the sensors coupled to the microcontroller 500. In addition, the data storage module 502 records the identifying code of the loading unit 169, the status of the end effector 100, number of stapling cycles during the procedure, etc. The data storage module 502 is also configured to connect to an external device such as a personal computer, a PDA, a smartphone, a storage device (e.g., Secure Digital® card, Compact Flash® card, MemoryStick®, etc.) through a wireless or wired data port 503. This allows the data storage module 502 to transmit performance data to the external device for subsequent analysis and/or storage. The data port 503 also allows for so-called "in the field" upgrades of firmware of the microcontroller 500.

Figure 21:
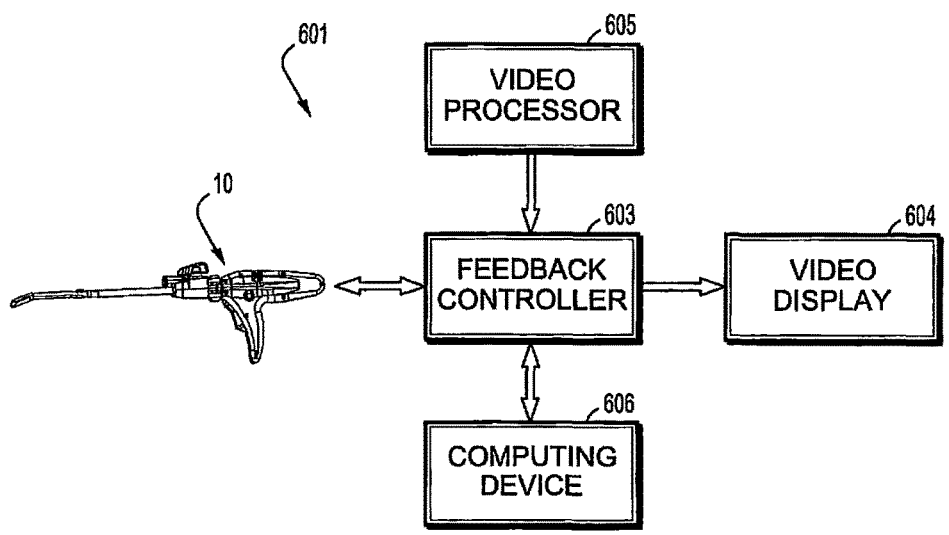
FIG. 21 is a schematic diagram of a feedback control system according to the present disclosure.
Figure 22A:
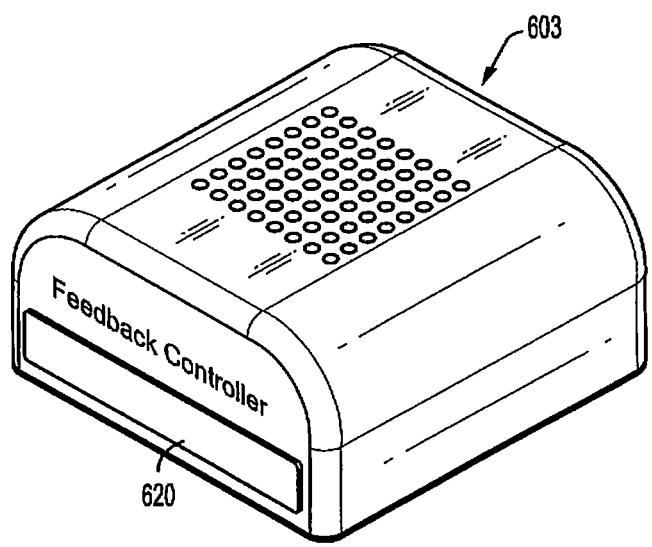
FIGS. 22A-B are perspective front and rear views of a feedback controller of the feedback control system according to the embodiment of the present disclosure.
Figure 22B:
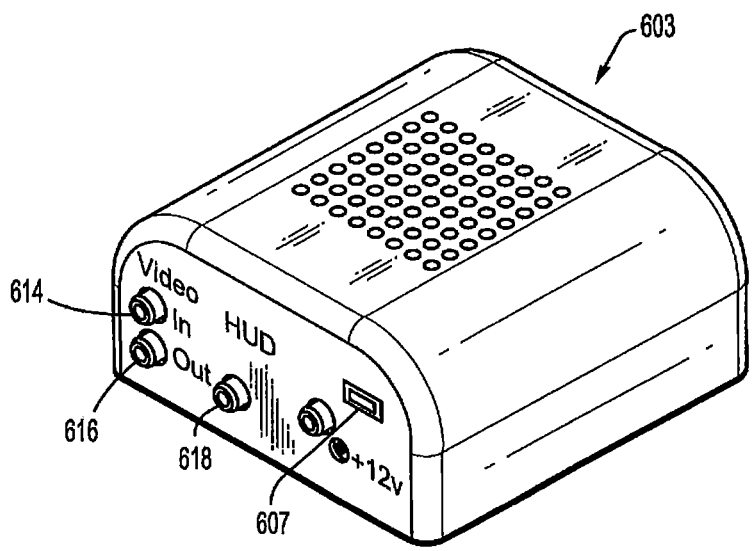

A feedback control system 601 is shown in FIGS. 21-22. The system includes a feedback controller 603 which is shown in FIGS. 22A-B. The instrument 10 is connected to the feedback controller 603 via the data port 502 which may be either wired (e.g., Firewire®, USB®, Serial RS232®, Serial RS485®, USART®, Ethernet®, etc.) or wireless (e.g., Bluetooth®, ANT3®, KNX®, ZWave®, X10® Wireless USB®, IrDA®, Nanonet®, Tiny OS®, ZigBee®, 802.11 IEEE, and other radio, infrared, UHF, VHF communications and the like).

With reference to FIG. 21, the feedback controller 603 is configured to store the data transmitted thereto by the instrument 10 as well as process and analyze the data. The feedback controller 603 is also connected to other devices, such as a video display 604, a video processor 605 and a computing device 606 (e.g., a personal computer, a PDA, a smartphone, a storage device, etc.). The video processor 605 is used for processing output data generated by the feedback controller 603 for output on the video display 604. The computing device 606 is used for additional processing of the feedback data. In one embodiment, the results of the sensor feedback analysis performed by the microcontroller 600 may be stored internally for later retrieval by the computing device 606.

The feedback controller 603 includes a data port 607 (FIG. 22B) coupled to the microcontroller 600 which allows the feedback controller 603 to be connected to the computing device 606. The data port 607 may provide for wired and/or wireless communication with the computing device 606 providing for an interface between the computing device 606 and the feedback controller 603 for retrieval of stored feedback data, configuration of operating parameters of the feedback controller 603 and upgrade of firmware and/or other software of the feedback controller 603.

The feedback controller 603 is further illustrated in FIGS. 22A-B. The feedback controller 603 includes a housing 610 and a plurality of input and output ports, such as a video input 614, a video output 616, and a heads-up ("HUD") display output 618. The feedback controller 603 also includes a screen 620 for displaying status information concerning the feedback controller 603.

Figure 23:
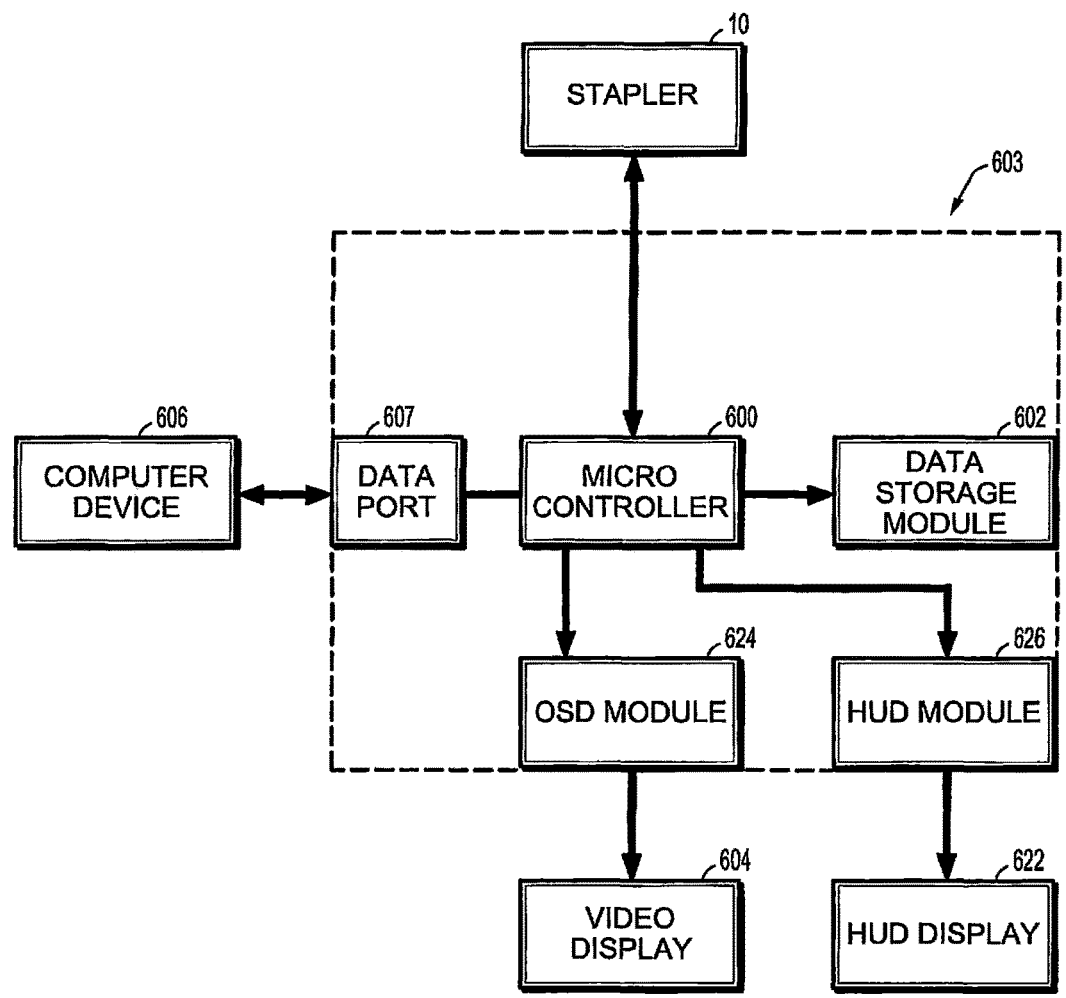
FIG. 23 is a schematic diagram of the feedback controller according to the embodiment of the present disclosure.

Components of the feedback controller 603 are shown in FIG. 23. The feedback controller 603 includes a microcontroller 600 and a data storage module 602. The microcontroller 600 and the data storage module 602 provide a similar functionality as the microcontroller 500 and the data storage module 502 of the instrument 10. Providing these components in a stand-alone module, in the form of the feedback controller 603, alleviates the need to have these components within the instrument 10.

The data storage module 602 may include one or more internal and/or external storage devices, such as magnetic hard drives, flash memory (e.g., Secure Digital® card, Compact Flash® card, MemoryStick®, etc.). The data storage module 602 is used by the feedback controller 603 to store feedback data from the instrument 10 for later analysis of the data by the computing device 606. The feedback data includes information supplied by the sensors disposed within the instrument 10 and the like.

The microcontroller 600 is configured to supplant and/or supplement the control circuitry, if present, of the instrument 10. The microcontroller 600 includes internal memory which stores one or more software application (e.g., firmware) for controlling the operation and functionality of the instrument 10. The microcontroller 600 processes input data from the user interface 120 and adjusts the operation of the instrument 10 in response to the inputs. The microcontroller 600 is coupled to the user interface 120 via a user feedback module 504 which is configured to inform the user of operational parameters of the instrument 10. More specifically, the instrument 10 is configured to connect to the feedback controller 603 wirelessly or through a wired connection via a data port 407 (FIG. 6).

In a disclosed embodiment, the microcontroller 600 is connected to the drive motor 200 and is configured and arranged to monitor the battery impedance, voltage, temperature and/or current draw and to control the operation of the instrument 10. The load or loads on battery 400, transmission, drive motor 200 and drive components of the instrument 10 are determined to control a motor speed if the load or loads indicate a damaging limitation is reached or approached. For example, the energy remaining in battery 400, the number of firings remaining, whether battery 400 must be replaced or charged, and/or approaching the potential loading limits of the instrument 10 may be determined. The microcontroller 600 may also be connected to one or more of the sensors of the instrument 10 discussed above.

The microcontroller 600 is also configured to control the operation of drive motor 200 in response to the monitored information. Pulse modulation control schemes, which may include an electronic clutch, may be used in controlling the instrument 10. For example, the microcontroller 600 can regulate the voltage supply of the drive motor 200 or supply a pulse modulated signal thereto to adjust the power and/or torque output to prevent system damage or optimize energy usage.

In one embodiment, an electric braking circuit may be used for controlling drive motor 200, which uses the existing back electromotive force of rotating drive motor 200 to counteract and substantially reduce the momentum of drive tube 210. The electric braking circuit may improve the control of drive motor 200 and/or drive tube 210 for stopping accuracy and/or shift location of powered surgical instrument 10. Sensors for monitoring components of powered surgical instrument 10 and to help prevent overloading of powered surgical instrument 10 may include thermal-type sensors, such as thermal sensors, thermistors, thermopiles, thermocouples and/or thermal infrared imaging and provide feedback to the microcontroller 600. The microcontroller 600 may control the components of powered surgical instrument 10 in the event that limits are reached or approached and such control can include cutting off the power from the power source 400, temporarily interrupting the power or going into a pause mode and/or pulse modulation to limit the energy used. The microcontroller 600 can also monitor the temperature of components to determine when operation can be resumed. The above uses of the microcontroller 600 may be used independently of or factored with current, voltage, temperature and/or impedance measurements.

The result of the analysis and processing of the data by the microcontroller 600 is output on video display 604 and/or the HUD display 622. The video display 604 may be any type of display such as an LCD screen, a plasma screen, electroluminescent screen and the like. In one embodiment, the video display 604 may include a touch screen and may incorporate resistive, surface wave, capacitive, infrared, strain gauge, optical, dispersive signal or acoustic pulse recognition touch screen technologies. The touch screen may be used to allow the user to provide input while viewing operational feedback. The HUD display 622 may be projected onto any surface visible to the user during surgical procedures, such as lenses of a pair of glasses and/or goggles, a face shield, and the like. This allows the user to visualize vital feedback information from the feedback controller 603 without losing focus on the procedure.

The feedback controller 603 includes an on-screen display module 624 and a HUD module 626. The modules 626 process the output of the microcontroller 600 for display on the respective displays 604 and 622. More specifically, the OSD module 624 overlays text and/or graphical information from the feedback controller 603 over other video images received from the surgical site via cameras disposed therein. The modified video signal having overlaid text is transmitted to the video display 604 allowing the user to visualize useful feedback information from the instrument 10 and/or feedback controller 603 while still observing the surgical site.

Figure 24:
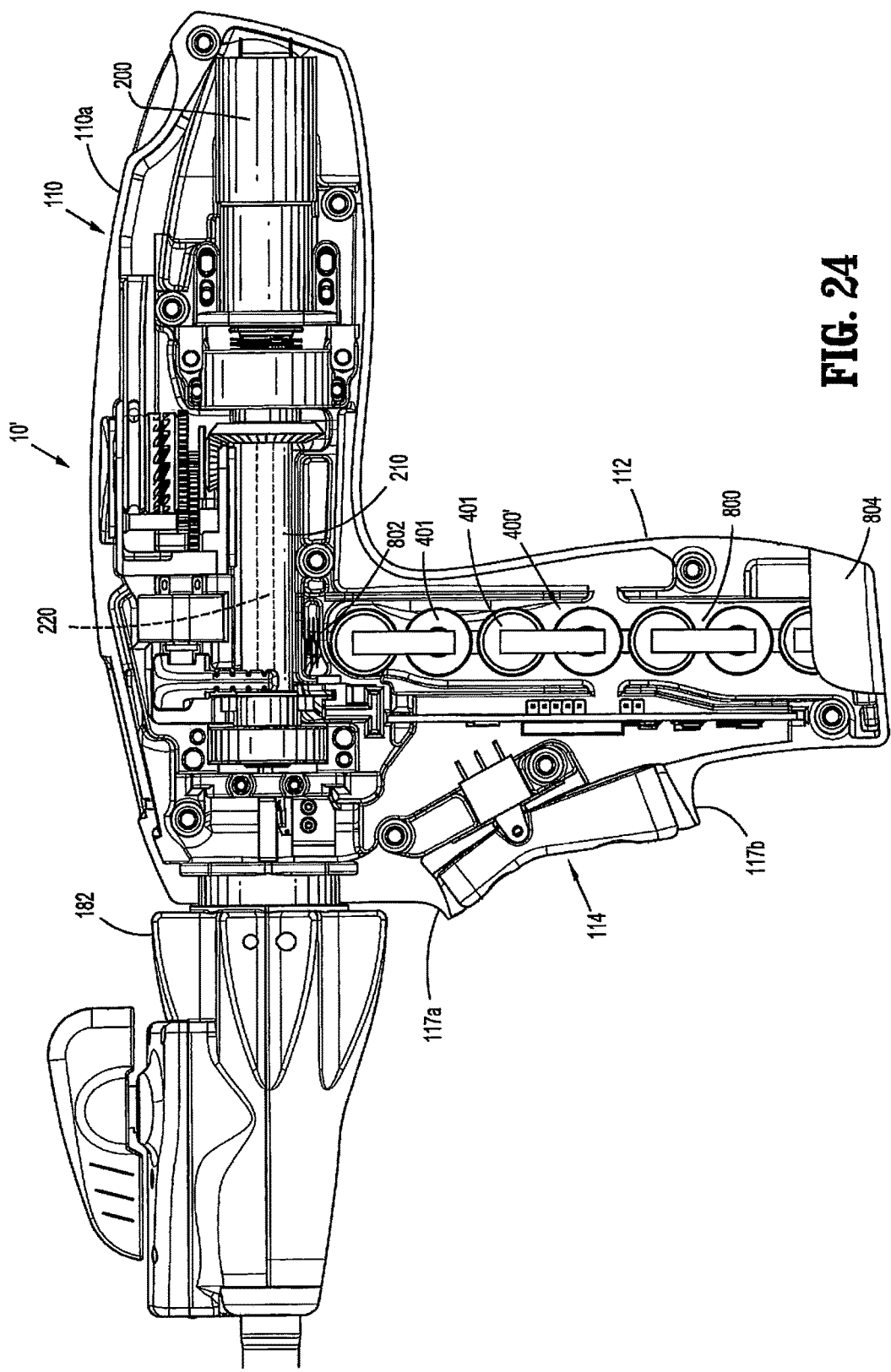
FIG. 24 is a partial sectional view of internal components of a powered surgical instrument in accordance with an embodiment of the present disclosure.
Figure 25:
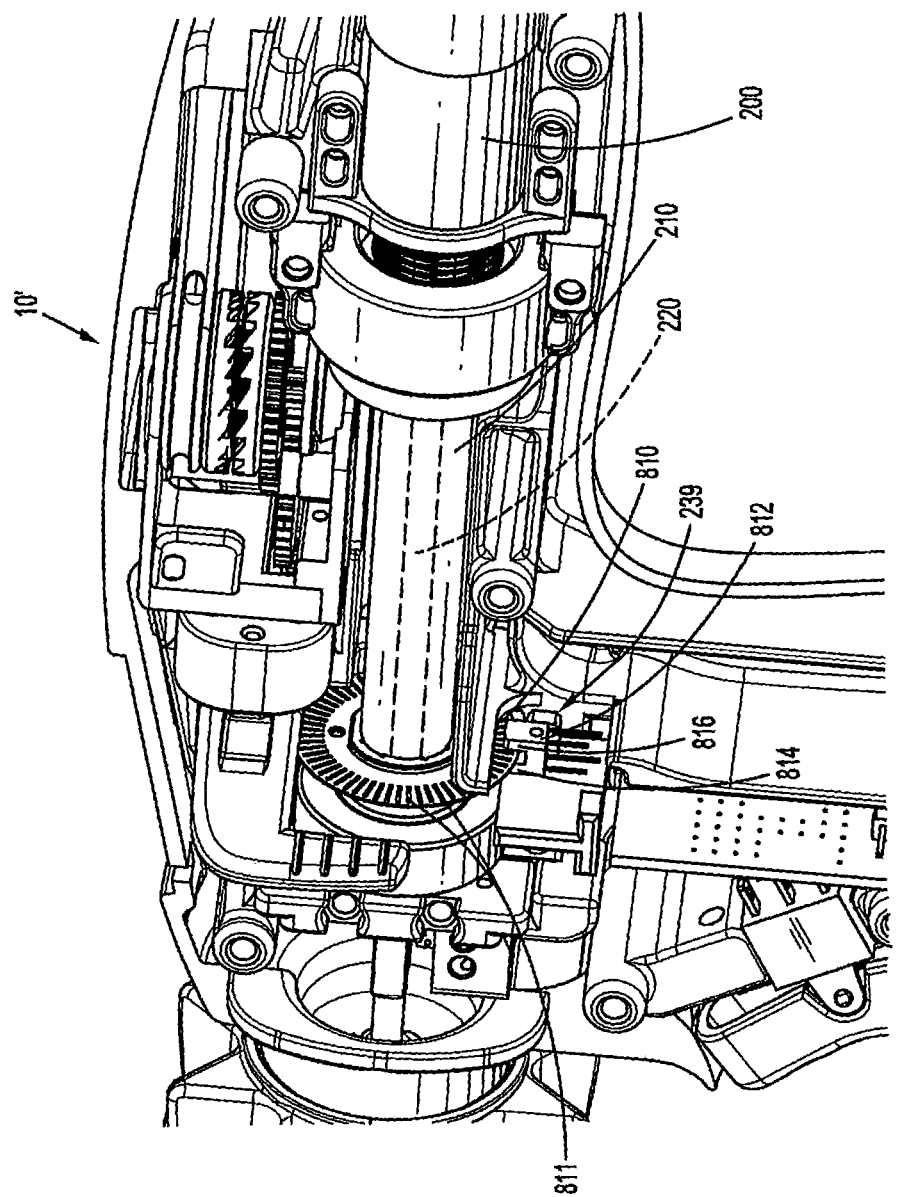
FIG. 25 is a partial perspective sectional view of internal components of the powered surgical instrument in accordance with an embodiment of the present disclosure.

FIGS. 24-25 illustrate another embodiment of the instrument 10'. The instrument 10' includes a power source 400' having a plurality of cells 401 arranged in a straight configuration. The power source 400' is inserted vertically into a vertical battery chamber 800 within the handle portion 112. The battery chamber 800 includes a spring 802 within the top portion thereof to push downward the power source 400'. In one embodiment, the spring 802 may include contacts to electrically couple with the power source 400'. The power source 400' is held within the battery chamber 800 via a battery cap 804 which is configured to slide in a distal direction to lock in place. The cap 804 and the handle 112 may include tongue and groove couplings to keep the cap 804 from sliding out. The power source 400' is biased against the cap 804 due to the downward force of the spring 802. As the cap 804 is slid in a proximal direction, the power source 400' is ejected from the battery chamber 800 by the spring 802.

FIG. 25 shows another embodiment of the rotational sensor 239 which detects the rotation of the drive tube 210, thus, measuring the rate of rotation of the drive tube 210 which allows for determination of the linear velocity of the firing rod 220. The rotational sensor 239 includes an encoder wheel 810 mounted to drive tube 210 and an optical reader 812 (e.g., photo interrupter). The optical reader 812 is configured to determine the number of interruptions in a light beam which is continuously provided between two opposing edges 814 and 816 thereof. The wheel 810 rotates with the drive tube 210 and includes a plurality of slits 811 therethrough.

The outer edge of the wheel 810 is disposed between the opposing edges of the optical reader 812 such that the light being transmitted between the edges 814 and 816 shine through the slits 811. In other words, the light beam between the edges 814 and 816 is interrupted by the wheel 810 as the drive tube 210 is rotated. The optical reader 812 measures the number of interruptions in the light beam and rate of occurrences thereof and transmits these measurements to the speed calculator 422 which then determines the speed of the drive rod 220 as discussed above.

FIGS. 27-32 show the instrument 10' having a retraction assembly 820 for retracting the firing rod 220 from its fired position. The retraction assembly 820 provides for a manually driven mechanical interface with the drive tube 210 allowing for manual retraction of the firing rod 210 via ratcheting action of the retraction assembly 820 in emergency situations (e.g., electrical malfunction, stuck end effector 160, etc.). The retraction assembly 820 may be configured as a modular assembly which can be inserted into the instrument 10'.

Figure 30:
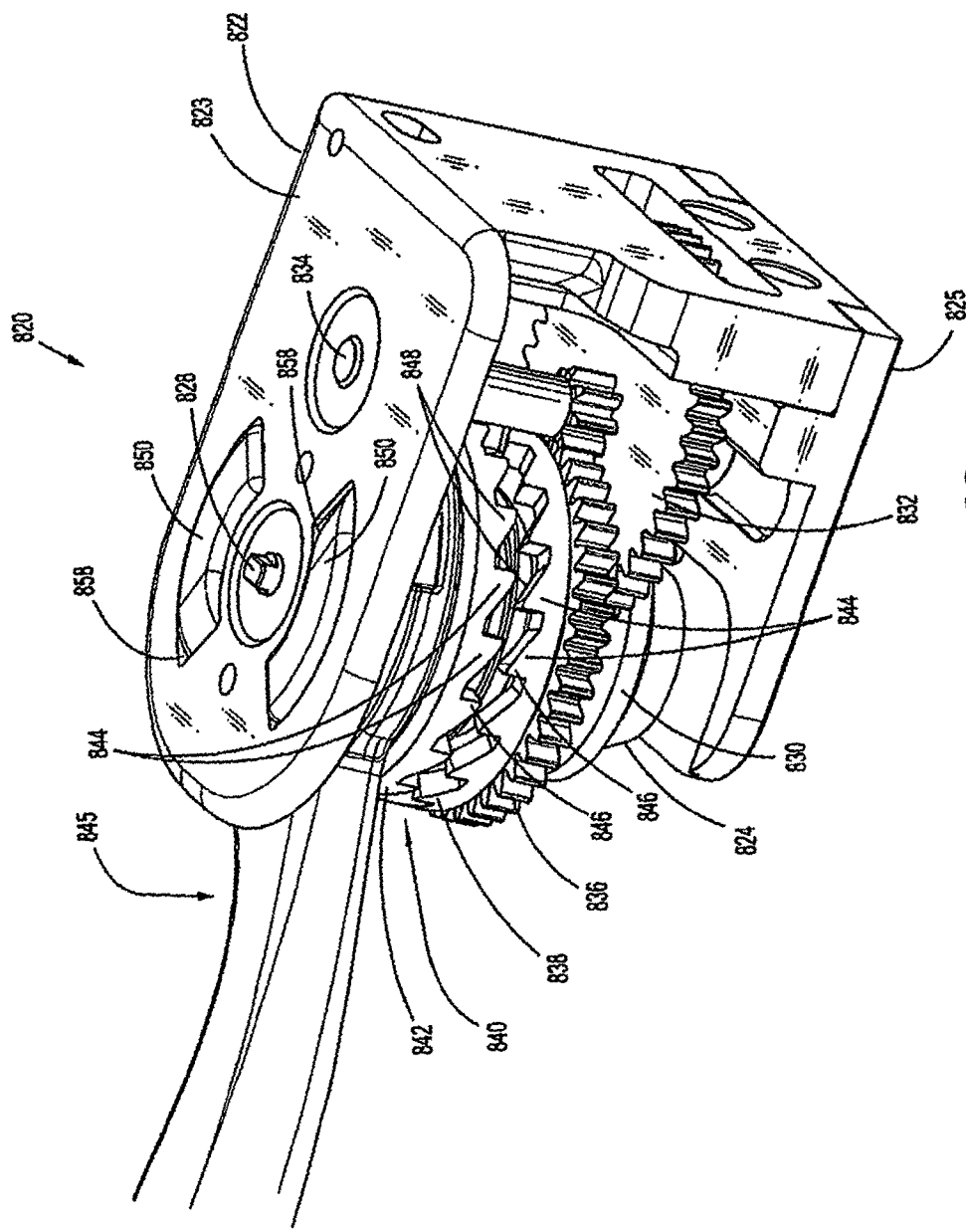
FIG. 30 is a perspective view of a modular retraction assembly of the powered surgical instrument in accordance with an embodiment of the present disclosure.

With reference to FIG. 30, the retraction assembly 820 includes a retraction chassis 822 having top portion 823 and a bottom portion 825. The retraction assembly 820 interfaces mechanically with the drive tube 210 via a drive gear 826 and a retraction gear 824. The drive gear 826 is attached to the drive tube 210 and is translated in response to the rotation of the drive tube 210. Conversely, rotation of the drive gear 826 imparts rotation on the drive tube 210. The drive gear 826 and the retraction gear 824 may be bevel gears allowing the gears 824 and 826 to interface in a perpendicular manner.

The retraction gear 824 is coupled to a first spindle 828 which is disposed in a substantially perpendicular manner between the top and bottom portions 823 and 825 of the retraction chassis 822 and is rotatable around a longitudinal axis defined thereby. The first spindle 828 further includes a first spur gear 830 attached thereto and to the retraction gear 824. The first spur gear 830 interfaces with a second spur gear 832 disposed on a second spindle 834 which is also is disposed in a substantially perpendicular manner between the top and bottom portions 823 and 825 of the retraction chassis 822 and is rotatable around a longitudinal axis defined thereby.

Figure 31:
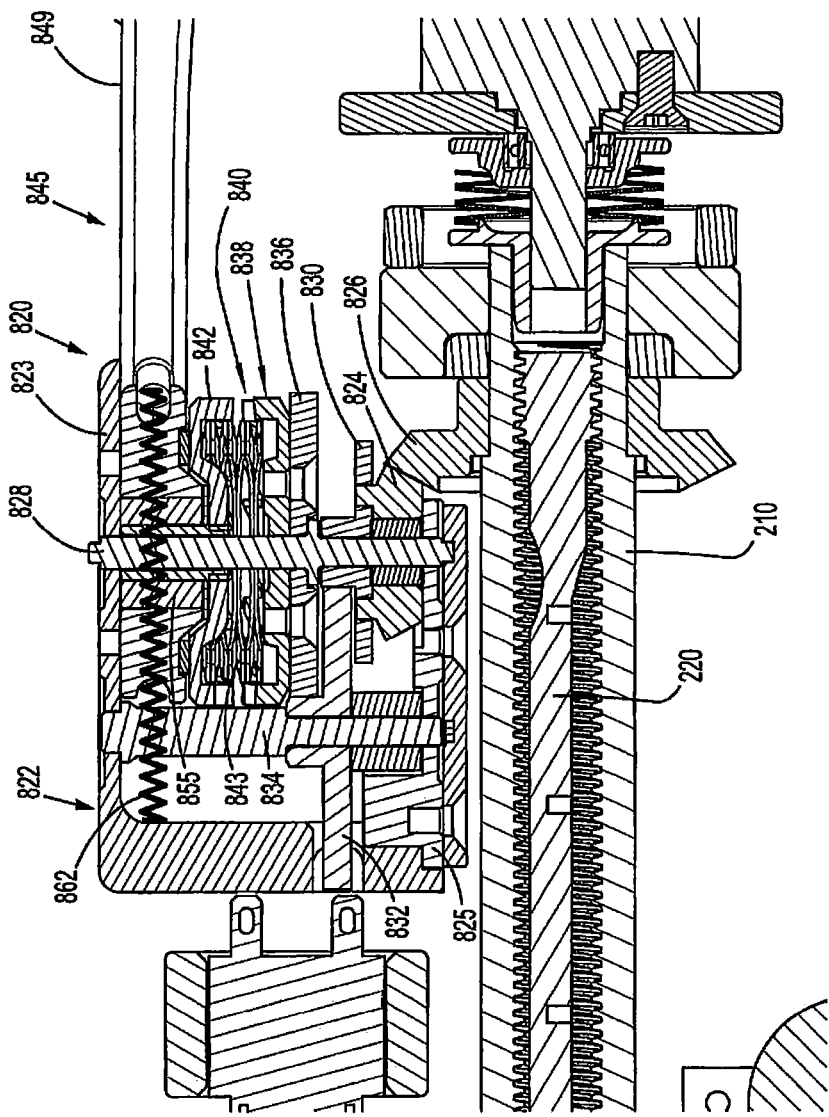
FIG. 31 is an enlarged partial sectional view of internal components of a powered surgical instrument in accordance with an embodiment of the present disclosure.

The second spur gear 832 interfaces mechanically with a third spur gear 836 which is disposed on the first spindle 828. The third spur gear 836 is attached to a first clutch portion 838 of a unidirectional clutch assembly 840. The clutch assembly 840 further includes a second clutch portion 840 rotatably disposed on the first spindle 828 above the first clutch portion 838 with a spring 843 disposed between the first and second clutch portions 838 and 840 thereby keeping the first and second clutch portions 838 and 840 in a raised non-interlocking configuration (e.g., first configuration) as shown in FIG. 31.

Rotation of the drive tube 210 and/or the drive gear 826 imparts rotation on the retraction gear 824 and the first, second and third spur gears 830, 832 and 836 along with the first portion 838 and the respective spindles 828 and 834. Since, the second clutch portion 842 can rotate about the spindle 828 and is separated from the first clutch portion 838 by the spring 843, the rotation of the first portion 838 is not translated thereto.

Figure 32:
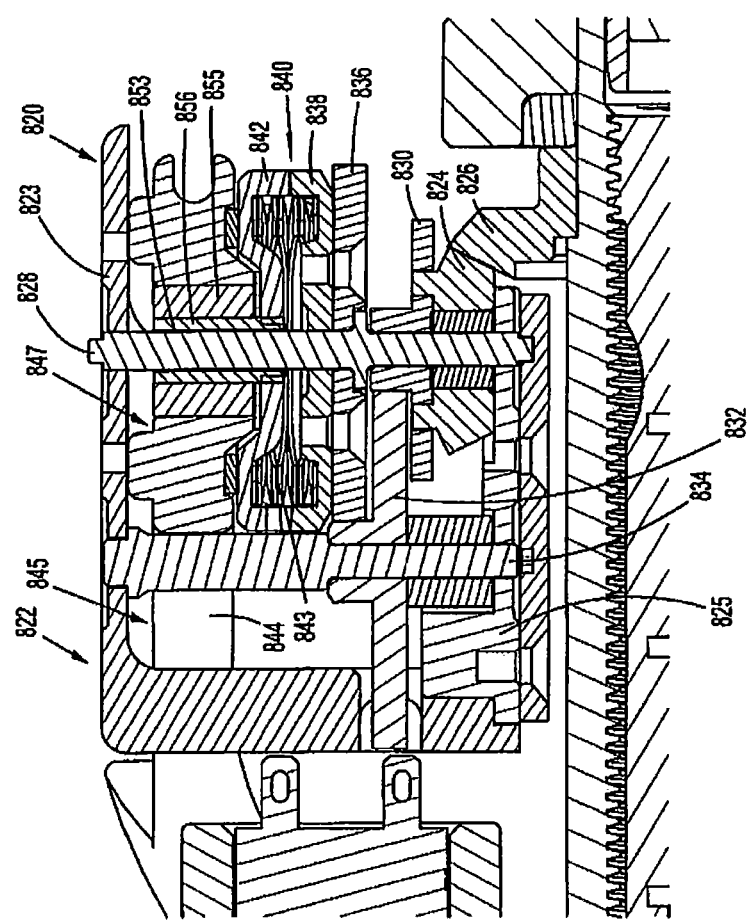
FIG. 32 is an enlarged partial sectional view of internal components of a powered surgical instrument in accordance with an embodiment of the present disclosure.

The first and second clutch portions 838 and 842 include a plurality of interlocking teeth 844 having a flat interlocking surface 846 and a sloping slip surface 848. In a second configuration as shown in FIG. 32, the second clutch portion 842 is pushed downwards by a retraction lever 845 thereby interfacing the teeth 844. The slip surfaces 848 allow for the interlocking surfaces 846 to come in contact with each other thereby allowing rotation of the second clutch portion 842 to rotate the first clutch portion 838 and all of the interfacing gears.

Figure 27:
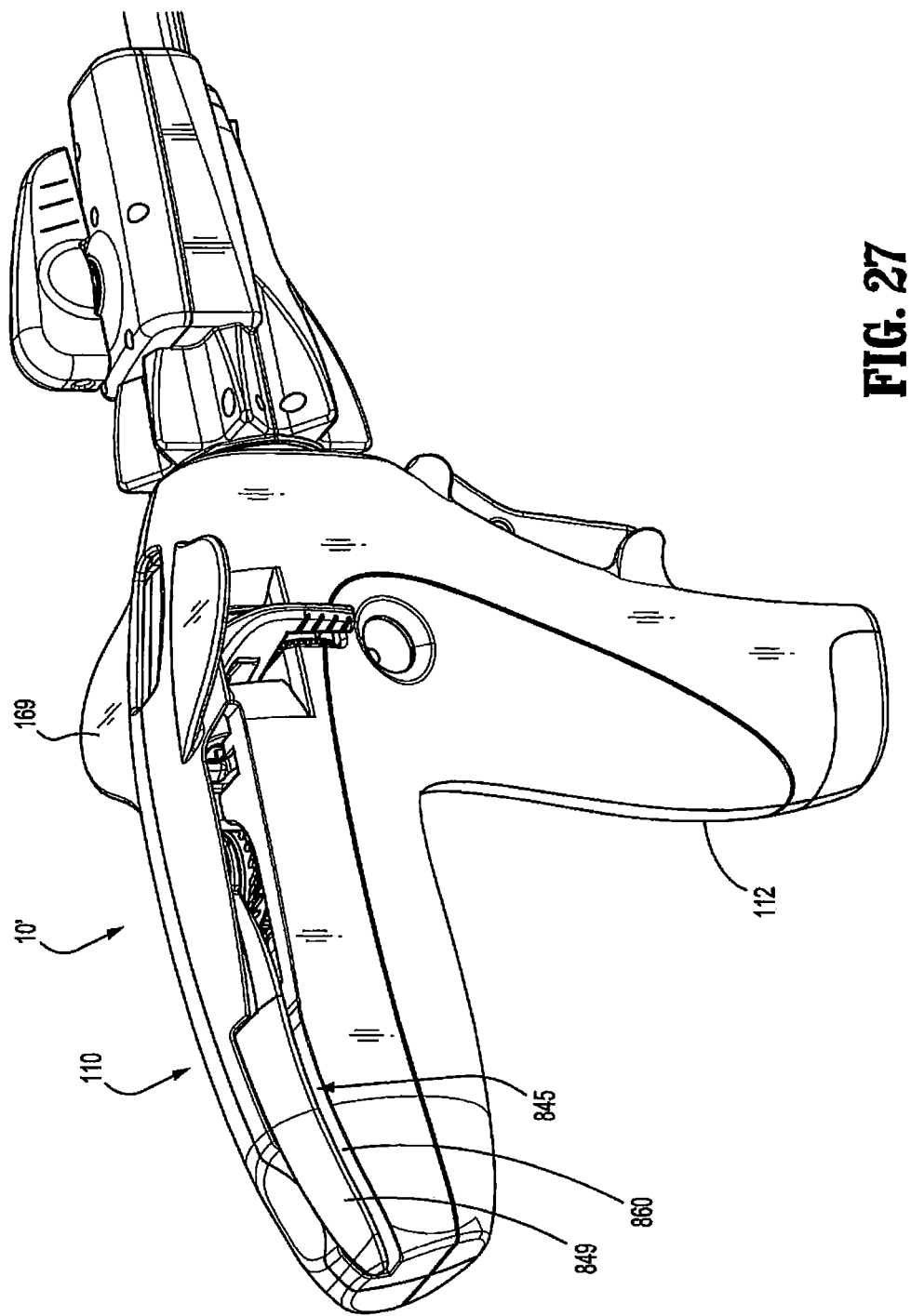
FIG. 27 is a partial perspective view of a retraction lever of the powered surgical instrument in accordance with an embodiment of the present disclosure.
Figure 29:
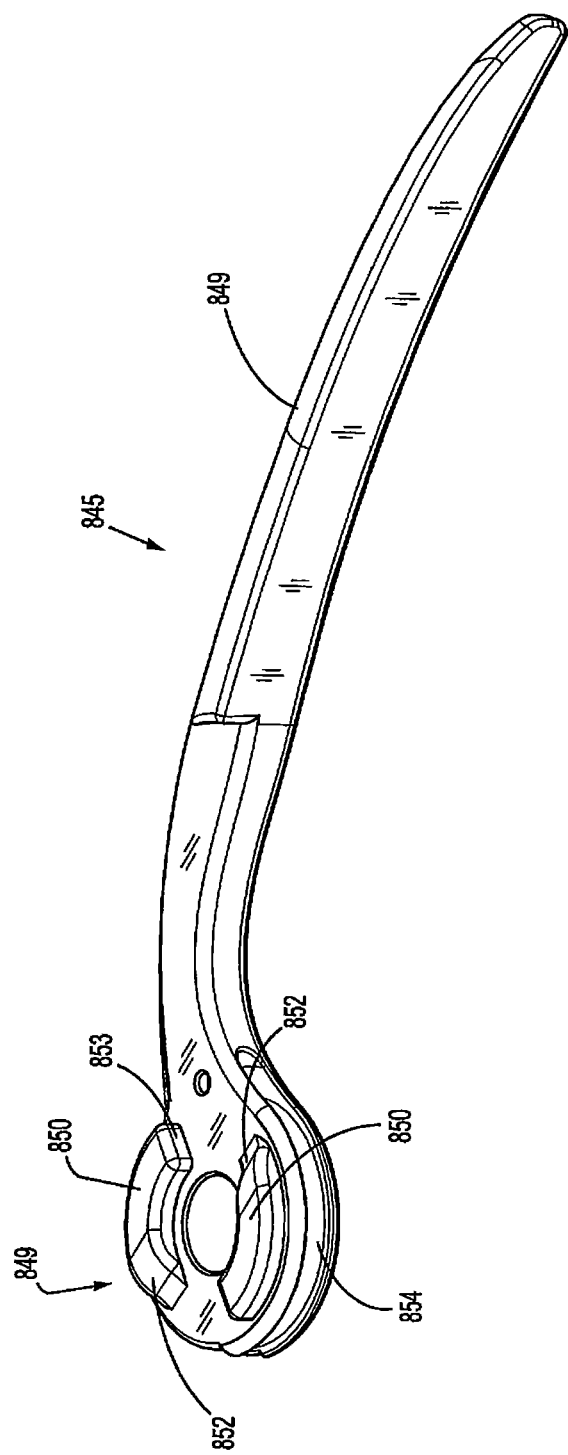
FIG. 29 is a perspective view of the powered surgical instrument in accordance with an embodiment of the present disclosure.

The retraction lever 845 includes a camming portion 847 and a handle 849 attached thereto. The camming portion 847 includes an opening 853 which houses a unidirectional needle clutch 855 which is mechanical cooperation with a fitting 856 attached to the first spindle 828 thereby allowing the retraction lever 845 to rotate about the first spindle 828. With reference to FIG. 29, the lever 845 includes a one or more camming members 850 having a camming surface 852. In the first configuration, the lever 845 is disposed along a lever pocket 860 of the housing 110 as shown in FIG. 27. The lever 845 is pushed up by the spring 843 against the top portion 823 and the camming members 850 are disposed within corresponding cam pockets 858. The lever 845 is maintained in the first configuration by a return extension spring 862 mounted between the top portion 823 and the camming portion 847. The camming members 850 and the lever pocket 860 prevent further rotation of the lever 845.

As the lever 845 is pulled out of the lever pocket 860, the camming members 850 interface with the corresponding cam pockets 823 and push the camming portion 847 of the lever 845 in a downward direction. The downward movement compresses the spring 843 and pushes the first and second clutch portions 838 and 842 together interlocking the teeth 844 thereby engaging the portions 838 and 842. Rotation of the camming portion 847 in a counterclockwise direction actuates the needle clutch 855 which interfaces with the fitting 856 and the first spindle 828. Continual rotation of the lever 845 rotates the clutch assembly 840 which in turn rotates the spur gears 836, 832 and 830 and the retraction and drive gears 824 and 826. This in turn rotates drive tube 210 and retracts the drive rod 220.

Figure 28:
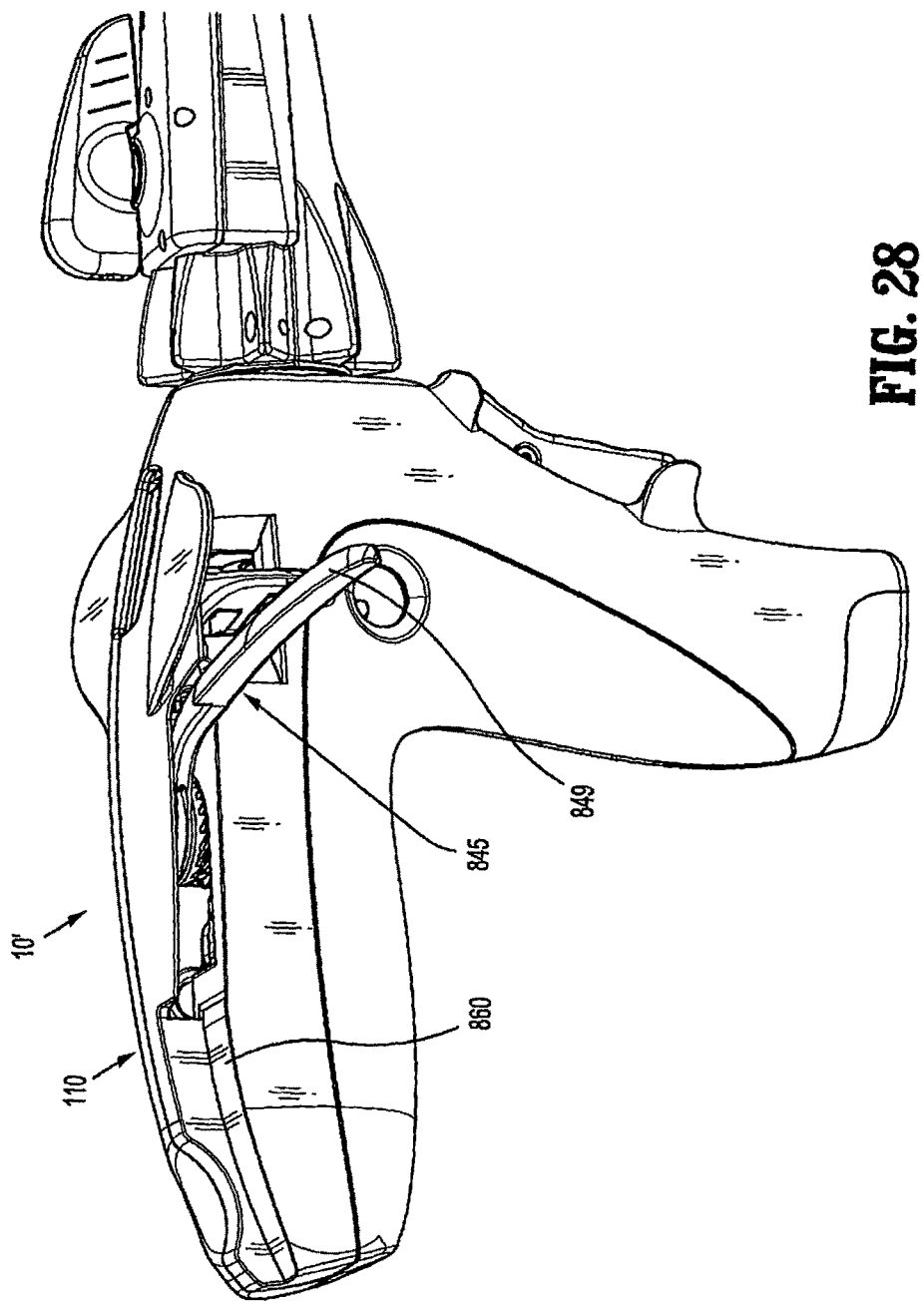
FIG. 28 is a partial perspective view of the powered surgical instrument in accordance with an embodiment of the present disclosure.

The lever 845 can be rotated for a predetermined amount until the handle 849 abuts the housing 110 as shown in FIG. 28. Thereafter, the lever 845 is brought back to its first configuration by the return extension spring 862. This raises the camming portion 847 allowing the second clutch portion 842 to also move upward and disengage the first clutch portion 838. The needle clutch 855 releases the fitting 856 allowing the lever 845 to return to the first configuration without affecting the movement of the drive tube 210. Once the lever 845 is returned to the first configuration, the lever 845 may be retracted once again to continue to ratchet the driving rod 220.

Figure 33:
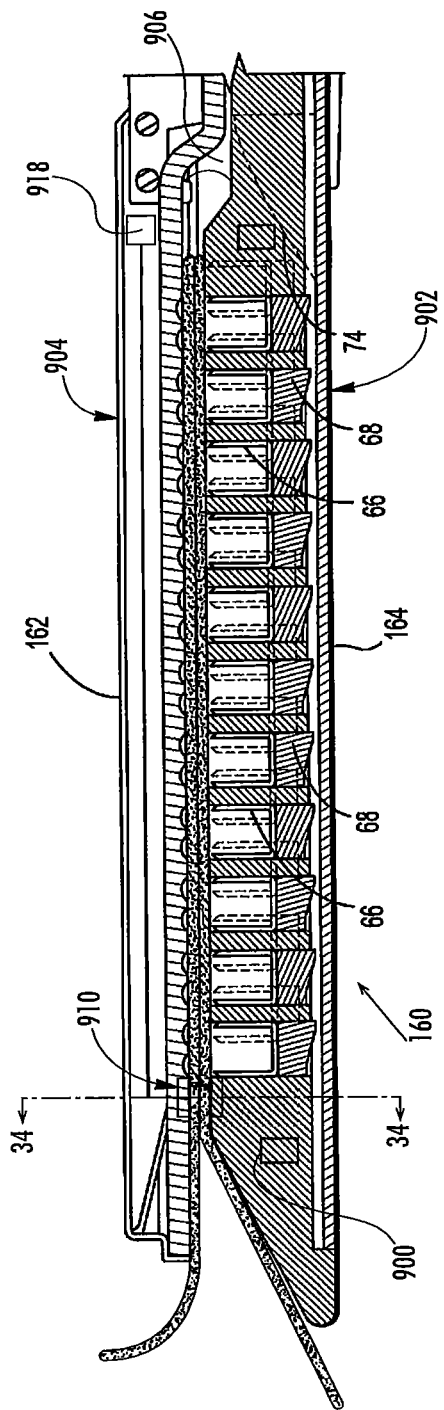
FIG. 33 is a side cross-sectional view of an embodiment of an end effector of the powered surgical instrument of FIG. 1 in accordance with the present disclosure.
Figure 34:
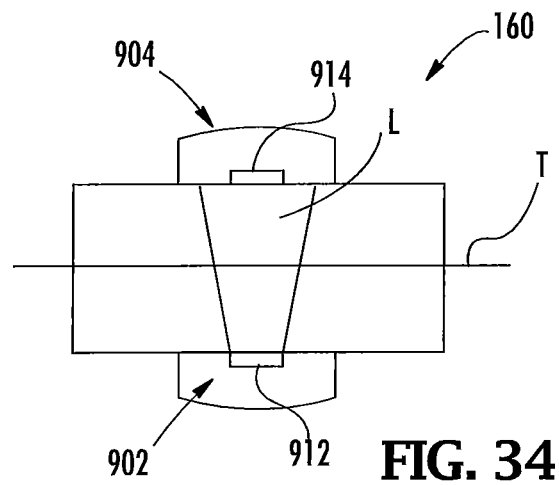
FIG. 34 is a rear cross-sectional view taken along the section line of FIG. 33.

Referring to FIGS. 33 and 34, the end effector 160 includes a first jaw member 902, a second jaw member 904, and a knife 906. The first and second jaw members 902, 904 are moveable relative to one another between an open position and a clamped position. In the clamped position, tissue may be grasped or clamped within the end effector 106 between the first and second jaw members 902, 904. The knife 906 is moveable through the first and second jaw member 902, 904 along a longitudinal axis of the end effector 160 to sever tissue clamped within the end effector 160.

The end effector 160 includes a detection assembly 910 provided in accordance with the present disclosure that detects or senses properties of tissue clamped within the end effector 160 before the knife 906 is actuated to sever tissue clamped within the end effector 160. The detection assembly 910 may prevent or lockout the knife 906 from actuating based on sensed tissue properties. The detection assembly 910 analyzes the clamped tissue to determine one or more attributes of the clamped tissue including, but not limited to, the thickness of clamped tissue, the type of clamped tissue, or the presence of vasculature within clamped tissue. As such, the detection assembly 910 may prevent the knife 906 from severing tissue if undesired tissue (e.g., bowels) is clamped within the end effector 160. The detection assembly 910 may detect the high vascularity of the undesired tissue as compared to the low vascularity of the desired tissue (e.g., adhesions).

With continued reference to FIGS. 33 and 34, the detection assembly 910 includes a light source 912, a light sensor 914, and a processor 918. The light source 912 is disposed within the first jaw member 902 and the light sensor 914 is disposed within the second jaw member 904 in opposition to the light source 912. As shown, the light source 912 and the light sensor 914 are each positioned adjacent a distal end of one of the first and second jaw members 902, 904; however, it is contemplated that the light source 912 and the light sensor 914 may be positioned in opposition to one another anywhere along tissue contacting surfaces of the first and second jaw members 902, 904. As detailed below, when tissue is clamped within the end effector 160, the light source 912 emits light through the clamped tissue towards the light sensor 914 that optically senses properties of light transmitted through the clamped tissue. It is contemplated that the light source 912 may emit light and the light sensor 914 may sense properties of light before, during, and/or after actuation of the knife 906.

The light source 912 may generate light by a variety of means including, but not limited to, electron-stimulation, incandescent lamps, electroluminescent, gas discharge, high-intensity discharge, lasers, chemoluminescence, fluorescence, and/or phosphorescence. The light source 912 may be a light emitting diode (LED). The light emitted from the light source 912 may be in the visual and/or infrared spectrum. The light source 912 may be activated as the switch 114 (FIG. 1) is depressed. The light may be transmitted by a fiber optic cable The light sensor 914 is configured to optically sense properties of light in contact therewith. The light sensor 914 may be configured to detect a specific chemical or agent injected into the blood stream of a patient including, but not limited to, chemicals or agents capable of bioluminescence, radioluminescence, chemoluminescence, fluorescence, and/or phosphorescence. Further, the light sensor 914 may sense properties of light indicating foreign bodies, diseased tissue, or non-tissue within clamped tissue.

The light sensor 914 converts the optically sensed properties of light to data signals that are transmitted to the processor 918. It is contemplated that the light sensor 914 may be wired directly to or wirelessly connected to the processor 918.

The wireless connection may be via radio frequency, optical, WIFI, Bluetooth® (an open wireless protocol for exchanging data over short distances (using short length radio waves) from fixed and mobile devices, creating personal area networks (PANs)), ZigBee® (a specification for a suite of high level communication protocols using small, low-power digital radios based on the IEEE 802.15.4-2003 standard for wireless personal area networks (WPANs)), etc.

The processor 918 analyzes the data signals received from the light sensor 914 to determine attributes of the tissue clamped within the end effector 160. The processor 918 may display the tissue attributes on the user interface 120 (FIG. 3) (e.g., screen 122).

The processor 918 compares the calculated tissue attributes to predetermined accepted values before and/or during actuation of the knife 906. The processor 918 may prevent or lockout the knife 906 from actuating if one or more of the calculated tissue attributes are not within a predetermined range of acceptable values. The processor 918 may also retract the knife if one or more of the calculated tissue attributes is not within a predetermined range of acceptable values. The processor 918 may also provide feedback to a user when a calculated tissue attribute is not within the predetermined range of acceptable values. The feedback may be audible, haptic, or visual indicia as detailed above.

The processor 918 may calculate the thickness of clamped tissue from the intensity of the light transmitted through the clamped tissue. The processor 918 may calculate the thickness of various known tissue types (i.e., lung, stomach, intestinal, muscular, etc.) from the intensity of the light transmitted through the clamped tissue. The light sensor 914 may sense multiple wavelengths of light and the processor 918 may determine the type of clamped tissue from the intensity or optical power of each wavelength sensed by the light sensor 914. In addition, the processor 918 may determine the vasculature of clamped tissue from the intensity of light, at specific wavelengths, absorbed by the clamped tissue.

The tissue thickness may be determined by the red blood cell density within the tissue. For example, if there is too much blood occlusion in the clamped tissue, the reduced density of red blood cells is indicative that the clamped tissue is too thick or includes too much vasculature for the knife 906 to safely sever.

The attributes of clamped tissue may also be detected by detecting abnormal blood flow. For example, abnormal blood flow may indicate that cancerous or tumorous tissue is clamped within the end effector 160. In such instances, the processor 918 may inform a clinician that a resection margin (i.e., the amount of tissue being removed containing cancerous or tumorous tissue) should be increased.

As shown, the processor 918 is disposed within the second jaw member 904; however, it is contemplated that the processor 918 may be disposed within the first jaw member 902 or anywhere within the surgical instrument 10 (FIG. 1) (e.g., within the body portion 168 or housing 110) or external to the surgical instrument 10. It is also contemplated that the processor 918 may be integrated into the microcontroller 500 (FIG. 6).

Additionally or alternatively, the processor 918 may allow or enable firing of the staple cartridge 164 if a calculated tissue attribute is within the predetermined range of values. The processor 918 may provide audible, haptic, or visual indicia to the clinician to alert the clinician that the calculated tissue attribute is within the predetermined range of values (e.g., a green light, a go ahead tone, a go icon, a go light pattern, an audible go pattern, etc.).

Figure 35:
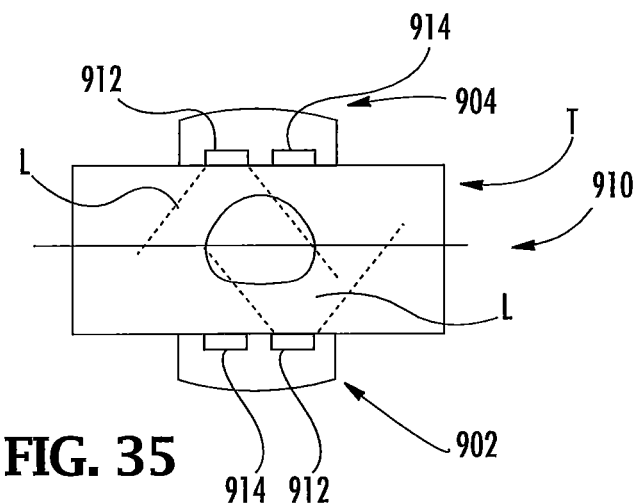
FIG. 35 is a rear cross-sectional view of another end effector in accordance with an embodiment of the present disclosure.

Referring to FIG. 35, another detection assembly 910 is provided in accordance with the present disclosure and includes a light source 912 and a light sensor 914 disposed adjacent one another in each of the first and second jaw member 902, 904 with the light source 912 of the first jaw member 902 opposing the light sensor 914 of the second jaw member 904 and the light source 912 of the second jaw member 904 opposing the light sensor 914 of the first jaw member 902. In such a configuration, the light sensors 914 may sense light reflected from the tissue clamped within the end effector 160 in addition to light transmitted through the clamped tissue. One of the light sources 912 may emit light having a first wavelength and the other of the light sources 912 may emit light having a second wavelength (e.g., the light source 912 of the first jaw member 902 may emit light in the visual spectrum and the light source 912 of the second jaw member 904 may emit light in the infrared spectrum) allowing the processor 918 to determine if the attributes of light sensed by each light sensor 914 is an attribute of transmitted or reflected light indicating absorption of known wavelengths within the tissue.

Figure 36:
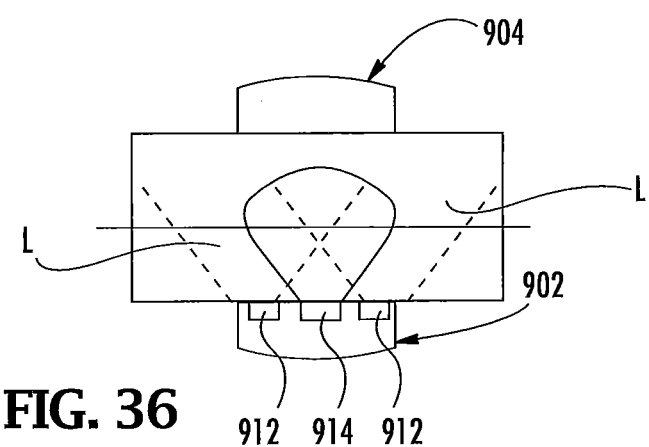
FIG. 36 a rear cross-sectional view of yet another embodiment of an end effector of the powered surgical instrument of FIG. 1 in accordance with the present disclosure.

Referring to FIG. 36, yet another the detection assembly 910 is provided in accordance with the present disclosure and includes two light sources 912 and a light sensor 914 disposed within the first jaw member 902 with the light sensor 914 disposed between the light sources 912. The light sensor 914 senses light attributes of light emitted from the light sources 912 and reflected off of tissue clamped within the end effector 160. Due to the relative proximity of light sources 912 it may be desirable to include a light blocking shade between the light sources to enhance the depth of light penetration within the tissue. As shown, the second jaw member 904 does not include a light source or a light sensor; however, it is contemplated that the second jaw member 904 may include a light source 912 opposing the light sensor 914 of the first jaw member 902 and two light sensors 914 with each opposing one of the light sources 912 of the first jaw member 902.

Figure 37:
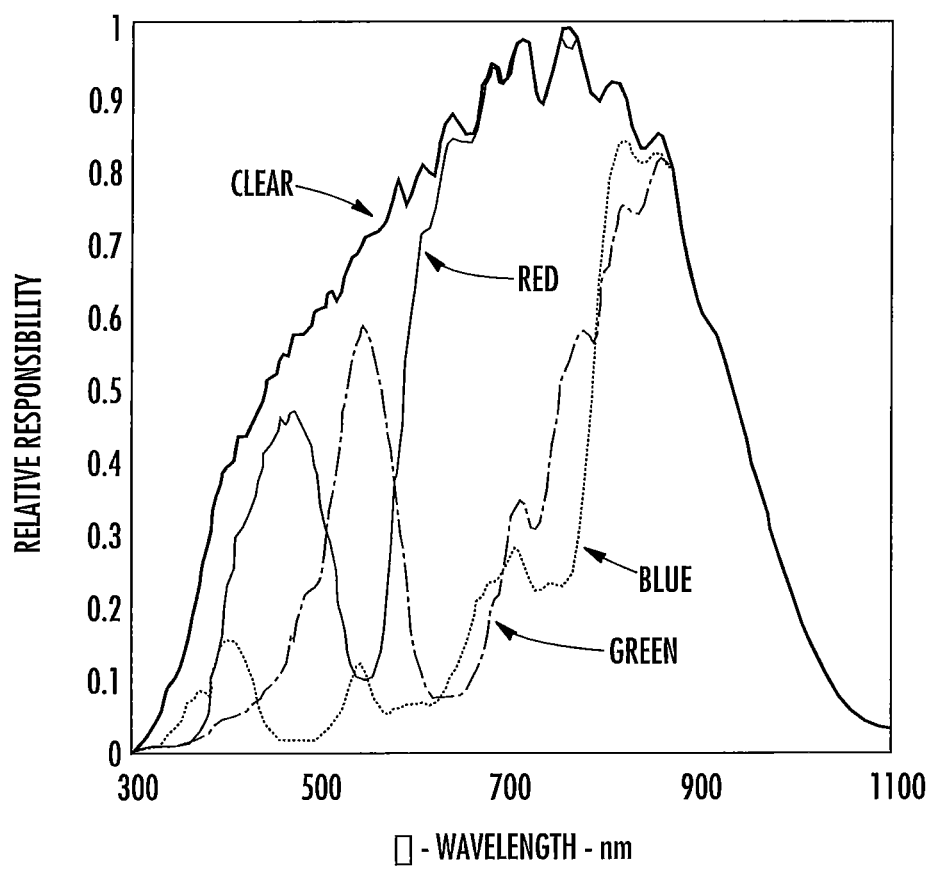
FIG. 37 is a chart showing the responsivity of the wavelengths of light.

With reference to FIG. 37, the responsivity of light transmitted through tissue as detected by light sensors (e.g., light sensors 914) sensitive to different wavelengths of light as indicated by the labels "CLEAR," "RED," "BLUE," and "GREEN." As shown, the intensity of the wavelength of light may be used to determine the color of the tissue clamped within the end effector 160. It will be appreciated that when the light is transmitted through tissue clamped within the end effector 160, the wavelength corresponding to the color of the tissue is not transmitted through the tissue such that the wavelengths of transmitted light may be analyzed to determine the color of the clamped tissue.

Figure 38:
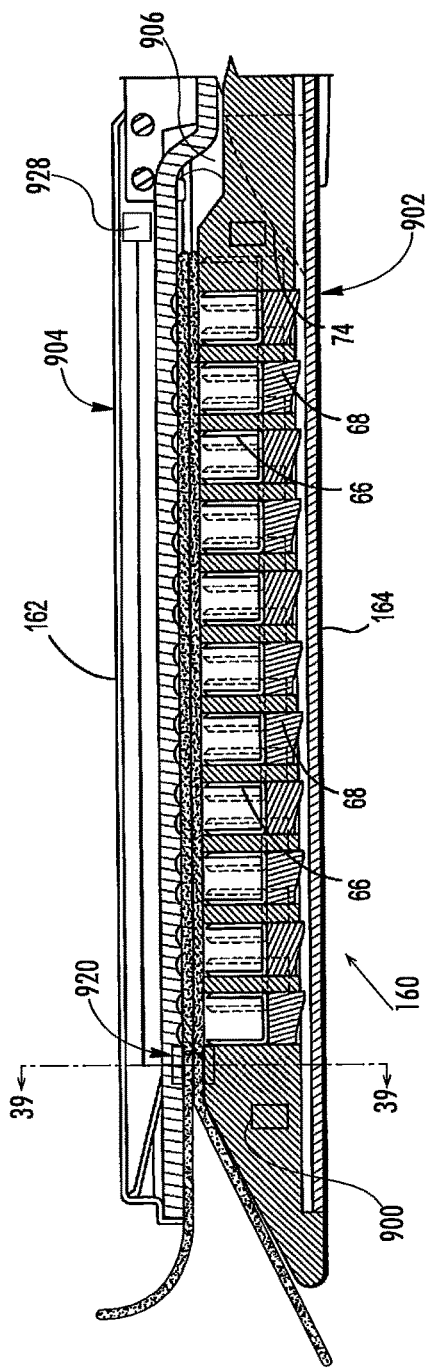
FIG. 38 is a side cross-sectional view of another end effector of the powered surgical instrument of FIG. 1 in accordance with an embodiment of the present disclosure.
Figure 39:
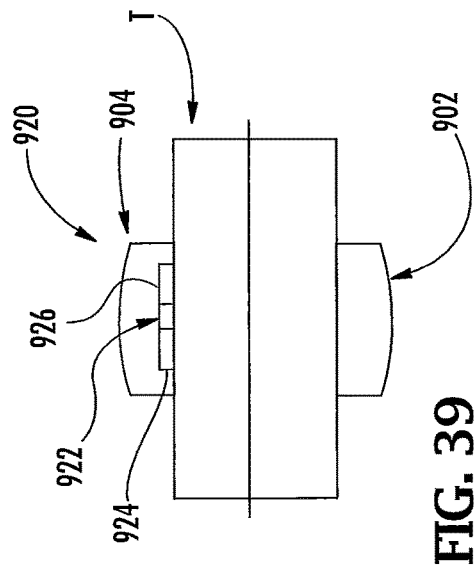
FIG. 39 is a cross-sectional view taken along the section line of FIG. 38.

Referring to FIGS. 38 and 39, another detection assembly 920 in accordance with the present disclosure includes an ultrasound probe 922 and a processor 928. The ultrasound probe 922 is disposed in one of the jaw members 902, 904 adjacent a distal end of the thereof. Similar to the detection assembly 910 detailed above, the detection assembly 920 detects or senses properties of tissue clamped within the end effector 160 before the knife 906 is actuated to sever tissue clamped within the end effector 160, as such only the differences will be detailed herein.

The ultrasound probe 922 includes an ultrasonic transducer 924 and an ultrasound sensor 926. The ultrasonic transducer 924 converts electrical energy to sound wave energy. The ultrasonic transducer 924 may convert electrical energy to sound wave energy with piezoelectric crystals. The sound wave energy is directed towards tissue adjacent the ultrasound probe 922 with some of the sound wave energy being reflected back towards the ultrasound probe 922. The ultrasound sensor 926 senses the sound wave energy reflected back towards the ultrasound probe 922 to develop a sonogram of the tissue adjacent the ultrasound probe 922.

The ultrasound sensor 926 converts the sensed sound wave energy to data signals that are sent to the processor 928. Similar to the processor 918 of the detection assembly 910, the processor 928 may be disposed within the end effector 160, within the housing 168 of the surgical instrument 10 (FIG. 1) (e.g., integrated with microprocessor 500), or remote to the surgical instrument 10. The processor 928 displays the sonogram of the tissue adjacent the ultrasound probe 922 on a display (e.g., screen 122 of the user interface 120 or a monitor remote to the surgical instrument 10) to allow a clinician to visualize the tissue adjacent the ultrasound probe 922 before actuating the knife 906. During visualization of the tissue adjacent the ultrasound probe 922, a clinician is able to visualize attributes of tissue clamped within the end effector 160 such as areas of high density, areas of low density, foreign objects, and/or abnormal tissue before, during, and/or after actuating the knife 906.

Referring now to FIGS. 40-43, according to an embodiment of the present disclosure, microcontroller 405 controls the firing speed of staples 66 (FIG. 9) ejected by the surgical instrument 10 based on measured properties of the tissue being stapled, the drive motor 200, and/or other components of the surgical instrument 10. In particular, during firing of the staples 66, microcontroller 405 sets an initial speed of firing rod 220 based on a clamp force being exerted on the target tissue.

Figure 40:
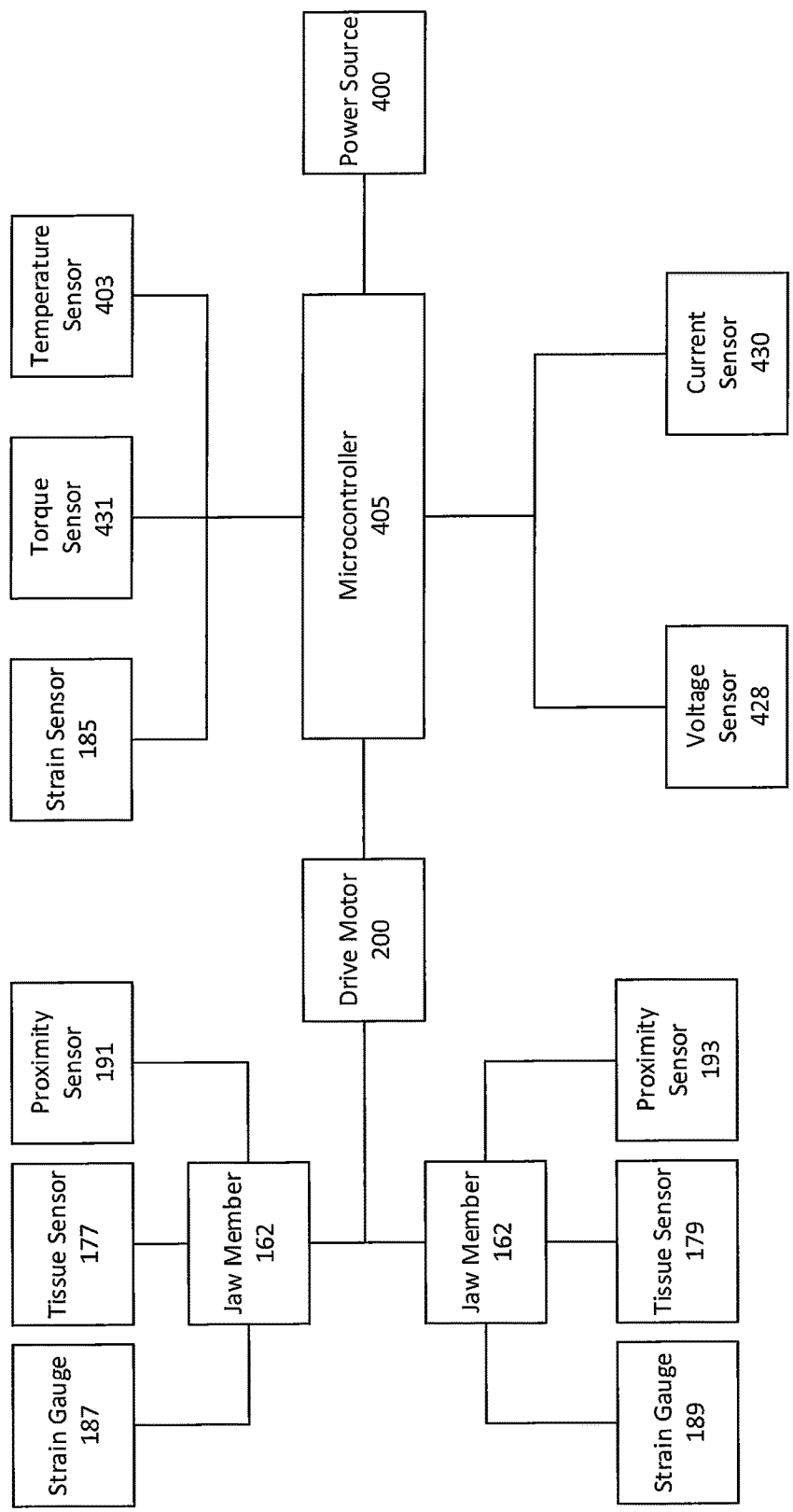
FIG. 40 is a schematic diagram of a control system of the powered surgical instrument according to the embodiment of the present disclosure of FIG. 1.

As depicted in FIG. 40, clamp force may be measured directly by sensors and/or calculated based on various sensor readings. In embodiments, force/load sensors, such as the strain sensor 185 or strain gauge sensor 187, 189 may be used to measure the load on the firing rod 220 (FIG. 6) and/or other load bearing components of the instrument 10. In embodiments, these sensors are coupled to the microcontroller 405.

Clamp force may also be determined based on voltage and current of the electrical energy being supplied to the drive motor 200 using voltage sensors 428 (e.g., voltmeter) and/or current sensors 430 (e.g., ammeter) coupled to the drive motor 200. In embodiments, a torque sensor 431 may also be used to monitor torque of the drive motor 200. In further embodiments, proximity sensors 191 and 193, which are configured to monitor proximity of the jaw members 162 and 164 may also be used to determine clamp force. In further embodiments, temperature sensors 403 (e.g., thermocouples, thermistors, etc.), which are coupled to various components of the instrument 10 (e.g., drive motor 200, the power source 400, microcontroller 405, etc.) may be used to monitor temperature. The microcontroller 405 may store various transfer functions which correlate measured voltage, current, torque, proximity measurements, and/or temperature to the clamp force. In particular, current draw and torque of the motor 200, which may be determined by the voltage and/or current sensors 428, 430 and torque sensors 431, respectively, may be used to correlate work done by the drive motor 200 to the clamp force. Similarly, proximity of the jaw members 162 and 164 in conjunction with other sensor measurements may also be utilized to extrapolate the clamp force.

In addition, the firing force of the staples 66 may also be determined by one or more of the sensors described above. In embodiments, current sensor 430, voltage sensor 428, and/or torque sensors 431 coupled to the drive motor 200 can be used such that measured properties, e.g., voltage, current, and motor torque, can then be correlated with the firing force of the staples 66. Peaks in current or voltage may be used to indicate increases in force or changes in load conditions.

The microcontroller 405 is also configured to continually adjust the firing speed based on the measured firing force of the staples 66 on the target tissue. Adjustment of the firing speed of the staples 66 from the cartridge assembly 162 optimizes staple formation. In particular, staples 66 fired with excess force or at excess speeds can produce malformed staples 66. Thus, adjustment of the firing speed helps minimize the force exerted on target tissue during staple firing.

Figure 41:
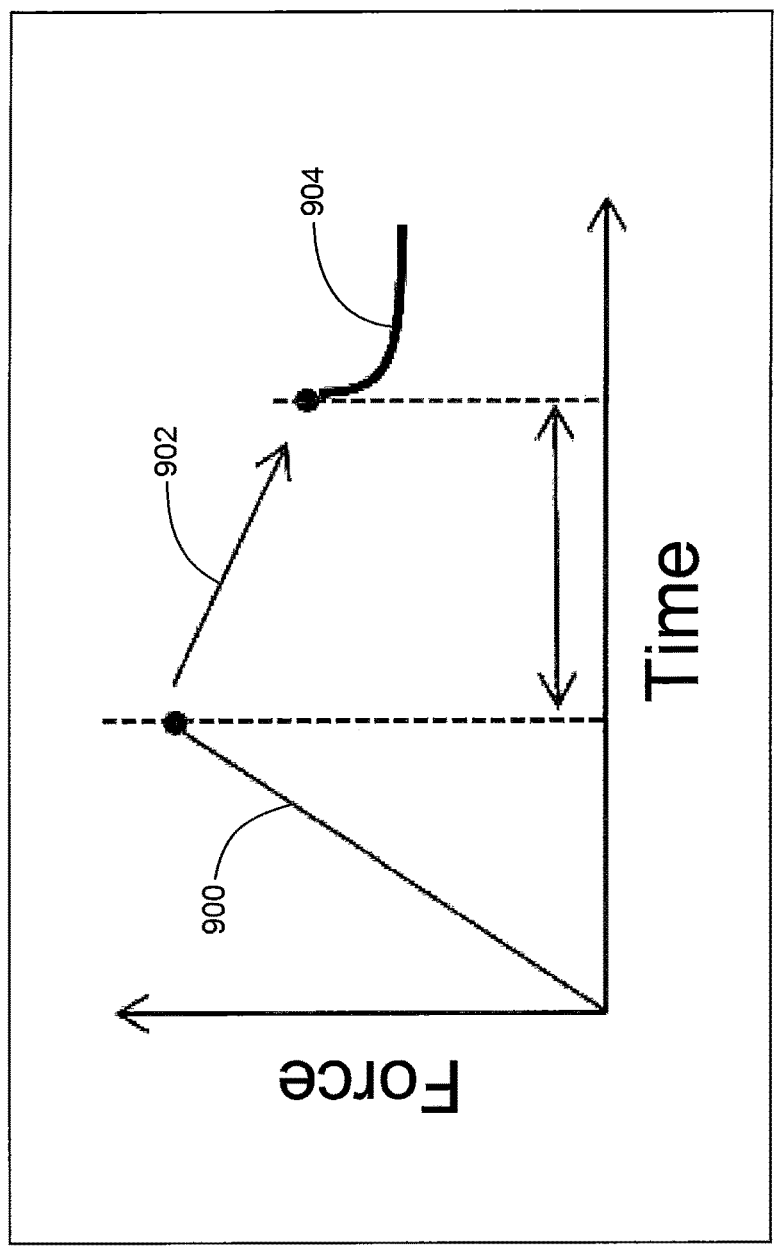
FIG. 41 is a graph illustrating force applied over time by the powered surgical instrument of FIG. 1 in accordance with an embodiment of the present disclosure.

The clamp force exerted on tissue during staple firing by the surgical instrument 10 based on an algorithm executed by the microcontroller 405 is illustrated in FIG. 41. The staple firing is described in three stages 900, 902, and 904. At stage 900, a user of instrument 10 initially clamps the end effector 160 on a target tissue, which is illustrated by an increase in the clamp force over time until the user clamps the end effector 160 on the target tissue. The microcontroller 405 determines the initial clamp force based on one or more sensor measurements, which is used to determine the starting firing speed. In particular, end effector 160 clamps the target tissue during which microcontroller 405 employs a delay during the stage 902, or a as illustrated by a gap between the force required to clamp tissue and initial force to begin firing after the wait time. Compression of the target tissue during the stage 902 reduces the amount of blood and fluid in the clamped tissue and provides for a more accurate maximum clamp force measurement. The stage 902 may be a predetermined time period set by a user or determined by microcontroller 405. After the stage 902, the staples 66 from the cartridge assembly 162 are fired at an initial firing speed.

Throughout the firing, the microcontroller 405 also continually monitors and determines the firing force of the staples 66 during the stage 904, and subsequently adjusts the firing speed based on the force feedback obtained during the stage 904. In particular, as shown in FIG. 41, the microcontroller 405 continually adjusts the firing speed to reduce the force exerted on the target tissue until a desired force is maintained. By continually adjusting the firing speed of the staples 66, microcontroller 405 minimizes the amount of force exerted on the tissue and optimizes staple formation.

Figure 42:
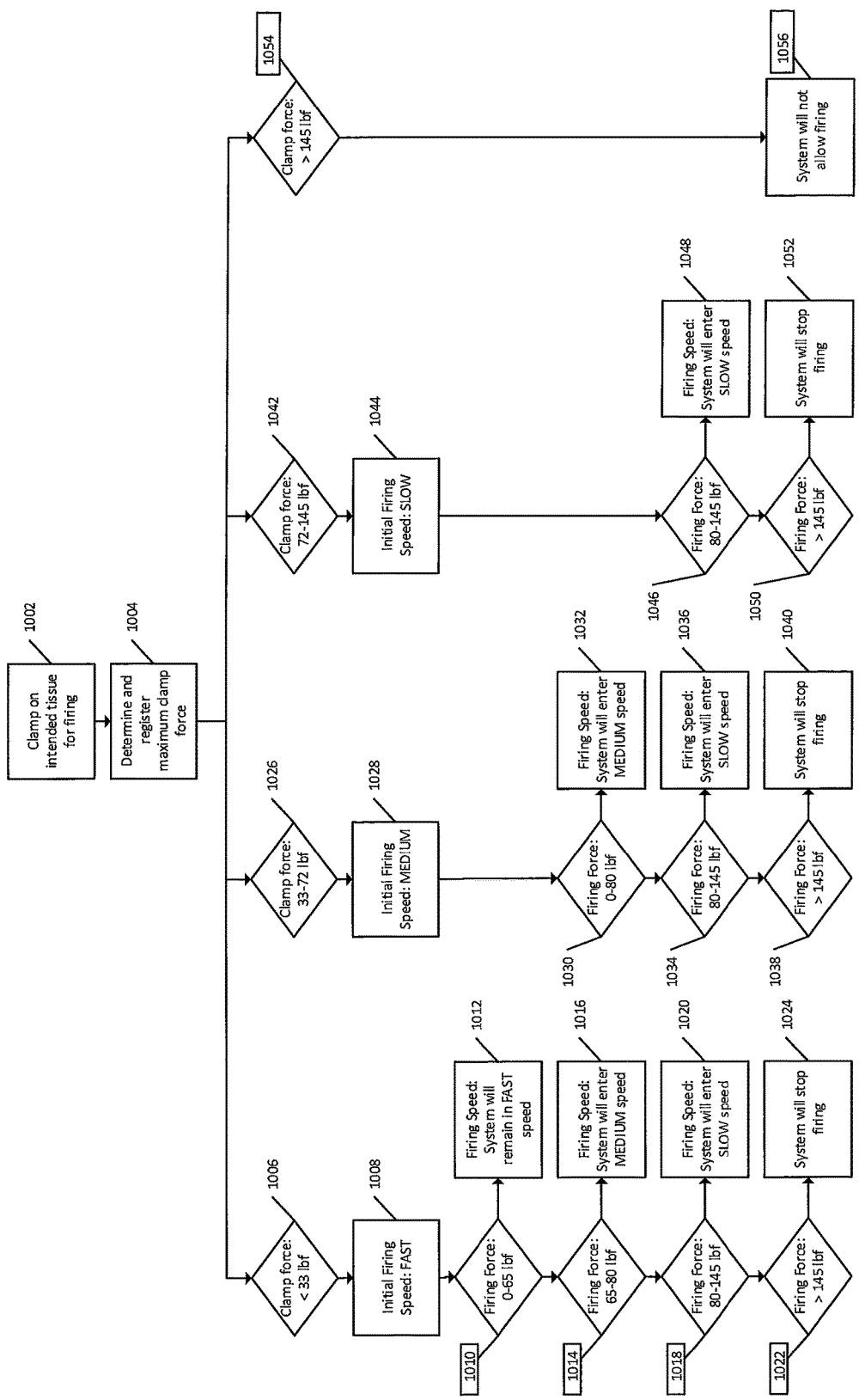
FIG. 42 is a flowchart illustrating a method for controlling the powered surgical instrument of FIG. 1 in accordance with an embodiment of the present disclosure.

FIG. 42 illustrates a flowchart of an algorithm executed by microcontroller 405 to control the surgical instrument 10 according to one embodiment of the present disclosure. Initially, at step 1002, drive motor 200 causes the drive beam 266 of the axial drive assembly 213 to actuate the end effector 160, which causes the jaw members 162, 164 of the end effector 160 to clamp onto the target tissue (FIGS. 1-6). In particular, the pair of cam members 40a of the retention flange 40 engage the jaw members 162, 164 during longitudinal advancement of the drive beam 266 (FIG. 8). At step 1004, sensors, e.g., strain gauges 187 and 189 (FIG. 17) or any of the other sensors previously described above, determine a maximum clamp force of jaw members 162, 164 on the target tissue Next, microcontroller 405 sets the initial firing speed of the staples 66 released by the staple cartridge 164 based on the measured maximum clamp force. In particular, microcontroller 405 controls the speed at which the drive motor 200 advances the drive beam 213, thereby controlling the speed at which the staples 66 are fired. Microcontroller 405 first determines if the measured maximum clamp force falls within one of a plurality of predetermined ranges. In the embodiment depicted in FIG. 42, microcontroller 405 contains four different predetermined ranges 1006, 1026, 1042, 1054. The ranges are defined by a first threshold (e.g., about 33 pound-force (lbf)), a second threshold (e.g., about 72 lbf), and a third threshold (e.g., about 145 lbf). If the jaw members 162 and 164 exert a maximum clamp force on the target tissue below the first threshold at step 1006, the microcontroller 405 sets the initial firing speed of the staples 66 to a first speed (e.g., "FAST" speed) at step 1008. If the maximum clamp force is between the first threshold and the second threshold at step 1026, the microcontroller 405 sets the initial firing speed of the staples 66 to a second speed (e.g., "MEDIUM" speed) at step 1028. If the maximum clamp force is between the second threshold and the third threshold at step 1042, the microcontroller 405 sets an initial firing speed of the staples 66 to a third speed (e.g., "SLOW" speed) at step 1044. Lastly, if the maximum clamp force is greater than the third threshold at step 1054, the microcontroller 405 prevents the system from firing at 1056. The force values for each of the ranges, the number of ranges and corresponding speed settings that are described above are exemplary and may be modified based on a variety of factors, such as the needs of the clinician, the surgical instrument 10 being used, procedure being performed, staples 66 being used, etc.

If the microcontroller 405 sets the initial firing speed to first, second, or third speeds, the microcontroller 405 continually monitors the force exerted on the tissue by the staples 66 as the staples 66 are fired, i.e., the firing force, and continually adjusts the firing speed of the staples 66, accordingly. In particular, during firing of the staples 66, the microcontroller 405 continually monitors and adjusts the firing speed based on whether the measured firing force falls within a predetermined range. As depicted in FIG. 42, if the initial firing speed is set to the first speed (e.g. "FAST") at step 1008 and the microcontroller 405 subsequently determines that the firing force is less than a first threshold (e.g., 65 lbf) at step 1010, the microcontroller 405 maintains the firing speed at the preset first speed at 1012. However, if the firing force increases, such that it is between the first threshold (e.g., 65 lbf) and a second threshold (e.g., 80 lbf) at step 1014, the microcontroller 405 adjusts the firing speed to the second speed (e.g. "MEDIUM") at step 1016. However, if the firing force is between the second threshold and a third threshold (e.g., 145 lbf) at step 1018, the microcontroller 405 adjusts the firing speed to the third speed (e.g., "SLOW") at step 1020. If the firing force rises above the third threshold at step 1022, the microcontroller 405 stops the firing of the staples 66 at step 1024. This can occur when the staples 66 have completed firing or if the staples 66 encounter an unknown obstruction. This feature can prevent damage to the instrument 10 and/or the tissue.

In embodiments when the initial firing speed is set to the second speed (e.g., "MEDIUM") or the third speed (e.g., "SLOW") at steps 1028 and 1044, microcontroller 405 adjusts the firing forces by modifying the threshold ranges. With respect to the particular embodiment depicted in FIG. 42, if the initial firing speed is set to the second speed at step 1028 and the firing force remains below the second threshold at step 1030, the microcontroller 405 keeps the firing speed at the second speed at step 1032. However, the microcontroller 405 changes the firing speed to the third speed at step 1036 if the firing force rises to be between the second threshold and the third threshold at step 1034. Likewise, if the initial firing speed is set to the third speed at step 1044 and the firing force remains below the third threshold at step 1048, the microcontroller 405 keeps the firing speed at the third threshold at step 1048. In all three cases, if the initial firing speed is set based on either the first, second, or third thresholds and the firing force rises above the third threshold at steps 1022, 1038, and 1050, the microcontroller 405 stops the firing of any further staples 66 at steps 1024, 1040, and 1052, respectively.

Figure 43:
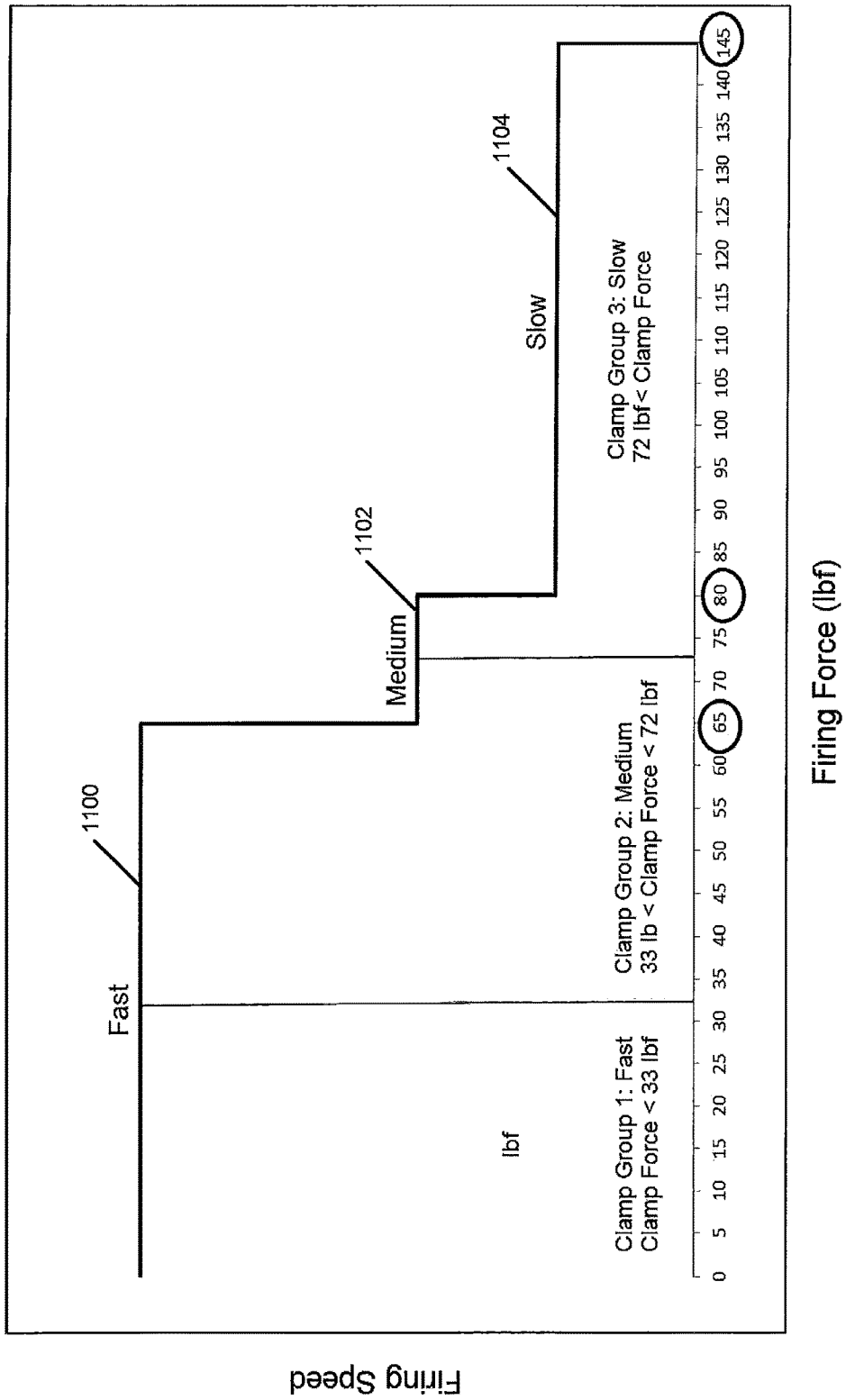
FIG. 43 is a graph illustrating firing speed over force applied by the powered surgical instrument in accordance with an embodiment of the present disclosure.

FIG. 43 depicts a graphical representation of exemplary firing speeds and forces based on the algorithm described above with respect to FIG. 42. In particular, FIG. 43 depicts firing speed (on the y-axis) versus firing force (on the x-axis). As detailed above, the microcontroller 405 determines an initial firing speed (e.g., "FAST" (1100), "MEDIUM" (1102), or "SLOW" 1104) based on an initial clamp force. In FIG. 43, the initial clamp force is grouped into one of three groups: Group 1 if the clamp force is below the first threshold (e.g., 33 lbf); Group 2 if the claim force is between the first threshold and the second threshold (e.g., 72 lbf); and Group 3 if the clamp force is between the second threshold and the third threshold (e.g., 145 lbf). In the embodiment depicted in FIG. 43, the initial firing speed is set to the first speed (e.g., "FAST") for Group 1, the second speed (e.g., "MEDIUM") for Group 2, and (e.g., "SLOW") for Group 3. Once the initial firing speed is set, microcontroller 405 adjusts the firing speed based on the measured firing force. As shown in FIG. 43, if the firing force exceeds the first threshold (e.g., 65 lbf), the initial firing speed drops from the first speed to the second speed. If the firing speed exceeds the second threshold (e.g., 80 lbf), the initial firing speed drops from the second speed to the third speed, and if the firing speed exceeds the third threshold (e.g., 145 lbf), the microcontroller 405 stops firing of the staples 66.

The above disclosure describes a predictive style adaptive stapling algorithm that optimizes staple formation and minimizes force during firing of a staple from a powered surgical instrument, e.g., a surgical stapler. Using the method described above, a surgeon clamps the jaw members of the surgical instrument on tissue, the clamp force influences the utilization of a wait and hold time on the tissue as well as the starting firing speed, and throughout the firing, the surgical instrument has the ability to slow down the firing speed based on force feedback. By controlling the firing speed by the surgical instrument, the above described method optimizes the firing force on target tissue and minimizes the percentage of malformed staples.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical stapler, comprising:
   a handle assembly;
   an end effector coupled to the handle assembly, the end effector including:
      a first jaw member including a surgical fastener; and
      a second jaw member including an anvil portion, at least one of the first jaw member or the second jaw member is moveable relative to one another between an open position and a clamped position;
   a firing rod disposed in mechanical cooperation with the end effector;
   a drive motor coupled to the firing rod, the drive motor configured to advance the firing rod to cause the first and second jaw members to clamp tissue and to eject the surgical fastener;
   a sensor configured to measure a clamping force exerted on tissue by the first and second jaw members; and
   a controller operatively coupled to the drive motor and configured to:
   measure a maximum clamp force of the first and second jaw member on tissue;
   set a speed of the drive motor based on the measured maximum clamp force; and
   control the speed of the drive motor based on the measured clamping force.

2. The surgical stapler according to claim 1, wherein the controller is further configured to set the speed of the drive motor to a first firing speed in response to the measured clamping force being between a first threshold clamping force and a second threshold clamping force.

3. The surgical stapler according to claim 2, wherein the first threshold clamping force is about 0 pound-force (lbf) and the second threshold clamping force is about 33 lbf.

4. The surgical stapler according to claim 2, wherein the first threshold clamping force is about 33 lbf and the second threshold clamping force is about 72 lbf.

5. The surgical stapler according to claim 2, wherein the first threshold clamping force is about 72 lbf and the second threshold clamping force is about 145 lbf.

6. The surgical stapler according to claim 1, wherein the controller is further configured to stop the drive motor in response to the measured clamping force being greater than a first threshold clamping force.

7. The surgical stapler according to claim 6, wherein the first threshold clamping force is about 145 lbf.

8. The surgical stapler according to claim 1, wherein the sensor is further configured to measure a firing force exerted on the surgical fastener.

9. The surgical stapler according to claim 8, wherein the controller is further configured to set the speed of the drive motor to a second firing speed in response to the measured clamping force being between a first firing force threshold and a second firing force threshold.

10. The surgical stapler according to claim 9, wherein the first firing force threshold is about 0 lbf and the second firing force threshold is about 65 lbf.

11. The surgical stapler according to claim 9, wherein the first firing force threshold is about 65 lbf and the second firing force threshold is about 80 lbf.

12. The surgical stapler according to claim 9, wherein the first firing force threshold is about 80 lbf and the second firing force threshold is about 145 lbf.

13. The surgical stapler according to claim 9, wherein the controller stops the drive motor based on the firing force being greater than a first firing force threshold.

14. The surgical stapler according to claim 13, wherein the first firing force threshold is about 145 lbf.

15. The surgical stapler according to claim 1, wherein the sensor is a strain gauge sensor disposed on at least one of the first jaw member, the second jaw member, or the firing rod.

16. The surgical stapler according to claim 1, wherein the sensor is configured to measure the clamping force by monitoring at least one of a speed of the drive motor, a torque being applied by the drive motor, a distance between the first and second jaw members, a temperature of the drive motor, or a load exerted on the firing rod.

17. A method of controlling a firing speed of a surgical stapler, the method comprising:
    positioning tissue between a first jaw member and a second jaw member of an end effector, at least one of the first jaw member or the second jaw member being moveable relative to one another, the first jaw member including a staple cartridge;
    measuring a maximum clamp force of the first and second jaw member on the tissue;
    setting a firing speed of a drive motor for ejecting a staple from the staple cartridge based on the measured maximum clamp force;
    initiating firing of the staple from the staple cartridge;
    measuring a firing force exerted on the staple; and
    adjusting the firing speed of the surgical stapler based on the measured firing force.

18. The method according to claim 17, further comprising stopping the firing of the staple from the staple cartridge in response to the measured firing force being greater than a first firing force threshold.

19. The method according to claim 18, wherein the first firing force threshold is about 145 pound-force (lbf).

20. The method according to claim 17, wherein the maximum clamp force is measured by a sensor configured to measure the maximum clamping force by monitoring at least one of a speed of the drive motor, a torque being applied by the drive motor, or a distance between the first and second jaw members.

* * * * *